United States Patent
Rogers et al.

(10) Patent No.: US 9,849,026 B2
(45) Date of Patent: Dec. 26, 2017

(54) APPARATUS AND METHODS FOR PRODUCING BRAIN ACTIVATION VIA THE VESTIBULAR SYSTEM WITH TIME-VARYING WAVEFORMS

(75) Inventors: Lesco L. Rogers, Raleigh, NC (US); Lanty L. Smith, Raleigh, NC (US); Robert D. Black, Chapel Hill, NC (US)

(73) Assignee: Scion NeuroStim, LLC, Raleigh, NC (US)

( * ) Notice: Subject to any disclaimer, the term of this patent is extended or adjusted under 35 U.S.C. 154(b) by 581 days.

(21) Appl. No.: 13/990,274

(22) PCT Filed: Dec. 16, 2011

(86) PCT No.: PCT/US2011/065321
§ 371 (c)(1),
(2), (4) Date: Jul. 24, 2013

(87) PCT Pub. No.: WO2012/083098
PCT Pub. Date: Jun. 21, 2012

(65) Prior Publication Data
US 2013/0317576 A1    Nov. 28, 2013

Related U.S. Application Data

(63) Continuation-in-part of application No. PCT/US2010/060764, filed on Dec. 16, 2010, and a
(Continued)

(51) Int. Cl.
*A61B 18/18* (2006.01)
*A61F 7/12* (2006.01)
(Continued)

(52) U.S. Cl.
CPC ................ *A61F 7/12* (2013.01); *A61F 7/007* (2013.01); *A61N 2/002* (2013.01); *A61N 2/006* (2013.01);
(Continued)

(58) Field of Classification Search
CPC ... A61B 2018/00875; A61F 2007/0005; A61F 2007/0075; A61F 2007/0093;
(Continued)

(56) References Cited

U.S. PATENT DOCUMENTS 4,117,881 A    10/1978   Williams et al.
4,244,377 A    1/1981    Grams
(Continued)

FOREIGN PATENT DOCUMENTS

DE   100 65 592 A1   7/2002
JP   08-195997 A     7/1996
(Continued)

OTHER PUBLICATIONS

U.S. Appl. No. 12/704,872, filed Feb. 12, 2010; Office Action mailed Jan. 29, 2013.
(Continued)

*Primary Examiner* — Michael Peffley
*Assistant Examiner* — Amanda Zink
(74) *Attorney, Agent, or Firm* — Myers Bigel, P.A.

(57) ABSTRACT

A device for delivering caloric vestibular stimulation to an individual, includes: (a) an earpiece configured to be at least partially insertable into the ear canal of the individual for delivering said caloric vestibular stimulation; (b) a power supply operatively associated with said earpiece; and (c) a controller operatively associated with said power supply and said earpiece for configuring said caloric vestibular stimulation as at least a first and second time-varying waveform. Preferably, the waveforms are actively controlled waveforms.

20 Claims, 42 Drawing Sheets

Related U.S. Application Data continuation-in-part of application No. 12/970,312, filed on Dec. 16, 2010, now Pat. No. 8,460,356, and a continuation-in-part of application No. 12/970,347, filed on Dec. 16, 2010, now Pat. No. 8,603,152.

(60) Provisional application No. 61/424,474, filed on Dec. 17, 2010, provisional application No. 61/424,132, filed on Dec. 17, 2010, provisional application No. 61/424,326, filed on Dec. 17, 2010, provisional application No. 61/497,761, filed on Jun. 16, 2011, provisional application No. 61/498,096, filed on Jun. 17, 2011, provisional application No. 61/498,131, filed on Jun. 17, 2011, provisional application No. 61/498,080, filed on Jun. 17, 2011, provisional application No. 61/498,911, filed on Jun. 20, 2011, provisional application No. 61/498,943, filed on Jun. 20, 2011.

(51) Int. Cl.
| | | |
|---|---|---|
| *A61F 7/00* | (2006.01) | |
| *A61N 2/00* | (2006.01) | |
| *A61B 18/00* | (2006.01) | |
| *A61F 7/02* | (2006.01) | |
| *A61N 1/36* | (2006.01) | |

(52) U.S. Cl.
CPC .............. *A61B 2018/00875* (2013.01); *A61F 2007/0005* (2013.01); *A61F 2007/0075* (2013.01); *A61F 2007/0093* (2013.01); *A61F 2007/0095* (2013.01); *A61F 2007/0096* (2013.01); *A61F 2007/0296* (2013.01); *A61N 1/36036* (2017.08)

(58) Field of Classification Search
CPC ...... A61F 2007/0095; A61F 2007/0296; A61F 7/007; A61F 7/12
See application file for complete search history.

(56) References Cited

U.S. PATENT DOCUMENTS

| | | | |
|---|---|---|---|
| 4,449,528 A | 5/1984 | Auth et al. | |
| 4,860,748 A | 8/1989 | Chiurco et al. | |
| 4,918,757 A | 4/1990 | Janssen et al. | |
| 5,097,828 A | 3/1992 | Deutsch | |
| 5,215,086 A | 6/1993 | Terry, Jr. et al. | |
| 5,367,890 A | 11/1994 | Doke | |
| 5,376,184 A | 12/1994 | Aspden | |
| 5,419,780 A | 5/1995 | Suski | |
| 5,746,702 A | 5/1998 | Gelfgat et al. | |
| 5,762,612 A | 6/1998 | Campbell | |
| 5,837,929 A | 11/1998 | Adelman | |
| 5,871,526 A | 2/1999 | Gibbs et al. | |
| 6,016,449 A | 1/2000 | Fischell et al. | |
| 6,017,337 A | 1/2000 | Pira | |
| 6,055,815 A | 5/2000 | Peterson | |
| 6,094,918 A | 8/2000 | Burbidge | |
| 6,143,975 A | 11/2000 | Liao et al. | |
| 6,165,173 A | 12/2000 | Kamdar et al. | |
| 6,300,150 B1 | 10/2001 | Venkatasubramanian | |
| 6,334,311 B1 | 1/2002 | Kim et al. | |
| 6,511,437 B1 | 1/2003 | Nakamura et al. | |
| 6,746,474 B2 | 6/2004 | Saadat | |
| 6,755,026 B2 | 6/2004 | Wallach | |
| 6,817,191 B2 | 11/2004 | Watanabe | |
| 6,875,196 B2 | 4/2005 | Abita et al. | |
| 6,882,881 B1 | 4/2005 | Lesser et al. | |
| 6,909,917 B2 | 6/2005 | Woods et al. | |
| 6,921,195 B2 | 7/2005 | Pipe et al. | |
| 6,981,381 B1 | 1/2006 | Wang et al. | |
| 7,082,772 B2 | 8/2006 | Welch | |
| 7,164,077 B2 | 1/2007 | Venkatasubramanian | |
| 7,189,252 B2 | 3/2007 | Krueger | |
| 7,234,735 B2 | 6/2007 | Harada | |
| 7,761,168 B2 | 7/2010 | Gross | |
| 7,856,275 B1 | 12/2010 | Paul et al. | |
| 8,083,786 B2 | 12/2011 | Gafni et al. | |
| 8,460,356 B2 | 6/2013 | Rogers et al. | |
| 9,283,111 B2 | 3/2016 | Rogers et al. | |
| 2002/0072781 A1 | 6/2002 | Lattner et al. | |
| 2002/0104318 A1 | 8/2002 | Jaafar et al. | |
| 2002/0121094 A1 | 9/2002 | VanHoudt | |
| 2003/0097845 A1 | 5/2003 | Saunders et al. | |
| 2003/0099279 A1 | 5/2003 | Venkatasubramanian et al. | |
| 2003/0101006 A1 | 5/2003 | Mansky et al. | |
| 2003/0158589 A1 | 8/2003 | Katsnelson | |
| 2003/0195588 A1* | 10/2003 | Fischell | A61N 2/02 607/55 |
| 2004/0102525 A1 | 5/2004 | Kozachuk | |
| 2004/0181269 A1 | 9/2004 | Lee | |
| 2004/0193237 A1 | 9/2004 | Krueger | |
| 2005/0107682 A1 | 5/2005 | Rao et al. | |
| 2005/0145273 A1 | 7/2005 | Atwood et al. | |
| 2005/0165460 A1 | 7/2005 | Erfan | |
| 2005/0203505 A1 | 9/2005 | Megerman et al. | |
| 2006/0082971 A1 | 4/2006 | Artman et al. | |
| 2006/0086118 A1 | 4/2006 | Venkatasubramanian et al. | |
| 2006/0095088 A1 | 5/2006 | De Ridder | |
| 2006/0289050 A1 | 12/2006 | Alley et al. | |
| 2006/0289052 A1 | 12/2006 | O'Quinn et al. | |
| 2006/0293732 A1 | 12/2006 | Collins et al. | |
| 2007/0028956 A1 | 2/2007 | Venkatasubramanian et al. | |
| 2007/0083097 A1 | 4/2007 | Fujiwara et al. | |
| 2007/0087780 A1 | 4/2007 | Nassimi | |
| 2007/0089773 A1 | 4/2007 | Koester et al. | |
| 2007/0135880 A1 | 6/2007 | Eggers et al. | |
| 2007/0167985 A1 | 7/2007 | Kirby | |
| 2007/0198063 A1 | 8/2007 | Hunter et al. | |
| 2007/0203539 A1 | 8/2007 | Stone et al. | |
| 2007/0215194 A1 | 9/2007 | Bharathan et al. | |
| 2007/0225781 A1 | 9/2007 | Saadat et al. | |
| 2007/0226890 A1 | 10/2007 | Pflueger | |
| 2007/0250119 A1 | 10/2007 | Tyler et al. | |
| 2007/0265524 A1 | 11/2007 | Eda et al. | |
| 2008/0015667 A1 | 1/2008 | Gross | |
| 2008/0087316 A1 | 4/2008 | Inaba et al. | |
| 2008/0097549 A1 | 4/2008 | Colbaugh et al. | |
| 2008/0154334 A1 | 6/2008 | Gavronsky | |
| 2008/0168775 A1 | 7/2008 | Windheim et al. | |
| 2008/0182399 A1 | 7/2008 | Cho | |
| 2008/0264464 A1 | 10/2008 | Lee et al. | |
| 2009/0082831 A1* | 3/2009 | Paul | A61N 1/0456 607/59 |
| 2009/0182399 A1* | 7/2009 | Sylvestre | A61F 7/12 607/99 |
| 2010/0198204 A1 | 8/2010 | Rogers et al. | |
| 2010/0198282 A1* | 8/2010 | Rogers | A61F 7/007 607/3 |
| 2010/0198318 A1 | 8/2010 | Rogers | |
| 2010/0211142 A1 | 8/2010 | Rogers et al. | |
| 2011/0313498 A1 | 12/2011 | Rogers et al. | |
| 2011/0313499 A1 | 12/2011 | Smith et al. | |
| 2012/0078337 A1 | 3/2012 | Darley et al. | |
| 2012/0316624 A1 | 12/2012 | Smith et al. | |
| 2015/0224251 A1 | 8/2015 | Rooney et al. | |

FOREIGN PATENT DOCUMENTS

| | | |
|---|---|---|
| JP | H08195997 | 7/1996 |
| JP | 09-285468 A | 11/1997 |
| JP | H09285468 | 11/1997 |
| JP | 2002-123456 A | 4/2002 |
| JP | 2006-102258 A | 4/2006 |
| JP | 2006102258 | 4/2006 |
| JP | 2007-144057 A | 6/2007 |
| WO | WO 02/064069 A2 | 8/2002 |
| WO | WO 2005/074463 A2 | 8/2005 |
| WO | WO 2006/079484 A1 | 8/2006 |
| WO | WO 2007/051911 A1 | 5/2007 |

(56) References Cited

FOREIGN PATENT DOCUMENTS

| WO | WO 2009/020862 A2 | 2/2009 |
| WO | WO 2010/029536 | 3/2010 |
| WO | WO 2010/029536 A2 | 3/2010 |
| WO | WO 2012/083126 | 6/2012 |

OTHER PUBLICATIONS

Australian Examination Report Corresponding to Australian Patent Application No. 2008284042; Date of Issue: Oct. 9, 2012; 3 Pages.
Baier et al., "Evidence for Modulation of Opioidergic Activity in Central Vestibular Processing: A [$^{18}$F] Diprenorphine PET Study," Hum. Brain Mapp. 31:550-555 (2010).
Been et al., "The use of tDCS and CVS as methods of non-invasive brain stimulation," J. Brain Res. Rev. 56:346-361 (2007).
Bense et al., "Preserved visual-vestibular interaction in patients with bilateral vestibular failure," Neurol. 63:122-128 (2004).
Brookler, "Simultaneous Bilateral Bithermal Caloric Stimulation in Electronystagmography," Presented at the Meeting of the Eastern Section of the American Laryngological Rhinological and Otological Society, Inc., Britannia Beach Hotel, Paradise Island, Nassau, Jan. 17, 1971.
Coats AC. Temperature effects on the peripheral auditory apparatus. Science. Dec. 10, 1965; 150(702): 1481-1483.
Deutschländer et al., "Sensory System Interactions During Simultaneous Vestibular and Visual Stimulation in PET," Hum. Brain Mapp. 16:92-103 (2002).
Dieterich et al., "Functional brain imaging of peripheral and central vestibular disorders," Brain 131:2538-2552 (2008).
Ettenberg et al. "A New n-type and Improved p-type Pseudo-ternary ($Bi_2Te_3$)($Sb_2Se_3$) Alloy for Peltier Cooling" 15$^{th}$ International Conference on Thermoelectrics, IEEE Catalog No. 96TH8169 pp. 52-56 (1996).
Fasold et al., "Human Vestibular Cortex as Identified with Caloric Stimulation in Functional Magnetic Resonance Imaging," NeuroImage 17:1384-1393 (2002).
Ferré et al., "Vestibular inputs modulate somatosensory cortical processing," Brain Struct, Funct. 217:859-864 (2012).
Ferré et al., "Vestibular modulation of somatosensory perception," Eur. J. Neurosci. 34:1337-1344 (2011).
Fontanazza "A Cooler Way to Stop Seizures" *Medical Device & Diagnostic Industry Magazine* pp. 1-2 (2005).
International Preliminary Report on Patentability Corresponding to International Application No. PCT/US2011/065328; Date of Mailing: Jun. 27, 2013; 12 Pages.
International Preliminary Report on Patentability Corresponding to International Application No. PCT/US2011/065321; Date of Mailing: Jun. 27, 2013; 9 Pages.
International Preliminary Report on Patentability Corresponding to International Application No. PCT/US2011/065396; Date of Mailing: Jun. 27, 2013; 7 Pages.
International Preliminary Report on Patentability Corresponding to International Application No. PCT/US2011/065338; Date of Mailing: Jun. 27, 2013; 7 Pages.
International Preliminary Report on Patentability Corresponding to International Application No. PCT/US2011/065456; Date of Mailing: Jun. 27, 2013; 8 Pages.
International Preliminary Report on Patentability Corresponding to International Application No. PCT/US2010/060764, Date of Mailing: Jun. 28, 2012; 9 Pages.
International Preliminary Report on Patentability for Application No. PCT/US10/60771, mailed May 17, 2012.
International Search Report and Written Opinion Corresponding to International Application No. PCT/US2011/065328; Date of Mailing: Mar. 29, 2012; 13 Pages.
International Search Report and Written Opinion Corresponding to International Application No. PCT/US2011/065321; Date of Mailing: Mar. 29, 2012; 10 Pages.
International Search Report and Written Opinion Corresponding to International Application No. PCT/US2011/065396; Date of Mailing: Apr. 23, 2012; 8 Pages.
International Search Report and Written Opinion Corresponding to International Application No. PCT/US2011/065338; Date of Mailing: Apr. 20, 2012; 8 Pages.
International Search Report and Written Opinion Corresponding to International Application No, PCT/US2011/065456; Date of Mailing: Apr. 4, 2012; 9 Pages.
International Search Report and Written Opinion Corresponding to International Application No. PCT/US2010/060764; Date of Mailing: Feb. 22, 2011.
International Search Report and Written Opinion for PCT/US2010/060771 mailed on Feb. 22, 2011.
International Search Report and Written Opinion, PCT/US2008/071935, mailed Jul. 16, 2009.
Japanese Office Action Corresponding to Japanese Patent Application No. 2010-519241; Dispatch Date: Dec. 7, 2012; Foreign Text, 5 Pages, English Translation Thereof, 4 Pages.
Karim et al., "Neuroimaging to detect cortical projection of vestibular response to caloric stimulation in young and older adults using functional near-infrared spectroscopy (fNIRS)," NeuroImage 76:1-10 (2013).
Kimm et al., "Vestibular Effects of Electrical Stimulation of the Cochlea," Arch. Otolaryngol. 105:175-179 (1979).
Klingner et al., "Components of vestibular cortical function," Behav. Brain Res. 236:194-199 (2013).
Kolev "How caloric vestibular irritation influences migraine attacks" *Cephalalgia* 10:167-169, 1990.
Litchfield, "Biomedical Device Maker Teams with NASA to Develop Nano-Sized Biothermal Battery", http://www.devicelink,com/emdm/archive/04/10/002.html, 2 pages, European Medical Device Manufacturer (Oct. 2004).
Lobel et al., "Functional MRI of Galvanic Vestibular Stimulation," J. Neurophysiol. 80:2699-2709 (1998).
Lopez et al., "The Human Vestibular Cortex Revealed by Coordinate-Based Activation Likelihood Estimation Meta-Analysis," Neurosci. 212:159-179 (2012).
Marcelli et al., "Spatio-temporal pattern of vestibular information processing after brief caloric stimulation," Eur. J. of Radiol. 70:312-316 (2009).
Marcelli et al; "Spatio-temporal pattern of vestibular information processing after brief caloric stimulation"; (2008) EJR (European Journal of Radiology) Elsevier EURR-3758; No. of pp. 5.
Mast et al., "Visual mental imagery during caloric vestibular stimulation", Neuropsychologia 44(1):101-109 (2006).
McGeoch et al., "Post-stroke tactile allodynia and its modulation by vestibular stimulation: a MEG case study," Acta Neurol. Scand 119:404-409 (2009).
Miller et al., "Studies of caloric vestibular stimulation: implications for the cognitive neurosciences, the clinical neurosciences and neurophilosophy", Acta Neuropsychiatrica 19:183-203 (2007).
Naito et al., "Cortical correlates of vestibule-ocular reflex modulation: a PET study," Brain 126:1562-1578 (2003).
Nextreme Thermal Solutions, Inc. "Breakthroughs: Thermoelectric Generator Converts Waste Heat into Energy" MPMN Oct. 2007 http:/www.devicelink.com/mpmn/archive/07/10/014.html.
Ramachandran et al., "Can vestibular caloric stimulation be used to treat apotemnophilia?," Med. Hypotheses 69:250-252 (2007).
Ried "Asymmetries of Vestibular Dysfunction in Major Depression" *Neuroscience* 144:128-134, 2007.
Rode et al., "Bilateral vestibular stimulation does not improve visual hemineglect," Neuropsychologia 40:1104-1106 (2002).
Rothman, "Pathophysiology and therapy of epilepsy", 2 pages, Website of Professor Steven Rothman, M.D., Washington University of St. Louis: http://neuroscience.wustl.edu/research/faculty.php?id=81.
Schiff et al., "Does vestibular stimulation activate thalamocortical mechanisms that reintegrate impaired cortical regions?," Proc. R. Soc. Lond. 266:421-423 (1999).
Snyder et al., "Hot Spot Cooling using Embedded Thermoelectric Coolers", 22$^{nd}$ IEEE SEMI-THERM Symposium, IEEE Catalog No. 1-4244-0154-2, pp. 135-143 (2006).

(56) References Cited

OTHER PUBLICATIONS

Tellurex Corp. "Thermoelectric cooling semiconductor modules available in new configuration" MPMN: Cover Products Apr. 1999 http://www.devicelink.com/mpmn/archive/99/04/cover.html.
Venkatasubramanian et al. "Phonon-Blocking Electron-Transmitting Structures" 18$^{th}$ International Conference on Thermoelectrics (1999).
Vitte et al., "Activation of the hippocampal formation by vestibular stimulation: a functional magnetic resonance imaging study," Exp. Brain Res. 112:523-526 (1996).
Zhang Na, et al; "Change of extracellular ascorbic acid in the brain cortex following ice water vestibular stimulation: an on-line electrochemical detection coupled with in vivo microdialysis sampling for guinea pigs"; Chin Med J. 2008: 121 (12): 1120-1125.
Japanese Office Action Corresponding to Japanese Patent Application No. 2013-544811; Dispatch Date: Dec. 1, 2015.
European Search Report Corresponding to Patent Application No. 14 163 419; Dated: Jan. 8, 2015; 3 Pages.
Shinji Nishizawa, "Intervals for Successive Caloric Irrigations", Equilibrium Research, Japan Society for Equilibrium Research, 2001, vol. 60, p. 86-92.

* cited by examiner

Figure 6

Figure 18A
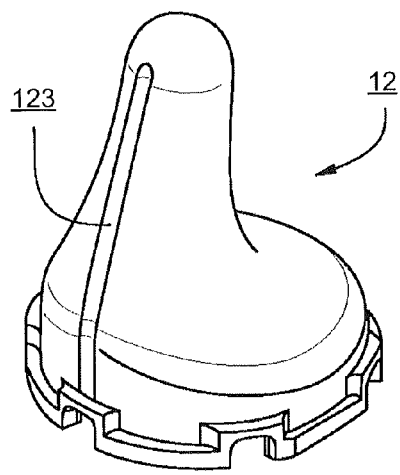
Figure 18B
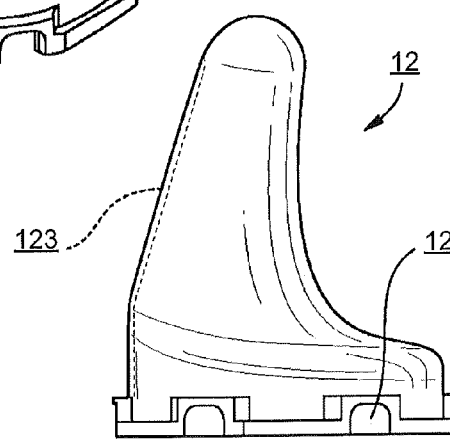
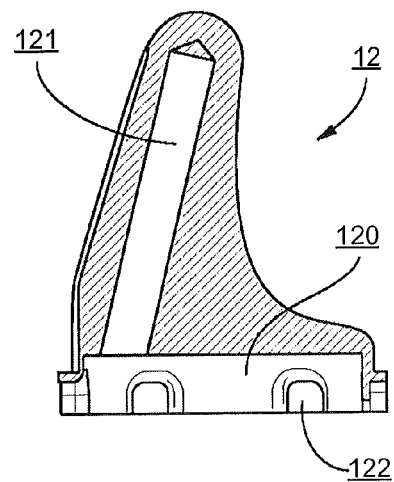
Figure 18C

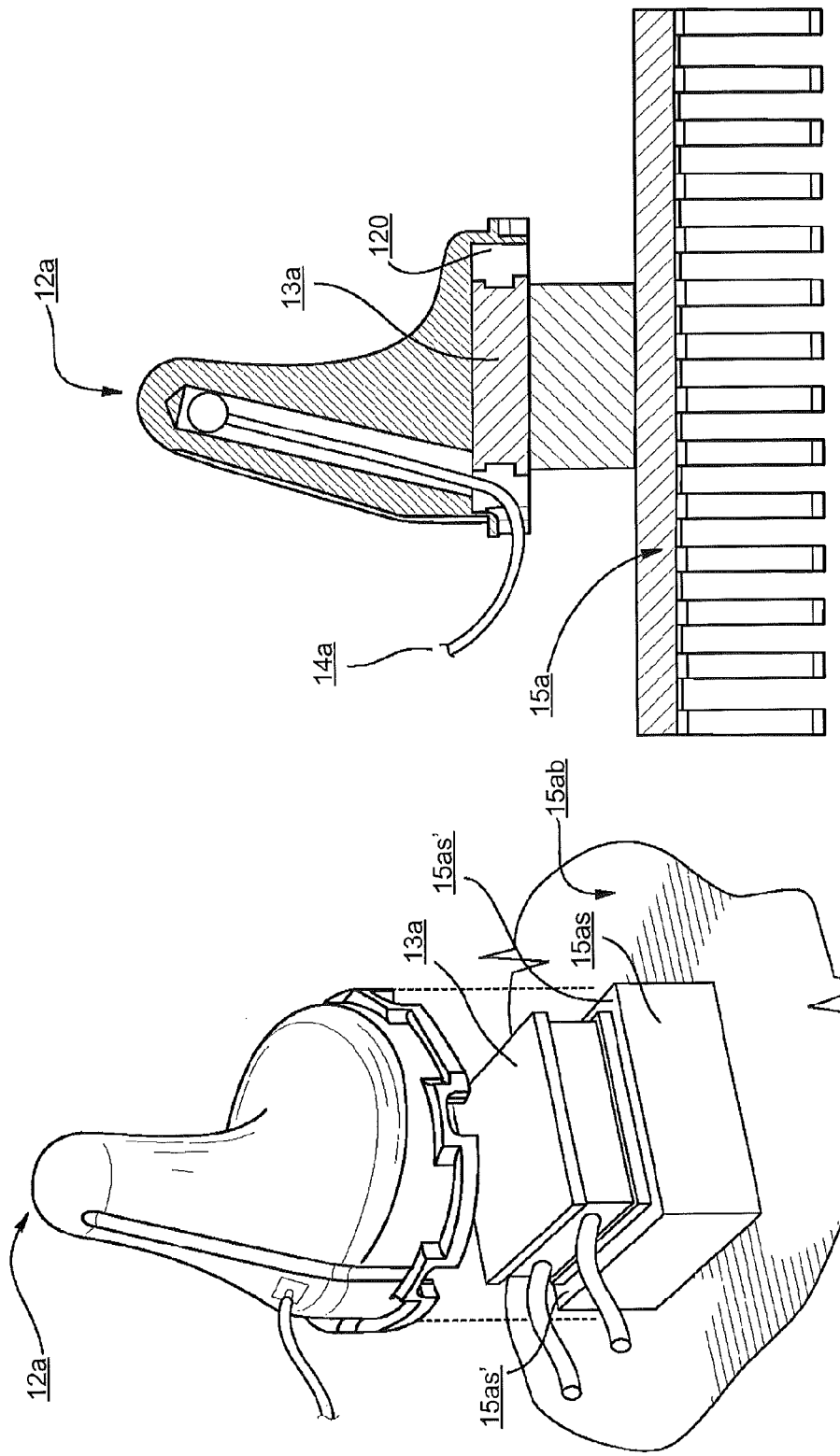

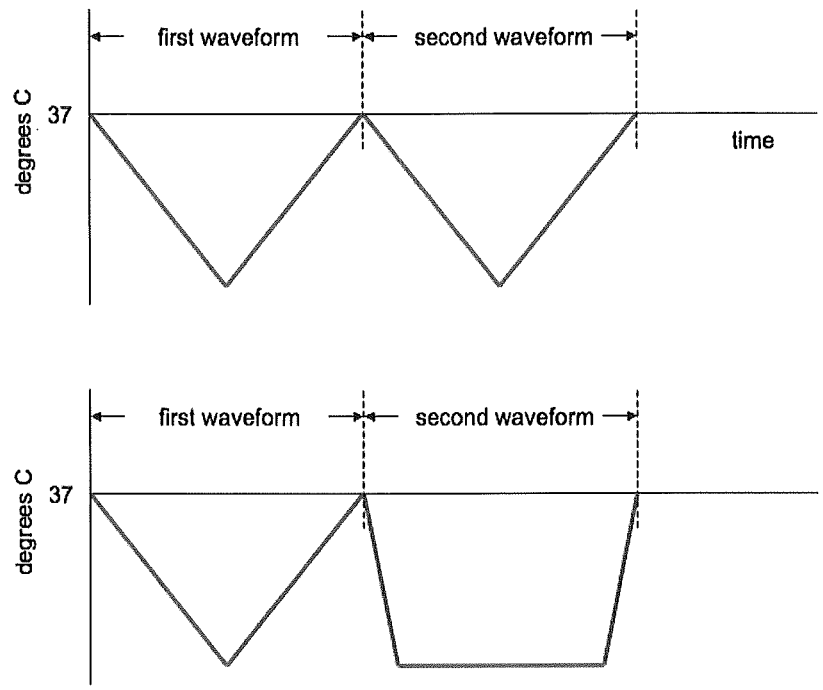
Figure 22: Example first and second waveform stimuli.
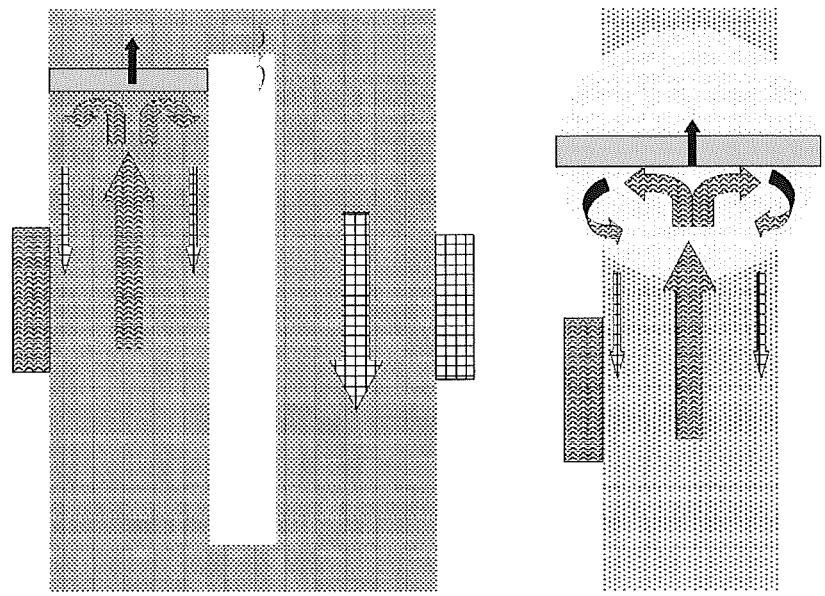
Figure 23

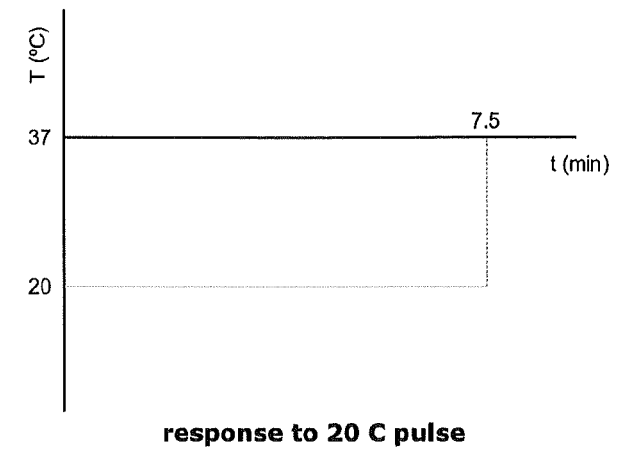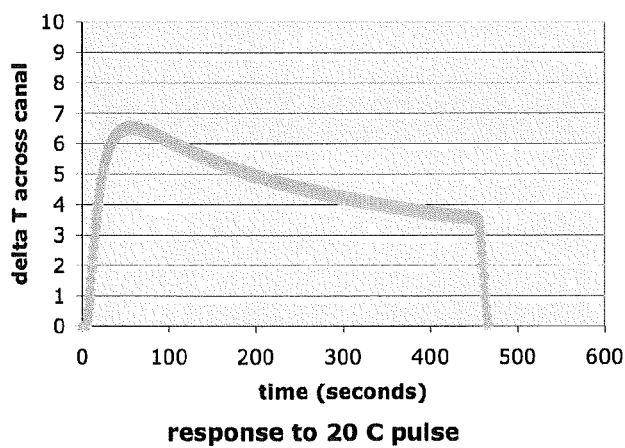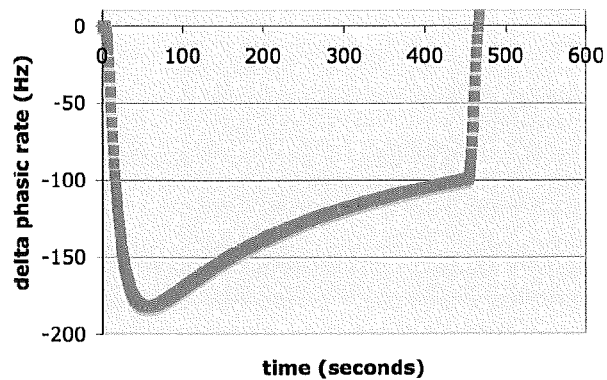
Figure 29. Single square waveform (20 °C) over 7.5 minutes

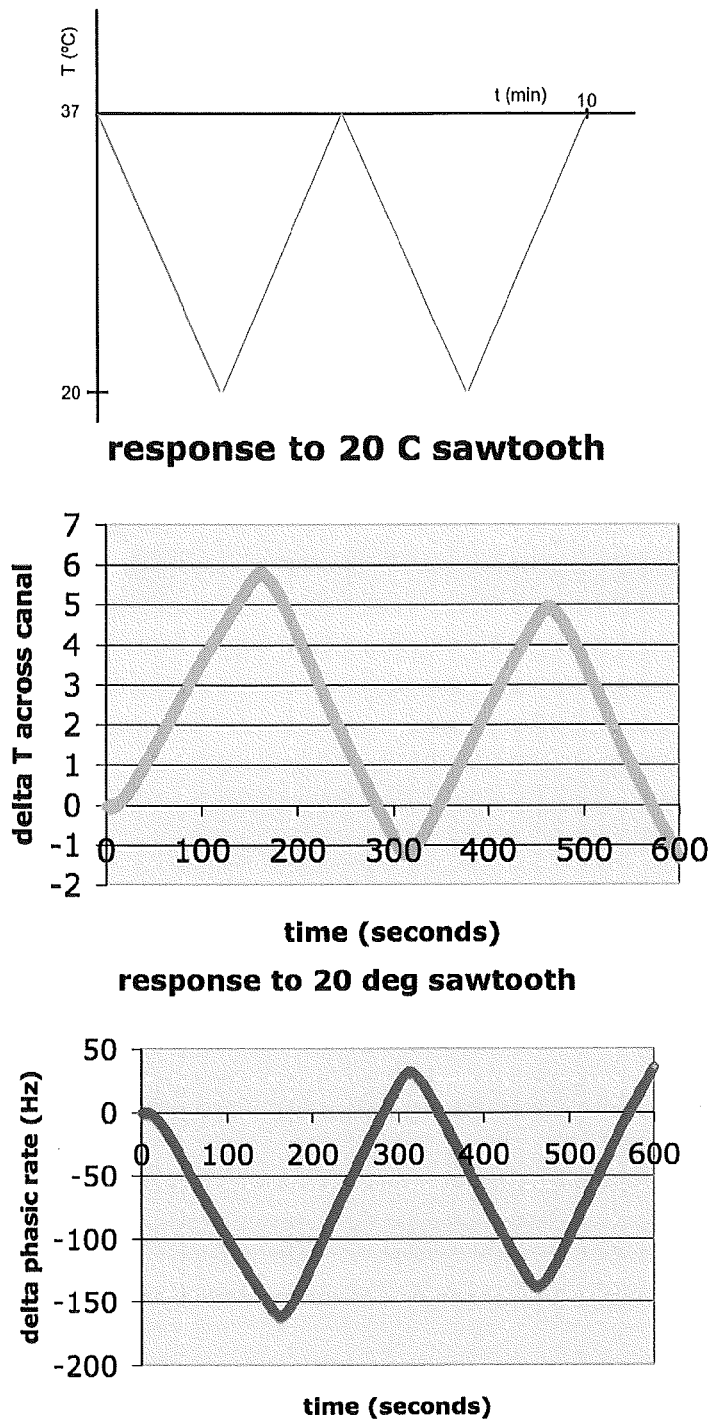
Figure 30. Two consecutive sawtooth waveforms (20 °C) over 10 minutes.

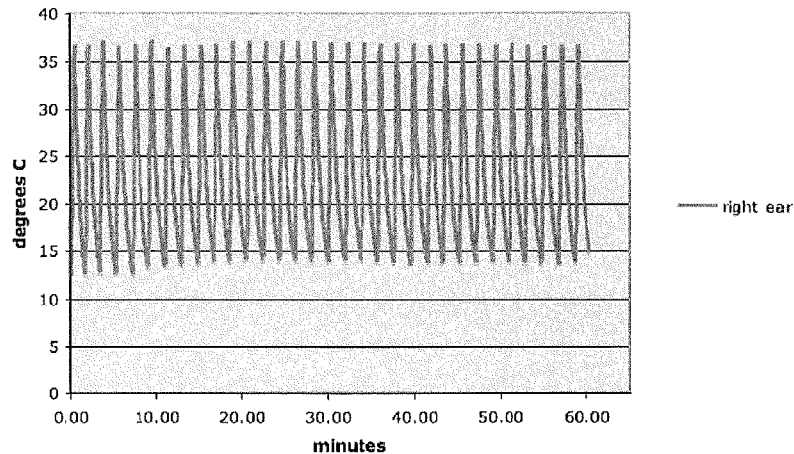
Figure 39. The CVS waveform used for rat #9 (the same waveform was used for left ear CVS)
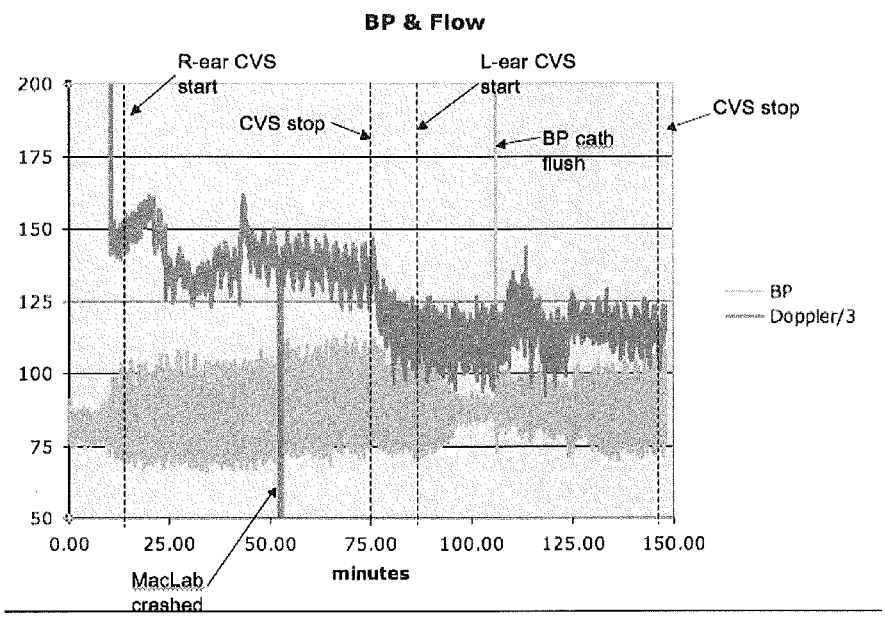
Figure 40. Raw data from rat #9 showing both the periods of right ear and left ear CVS induction.

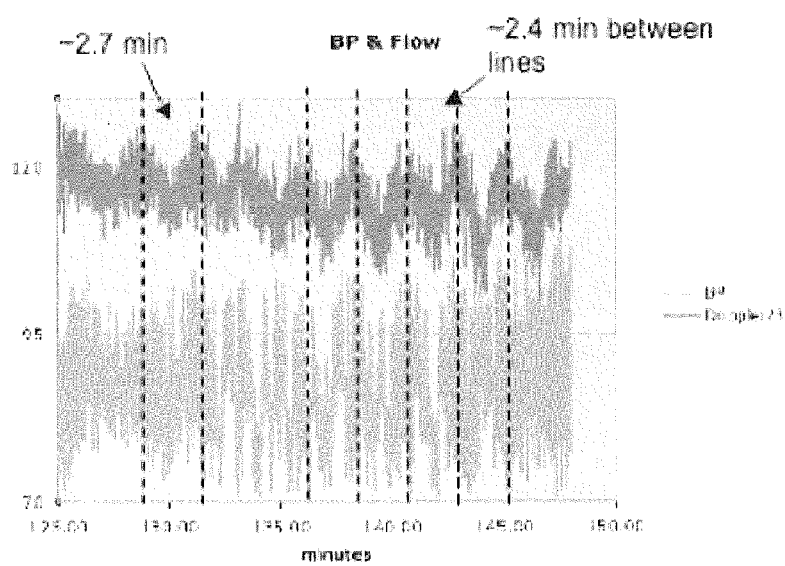
Figure 41. Raw data showing oscillations in rCBF in the right parietal region during left ear CVS
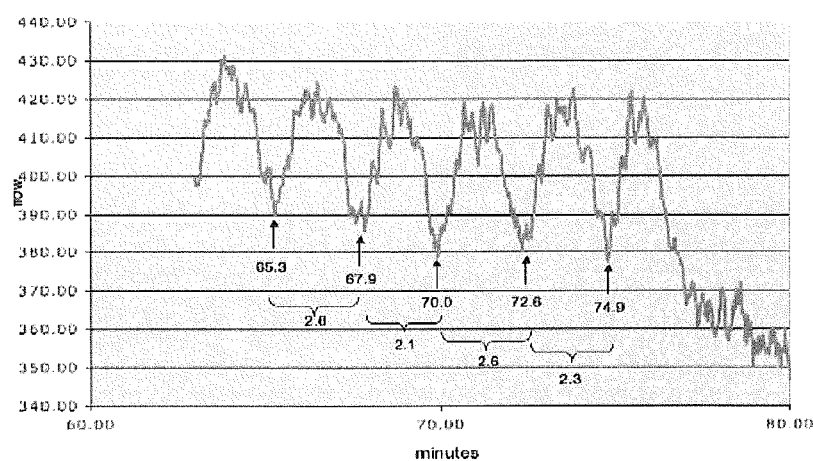
Figure 42. Nearest neighbor averaging of a sequence of oscillations in rCBF during right ear CVS

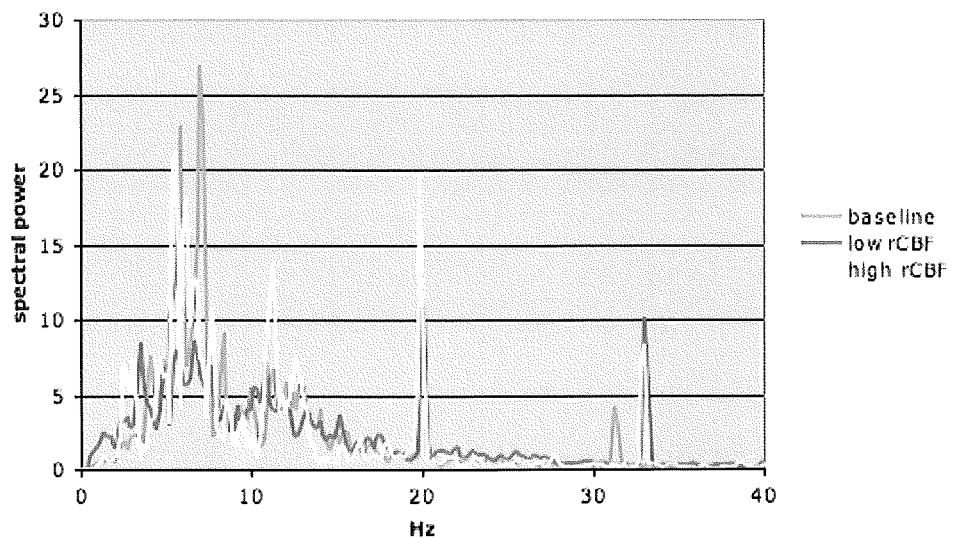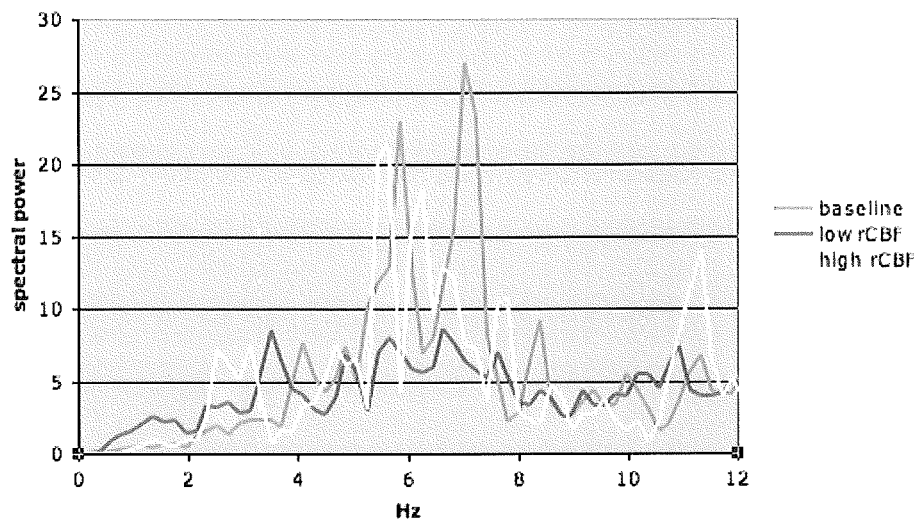
Figure 48

US 9,849,026 B2

APPARATUS AND METHODS FOR PRODUCING BRAIN ACTIVATION VIA THE VESTIBULAR SYSTEM WITH TIME-VARYING WAVEFORMS

RELATED APPLICATIONS

This application is a 35 U.S.C. §371 national phase entry of PCT Application PCT/US2011/065321, filed Dec. 16, 2011, and published in English on Jun. 21, 2012, as International Publication No. WO 2013/083098, which claims priority to U.S. Provisional Patent Application Nos. 61/424,474, filed Dec. 17, 2010; 61/498,131, filed Jun. 17, 2011; 61/497,761, filed Jun. 16, 2011; 61/424,132, filed Dec. 17, 2010; 61/498,096, filed Jun. 17, 2011; 61/424,326, filed Dec. 17, 2010; 61/498,080, filed Jun. 17, 2011; 61/498,911, filed Jun. 20, 2011 and 61/498,943, filed Jun. 20, 2011; U.S. patent application Ser. No. 12/970,312, filed Dec. 16, 2010 and Ser. No. 12/970,347, filed Dec. 16, 2010 and PCT Application Nos. PCT/US2010/060764, filed Dec. 16, 2010; the disclosure of each of which is incorporated herein by reference in its entirety.

FIELD OF THE INVENTION

The present invention concerns methods and apparatus for carrying out caloric vestibular stimulation, particularly for therapeutic purposes.

BACKGROUND OF THE INVENTION

Caloric vestibular stimulation (CVS) has been widely and safely utilized for more than a century for diagnostic purposes, particularly in the emergency room to detect brain function after trauma. CVS activates the sensory organs of the vestibular system (VS) located within the inner ear. The core elements consist of the semi-circular canals, which sense rotational motion, and the otoliths, which sense linear acceleration. Motion within the semi-circular canals is detected through motion of internal fluid (endolymph), which in turn activates hair cells that generate electrical signals, which are then transmitted via the 8th cranial nerve to the brainstem and widely throughout the cerebellum and cortical regions. In CVS, irrigation of the outer ear canal with warm or cold water changes the density of the endolymph in the semi-circular canal of the inner ear, which in turn activates the pathways noted above. Nystagmus, or the vestibulo-ocular reflex, is an easily observed result of CVS where the eyes move spontaneously, even if the patient is unconscious. See generally L. Patten, Vestibulo-ocular reflex paths, *Br. J. Ophthalmol.* 16, 257 (1932).

There have been intriguing (but largely anecdotal) reports of using CVS as a therapeutic measure. See generally L. Rogers and L. Smith, PCT Appl. Pub. No. WO 2009/020862. Survey articles document a variety of outcomes and discuss some of the mechanisms involved (Miller et al., *Acta Neuropsychiatria* 19:183-203 (2007); Been et al., *Brain Research Reviews* 56 346-36 (2007)). Squirting or blowing warm/cold water/air into a patient's ear, however, is crude, does not provide closely controlled thermal activity, and is not consistent with medical dosing.

CVS is known to activate specific brainstem, cerebellar and cortical sites, which have therapeutic potential, as demonstrated through functional imaging (Bottini et al., *Exp Brain Res* 99: 164-169 (1994); Bense et al., *Ann NY Acad Science* 1004: 440-445 (2003); Dieterich et al., *Brain,* 131, 2538-2552 (2008); *Hum Brain Mapp* (September 2009); Naito, Cortical correlates of vestibulo-ocular reflex modulation: A PET study. *Brain* 126 (2003)).

In addition, vestibular stimulation is also known to release important neurotransmitters (e.g., serotonin, acetylcholine, histamine, endorphins, vasopressin and dopamine) (MA Fu-rong et al., *Chin Med J* 120(2):120-124 (2007); Horii et al., *J. Neurophysiol.* 72, 605-611 (1994); Tabet, *Age and Aging,* 35: 336-338 (2006); Horii et al., *J Neurophysiol* 70 1822-1826 (1993); Horii et al., *Brain Research* 914: 179-184 (2001)).

In contrast to both pharmaceutical treatment and neurostimulation devices which employ electrical signals, CVS appears to have an advantage: although nystagmus habituates with repetition of CVS (Naito et al., supra (2003)), the vestibular neurological response appears not to be subject to such habituation or accommodation. (Emani-Nouri, *Acta Otolaryngologica* 76, 183-189 (1973)). In addition, CVS does not have the potential for side effects in the same manner that a pharmaceutical does. Yet, CVS has not attained wide-spread use for therapeutic purposes. Hence, there remains a need for methods to utilize caloric vestibular stimulation for therapeutic purposes.

SUMMARY OF THE INVENTION

The present invention concerns a method of administering caloric vestibular stimulation to a subject in need thereof. The method generally comprises administering said caloric vestibular stimulation (CVS) to said subject as at least a first waveform (e.g., a first time-varying waveform) stimulus. The administration may be carried out acutely or chronically.

In some embodiments, the time varying waveform is an actively controlled time varying waveform.

In some embodiments, the method further comprises the step of: administering at least a second waveform (e.g., a second time-varying waveform) stimulus after said first time-varying waveform (e.g., so that saturation of activation of the vestibular nerve by said caloric vestibular stimulation is reduced).

In some embodiments of the foregoing, each of said first and second time varying waveforms, which may be the same or different, has a duration of from 1 or 2 minutes to 10 or 20 minutes, or more, and an amplitude of from 5 to 17, 22 or 24 degrees Centigrade.

In some embodiments of the foregoing, each of said first and/or second time varying waveforms comprises a ramped leading edge.

In some embodiments of the foregoing, said first waveform is varied over time, said second waveform is varied over time, and/or said second waveform is selected, to stimulate a phasic firing rate of the vestibular nerve of about 50 to 200 Hz greater than, or less than, the corresponding tonic firing rate of said vestibular nerve.

Some embodiments of the foregoing further comprise the step of titrating or controlling said time varying waveform so that undesired side-effects of said caloric vestibular stimulation are reduced and/or efficacy of said CVS is enhanced.

In some embodiments, the time-varying waveform is administered so that saturation of vestibular nerve activation is reduced and activation of the fastigial nucleus by said vestibular nerve activation is enhanced.

In some embodiments, the subject is afflicted with Parkinson's disease, migraine headache, depression, anxiety, type II diabetes, dementia, spatial neglect, epilepsy or seizures, or post-traumatic stress disorder.

In some embodiments of the foregoing: (a) modulation of mitochondria in said subject by said activation of said fastigial nucleus is enhanced by an amount effective to treat a mitochondrial disorder in said subject; and/or (b) a neuroprotective effect of said fastigial nuclei activation is enhanced.

In some embodiments, the administering step is continued chronically. In some embodiments, the method further comprises titrating said caloric vestibular stimulation during the course of said chronically administering.

In some embodiments of the invention, a time varying thermal waveform is employed to adjust the phasic firing rate of the hair cells in the lateral SCC to a specific range of frequencies (inhibitory or excitatory) between zero and 200 Hz.

In some embodiments of the invention, the time varying thermal waveform is adjusted for a specific patient's thermal time constants to achieve control of the phasic firing rate.

In some embodiments of the invention, a spectrum of phasic firing rates is selected to enhance neuroprotective effects mediated by the fastigial nuclei.

In some embodiments of the invention, stochastic, chaotic or harmonic modulations of the phasic firing rate via a time varying waveform are used to address a medical condition. For example, a stochastic or chaotic firing rate to resolve tremor caused by synchronous firing.

In some embodiments of the invention, the caloric vestibular stimulation and/or corresponding phasic firing rate spectrum is titrated over time to improve therapeutic benefit and/or reduce undesired side effects (vertigo, localized pain). This can also involve using assessment data from EEG, fMRI, serum glucose or other blood chemistry analysis, saliva chemistry analysis, saliva chemistry analysis, cerebral blood flow, urinalysis, heart rate, heart rate variability, or other physiological assessment data, etc.

A further aspect of the invention is stimulation of the fastigial nuclei via the vestibulocochlear nerve using a time varying thermal waveform for the purpose of activating an innate neuroprotective mechanism in patients.

In some embodiments, a time-varying thermal waveform is employed that enables a range of thermomechanical distortions of the cupula in the vestibular labyrinth. (The movement of the cupula in one direction has an inhibitory effect on hair cell firing and the opposite movement has an excitatory effect.)

In some embodiments, faster or slower phasic firing of the hair cells are induced, relative to the tonic firing rate, in the lateral and/or horizontal semicircular canals, using a time varying thermal waveform.

In some embodiments, the thermal thermal waveform is chosen so as to mitigate or reduce a subjects disease symptom(s) while at the same time minimizing undesired side effects (such as nystagmus and/or vertigo).

In some embodiments, the first and/or subsequent thermal stimulus are configured to maintain a vestibular stimulation of the subject for at least four or five minutes.

In some embodiments, the vestibular stimulation for at least four or five minutes is sufficient to alter a vestibular phasic firing rate to induce nystagmus over a period of at least four or five minutes.

In some embodiments, the nystagmus is sufficient to be detected, and/or is detected, using videonystagmography and/or electronystagmography.

BRIEF DESCRIPTION OF THE DRAWINGS

The foregoing and other objects and aspects of the present invention are explained in greater detail in the drawings herein and the specification set forth below. All patent references cited herein are specifically intended to be incorporated herein by reference in their entirety.

FIGS. 2-12 are screenshots illustrating various functionalities of a controller according to some embodiments of the present invention, wherein the controller comprises an interactive touchscreen.

FIG. 2 depicts a startup screen wherein the current time is shown in the upper right-hand corner of the screen.

FIG. 3 depicts a waveform module screen wherein the user has generated a thermal waveform by drawing the desired waveform on the interactive touch screen and wherein the waveform module has identified fourteen waveform modulation points (gray diamonds).

FIG. 4 depicts a waveform module screen wherein the thermal waveform depicted in FIG. 3 has been modified by selecting the third waveform modulation point of the thermal waveform and moving it to a higher temperature.

FIG. 5 depicts a treatment module screen that enables a user to provide instructions as to how many days are to be in a treatment schedule and how many treatments may be administered per day.

FIG. 6 depicts a treatment module screen that enables a user to authorize delivery of one or more prescribed thermal waveform(s) during one or more specified time periods by touching an available treatment window (represented by a grey rectangle with a black dash in its center) and then providing instructions as to which thermal waveform(s) is/are to be delivered during that treatment window (as shown in FIGS. 7-8) and instructions as to when the treatment window is to begin and end (as shown in FIG. 9).

FIG. 7 depicts a treatment module screen that enables a user to provide instructions to apply an idealized thermal waveform to the ear canal of a patient by touching the circular selection indicator to the right of the desired waveform.

FIG. 8 depicts a treatment module screen that enables a user to provide instructions to apply the selected thermal waveform to the left or right ear canal of a patient by touching the upper or lower graph, respectively.

FIG. 9 depicts a treatment module screen that enables a user to provide instructions as to when a given treatment window is to begin and end (i.e., to provide instructions as to the window of time in which one or more prescribed thermal waveforms may be administered to a patient).

FIG. 10 depicts a treatment module screen that enables a user to modify a treatment schedule by editing and/or copying previously established treatment sessions (e.g., by changing which thermal waveform(s) are to be delivered during a given treatment session (as shown in FIGS. 7-8), by changing the start and/or end time for one or more treatment sessions (as shown in FIG. 9), by deleting one or more treatment sessions, etc.).

FIG. 11 depicts a control module screen wherein a thermal waveform delivered to the left ear canal and a thermal waveform being delivered to the right ear canal of a patient are graphically represented, with the current progress of each waveform represented by the changing of the depicted waveform from light gray to dark grey (i.e., the elapsed time is represented by the dark gray portion of each waveform and the time remaining is represented by the light gray portion of each waveform), and wherein the user may stop the treatment session by touching the "X" in the lower left-hand corner of the screen.

FIG. 12 depicts a password protection screen.

FIG. 18A is a perspective view of an earpiece according to some embodiments of the present invention.

FIG. 18B is a side view of an earpiece according to some embodiments of the present invention.

FIG. 18C is a cross-sectional view of an earpiece according to some embodiments of the present invention.

FIG. 21A is an exploded, perspective view of an earpiece, a TED and a heat sink according to some embodiments of the present invention.

FIG. 21B is an exploded, cross-sectional view of an earpiece, a TED, a spacer and a heat sink according to some embodiments of the present invention.

FIG. 22. Example first and second waveform stimuli.

FIG. 23. A schematic diagram of the horizontal semicircular canals (SCC) that is being heated on one side (wavy lines) and cooled on the other (cross-hatched), where the cupula is shown in dark grey and the arrows represents endolymph flow.

FIG. 29. Single square waveform (20° C.) over 7.5 minutes.

FIG. 30. Two consecutive sawtooth waveforms (amplitude of 20° C.) over a time of 10 minutes.

FIG. 39. The CVS waveform used for rat #9 (the same waveform was used for left ear CVS)

FIG. 40. Raw data from rat #9 showing both the periods of right ear and left ear CVS induction.

FIG. 41. Raw data showing oscillations in rCBF in the right parietal region during left ear CVS FIG. 42. Nearest neighbor averaging of a sequence of oscillations in rCBF during right ear CVS.

FIG. 48. Electroencephalograph (EEG) spectra of a rat treated with a single ear, sawtooth waveform, caloric vestibular stimulation. A zero to 12 Hz plot is above; a zero to 40 Hz plot is below.

DETAILED DESCRIPTION OF EMBODIMENTS OF THE INVENTION

Figure 1:
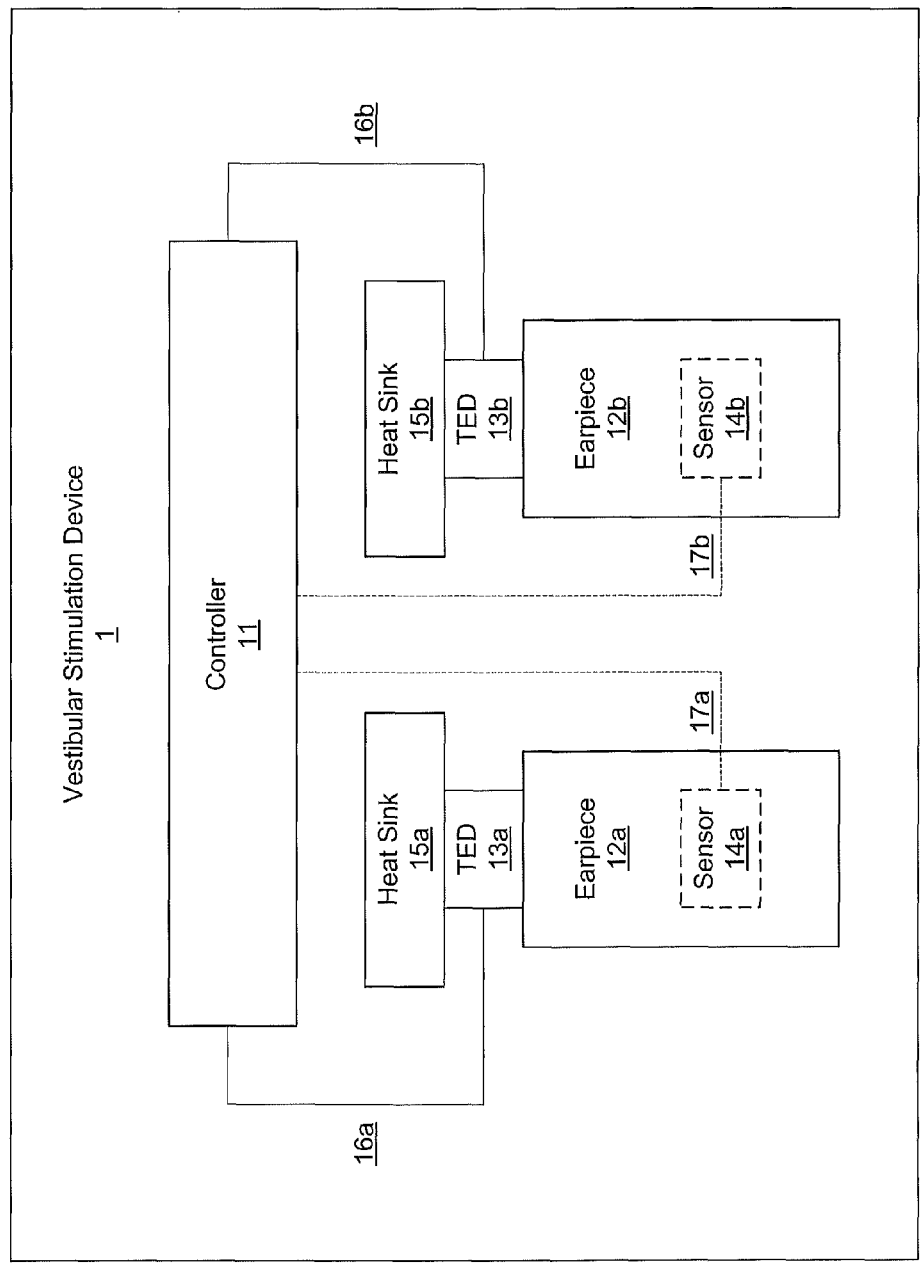
FIG. 1 is a block diagram of a vestibular stimulation device according to some embodiments of the present invention.
Figure 2:
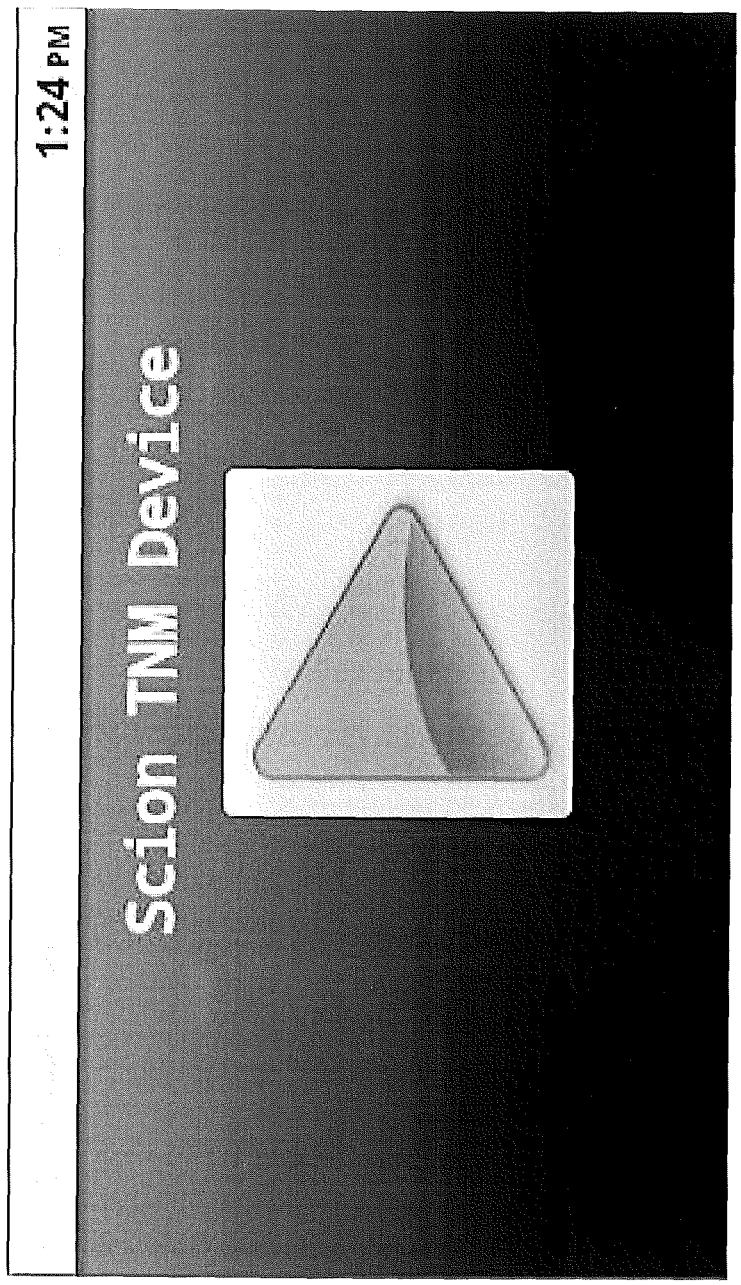

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

"About," as used herein when referring to a measurable value such as an amount or concentration (e.g., the weight percent of the active compound in the composition) and the like, is meant to encompass variations of 20%, 10%, 5%, 1%, 0.5%, or even 0.1% of the specified amount.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The present invention may be embodied as systems, methods, and/or computer program products. Accordingly, the present invention may be embodied in hardware and/or in software (including firmware, resident software, microcode, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, electromagnetic, infrared, or semiconductor system, apparatus, or device. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory, such as an SD card), and a portable compact disc read-only memory (CD-ROM).

The present invention may be described below with reference to block diagrams and/or flowchart illustrations of devices, methods and computer program products according to embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

1. DEFINITIONS

"Subject" or "patient" as used herein refers generally to human subjects or patients. The subject or patient may be male or female and may be of any suitable age, including infant, juvenile, adolescent, adult, and geriatric subjects. In some embodiments, the present invention may be used to diagnose and/or treat other mammalian subjects such as cats, dogs, monkeys, etc. for medical research or veterinary purposes.

"Actively controlled waveform" and "actively controlled, time-varying thermal waveform" as used herein refer to a thermal waveform in which the intensity and/or the directionality of the activation signal used to deliver the thermal waveform and/or the temperature of the earpiece used to deliver the thermal waveform is repeatedly adjusted (e.g., continuously adjusted or substantially continuously adjusted) during delivery of the thermal waveform. For example, the activation signal driving the TED(s) used to deliver the thermal waveform may be continuously adjusted in response to feedback data from one or more sensors (e.g., a temperature sensor configured to sense the temperature of the earpiece with which the TED(s) is/are associated). Such active control may be used to minimize errors in the delivery of a prescribed thermal waveform (e.g., by minimizing thermal drift, which may otherwise allow the patient's body temperature to adversely affect the accuracy).

"Treatment," "treat," and "treating" refer to reversing, alleviating, reducing the severity of, delaying the onset of, inhibiting the progress of, or preventing a disease or disorder as described herein, or at least one symptom of a disease or disorder as described herein (e.g., treating one or more of tremors, bradykinesia, rigidity or postural instability associated with Parkinson's disease; treating one or more of intrusive symptoms (e.g., dissociative states, flashbacks, intrusive emotions, intrusive memories, nightmares, and night terrors), avoidant symptoms (e.g., avoiding emotions, avoiding relationships, avoiding responsibility for others, avoiding situations reminiscent of the traumatic event), hyperarousal symptoms (e.g., exaggerated startle reaction, explosive outbursts, extreme vigilance, irritability, panic symptoms, sleep disturbance) associated with post-traumatic stress disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment is not limited to addressing a deficiency and may comprise providing neuroprotection, enhancing an existing attribute or positive attribute such as cognition and/or increasing cognitive reserve. Treatment may be as an adjuvant treatment as further described herein.

"Chronic treatment," "chronically treating" or the like refer to a therapeutic treatment carried out at least once per week (e.g., two or three times per week, daily, etc.) over an extended period of time. Chronic treatment typically lasts at least one to two weeks (and, in some embodiments, at least one to two months), but may last as long as required to achieve and/or maintain therapeutic efficacy for the particular condition or disorder for which the treatment is carried out (i.e., the device may be used periodically throughout the patient's life).

"Adjuvant treatment" as used herein refers to a treatment session in which the delivery of one or more thermal waveforms to the vestibular system and/or the nervous system of a patient modifies the effect(s) of one or more active agents and/or therapies. For example, the delivery of one or more thermal waveforms to the vestibular system and/or the nervous system of a patient may enhance the effectiveness of a pharmaceutical agent (by restoring the therapeutic efficacy of a drug to which the patient had previously become habituated, for example). Likewise, the delivery of one or more thermal waveforms to the vestibular system and/or the nervous system of a patient may enhance the effectiveness of counseling or psychotherapy. In some embodiments, delivery of one or more thermal waveforms to the vestibular system and/or the nervous system of a patient may reduce or eliminate the need for one or more active agents and/or therapies. Adjuvant treatments may be effectuated by delivering one or more thermal waveforms to the vestibular system and/or the nervous system of a patient prior to, currently with and/or after administration of one or more active agents and/or therapies.

"Titrate" or "titrating" as used herein with respect to caloric vestibular stimulation means that the stimulus is altered between treatment sessions to enhance the efficacy of subsequent sessions and/or reduced undesired side effects during subsequent sessions.

"Controller feedback data" as used herein refers to data that is transmitted to the controller by one or more TEDs and/or one or more sensors and is used by the controller to verify the accuracy of the thermal waveform(s) being delivered, to modulate the activation of one or more TEDs so as to deliver the appropriate thermal waveform(s) and/or to enable the controller to activate safety precautions in the event of a system failure. For example, controller feedback data may comprise data associated with the temperature of an earpiece, wherein said data is used to verify that the appropriate temperature is being delivered to the ear canal of a patient, to enable the controller to increase/decrease the activation of one or more TEDs to ensure that the appropriate temperature is delivered to the ear canal of a patient and/or to trigger a system shutdown if the temperature of the earpiece surpasses a certain threshold (e.g., below about 10° C. or above about 50° C.). Likewise, controller feedback data may comprise data associated with the temperature of a heat sink that is thermally coupled to one or more TEDs, wherein said data is used to trigger a system shutdown if the temperature of the heat sink surpasses a certain threshold (e.g., below about 5° C. or above about 50° C.).

"Data associated with the delivery of one or more thermal waveforms" as used herein refers to information associated with the delivery of one or more thermal waveforms and may include, but is not limited to, data associated with the target time/temperature parameters of the thermal waveform(s), the time/temperature parameters of the thermal waveform(s) delivered; the date/time of delivery of the thermal waveform(s), the temperature of the patient's ear canal(s) at various time points before, during and/or after delivery of the thermal waveform(s); the temperature of the patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from the ear canal to the inner ear); reaction time (i.e., how long it took for the patient to react to the thermal waveform(s)); effectiveness of the thermal waveform(s) (e.g., whether and to what extent symptoms were relieved, whether the thermal waveform(s) enhanced the effectiveness of another agent/therapy, etc.); stability of the treatment (i.e., how long the effects of the treatment lasted); instability of the treatment (i.e., which condition(s) and/or symptom(s) returned and when did it/they return); the presence or absence of comorbid disorders, injuries and/or diseases; disorder, injury and/or disease modulation(s) and/or other modification(s) that occurred as a result of treatment; the cognitive effect(s) of one or more thermal waveforms; patient compliance (e.g., whether the patient initiated delivery at the prescribed time, whether the patient completed the prescribed treatment session, whether the earpiece(s) remained properly fitted in the patient's ear canal(s) for the duration of the treatment session, etc.); the mood of the patient before, during and/or after his/her treatment session(s) (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)) and comments the patient made about his/her treatment session(s) (e.g., comments made to a physician, submitted in response to an automated survey and/or recorded in a treatment diary). In some embodiments, data associated with the delivery of one or more thermal waveforms comprises controller feedback data, patient feedback data and/or physician feedback data. In some embodiments, data associated with the delivery of one or more thermal waveforms comprises, consists essentially of or consists of data associated with the precise time/temperature parameters of the thermal waveform(s) delivered to the patient and a subjective measure of efficacy (e.g., a patient-reported pain score).

"Data associated with the fit of the earpiece(s)" may include, but is not limited to, data associated with the impedance between an earpiece inserted into the ear canal of a patient and an electrode affixed to a second location on/in said patient's body (e.g., an electrode placed in or adjacent to the patient's other ear canal), data associated with the rate at which the ear canal and/or the inner ear cooled in response to a cooling stimulus (e.g., data from a temperature sensor, such as thermistor, that monitors how quickly the ear canal and/or the inner ear cools in response to a cooling waveform), data associated with the rate at which the ear canal and/or the inner ear warmed in response to a warming stimulus (e.g., data from a temperature sensor, such as a thermistor, that monitors how quickly the ear canal and/or the inner ear warms in response to a warming waveform) and patient comments regarding the subjective fit of the earpiece(s). In some embodiments, data associated with the fit of the earpiece(s) comprises, consists essentially or consists of data associated with the impedance between an earpiece inserted into the right ear canal of a patient and an earpiece inserted into the left ear canal of said patient.

"Idealized thermal waveform" and "idealized waveform" as used herein refer to a thermal waveform that has been indicated and/or approved for use in the treatment of one or more diseases/disorders/injuries and/or for use in the provision of neuroprotection, enhanced cognition and/or increased cognitive reserve. For example, a thermal waveform may be indicated for use in the treatment of migraines if it has effectively treated migraines in the past or if it belongs to a class of thermal waveforms that are known to treat migraines. Likewise, a thermal waveform may be approved for use in the treatment of a given disorder if it has received regulatory approval (e.g. FDA approval) for such use, or if it belongs to a class of thermal waveforms that have been approved for the treatment of that disorder. An idealized thermal waveform may be indicated/approved for use in the treatment of multiple diseases/disorders/injuries.

"Patient information" as used herein refers to data associated with one or more patients. Patient information may comprise, but is not limited to, information related to a patient's identity, a patient's cognitive abilities, a patient's medical history, a patient's current symptoms (if any), a patient's present diagnosis (if any), a patient's current prescriptions (if any) and data associated with the delivery of one or more thermal waveforms to the vestibular system and/or the nervous system of a patient.

"Patient feedback data" as used herein refers to data associated with patient feedback regarding the delivery of one or more thermal waveforms. Patient feedback data may comprise, but is not limited to, a patient's evaluation of their pain level before, during and/or after delivery of the thermal waveform(s) (e.g., patient-reported pain scores given before, during and after a treatment session) and patient comments (e.g., comments regarding a patient's opinion as to the efficacy of a given waveform or the effect(s) of certain waveform modifications, etc.).

"Physician feedback data" as used herein refers to data associated with physician feedback regarding the delivery of one or more thermal waveforms. Physician feedback data may comprise, but is not limited to, patient information from the patient history database of one or more physician control devices and comments from one or more physicians (e.g., comments regarding a physician's opinion as to the efficacy of a given waveform or the effect(s) of certain waveform modifications, etc.).

"Prescription" and "prescription protocol" as used herein refer to a set of instructions and/or limitations associated with stimulation of the vestibular system and/or the nervous system of a patient. In some embodiments, a prescription comprises, consists essentially of or consists of a set of instructions for delivering of one or more thermal waveforms (e.g., one or more actively controlled, time-varying thermal waveforms) to the vestibular system and/or the nervous system of a patient (e.g., by warming and/or cooling an earpiece positioned in the ear canal of the patient). A prescription may comprise a set of instructions for delivering one or more thermal waveforms to the left vestibular system of a patient (by delivering one or more thermal waveforms to the left ear canal of the patient) and/or a set of instructions for delivering one or more thermal waveforms to the right vestibular system of a patient (by delivering one or more thermal waveforms to the left ear canal of the patient) (i.e., one prescription may comprise instructions for stimulating both the right and left vestibular systems). A prescription may comprise any suitable instructions and/or limitations, including, but not limited to, the parameters of the waveform(s) to be delivered to the patient, the number and frequency of treatment sessions (e.g., X treatment sessions over Y time period), a limitation as to how many treatment sessions may be administered during a given time period (e.g., no more than X treatment sessions within Y time period), instructions as to which thermal waveform(s) will be administered during a given treatment session (and in what order they are to be administered), instructions as to which vestibular system will receive a given waveform (e.g., right, left or both) and an expiration date. In some embodiments, a prescription comprises instructions for delivering a placebo (i.e., for fooling a patient into believing one or more thermal waveforms has been delivered even though no such deliver has occurred). In some embodiments, the prescription is generated by a physician. Any conventional security means may be provided to prevent unauthorized modification of the prescription (e.g., the prescription may be password protected, with only the prescribing physician having knowledge of and/or access to the password).

"Registry" as used herein refers to a device configured to receive, store and/or transmit data from/to a plurality of vestibular stimulation devices and/or other registries. In some embodiments, the registry is configured to receive, store and/or transmit data from/to one or more devices located within a specified geographical region (e.g., the northeastern United States, the southeastern United States, the United States, North America, Europe, Japan, China, etc.). For example, a registry may be configured to receive and/or store one or more thermal waveforms (i.e., to receive/store data associated with the parameters, indications and/or approvals of one or more thermal waveforms) from one or more vestibular stimulation devices and/or from one or more registries located in the United States. Likewise, a registry may be configured to transmit data associated with the parameters, indications and/or approvals of one or more thermal waveforms to one or more vestibular stimulation devices and/or to one or more registries located in the United States.

As discussed further below, an object of certain embodiments of this invention is to provide methods and apparatus that allow for the activation of innate protective systems in the body. Specifically, the ability for chronic application (that is, over a period of days, weeks, months or perhaps years) of titrated thermal stimulation of the lateral/horizontal semicircular canal (it should be noted that other canals and the otolith structures may also be activated to varying degrees) so as to enable a wide variety of time-varying movements of the cupula, thus causing a variety of time-varying (excitatory and inhibitory) activations of the hair cells, which then create phasic firing of the 8th cranial nerve.

2. APPARATUS

As noted above, the present invention provides a vestibular stimulation device for delivering one or more thermal waveforms to the vestibular system and/or the nervous system of a patient. Thus, a caloric vestibular stimulation apparatus capable of delivering waveform stimulus is preferably used to carry out the present invention. Suitable examples are illustrated in U.S. patent application Ser. No. 12/970,312, filed Dec. 16, 2010 (also published as Rogers and Smith, PCT Application WO 2011/075573, on Jun. 23, 2011) and U.S. patent application Ser. No. 12/970,347, filed Dec. 16, 2010, (also published as Smith and Rogers, PCT Application WO 2011/075574, on Jun. 23, 2011), the disclosures of which are incorporated by reference herein in their entirety In some embodiments, the vestibular stimulation device is configured to deliver one or more actively controlled, time-varying thermal waveforms to the vestibular system and/or the nervous system of a patient.

In some embodiments, the vestibular stimulation device is configured to generate a prescription comprising a set of instructions for delivering one or more thermal waveforms to the vestibular system and/or the nervous system of a patient and to deliver the prescribed thermal waveform(s) to the vestibular system and/or the nervous system of said patient.

In some embodiments, the vestibular stimulation device comprises, consists essentially of or consists of an earpiece, a TED and a controller, wherein said TED is thermally coupled to said earpiece and wherein said controller is operatively connected to said TED. The controller may be configured to activate said TED to deliver one or more thermal waveforms to the vestibular system and/or the nervous system of a patient (i.e., to activate the TED such that the earpiece is warmed and/or cooled so as to deliver the thermal waveform(s) to the vestibular system and/or the nervous system of the patient). In some embodiments, the controller is configured to generate a prescription comprising a set of instructions for delivering one or more thermal waveforms to the vestibular system and/or the nervous system of a patient and to activate the TED to deliver the prescribed thermal waveform(s).

In some embodiments, the vestibular stimulation device comprises, consists essentially of or consists of an earpiece, a plurality of TEDs and a controller, wherein each of said plurality of TEDs is thermally coupled to said earpiece and wherein said controller is operatively connected to each of said plurality of TEDs. The controller may be configured to selectively and separately activate each of said plurality of TEDs to deliver one or more thermal waveforms to the vestibular system and/or the nervous system of a patient (i.e., to activate one or more of the TEDs such that the earpiece is warmed and/or cooled so as to deliver the thermal waveform(s) to the vestibular system and/or the nervous system of the patient). In some embodiments, the controller is configured to generate a prescription comprising a set of instructions for delivering one or more thermal waveforms to the vestibular system and/or the nervous system of a patient and to activate the TEDs to deliver the prescribed thermal waveform(s).

In some embodiments, the vestibular stimulation device comprises, consists essentially of or consists of a pair of earpieces, a pair of TEDs and a controller, wherein one earpiece is configured so as to be insertable into the left ear canal of a patient and the other earpiece is configured so as to be insertable into the right canal of the patient, wherein one TED is thermally coupled to each earpiece and wherein said controller is operatively connected to each TED. The controller may be configured to selectively and separately activate each of said TEDs to deliver one or more thermal waveforms to the vestibular system and/or the nervous system of the patient. In some embodiments, the controller is configured to generate a prescription comprising a set of instructions for delivering one or more thermal waveforms to the vestibular system and/or the nervous system of the patient and to activate the TEDs to deliver the prescribed thermal waveform(s).

In some embodiments, the vestibular stimulation device comprises, consists essentially of or consists of a pair of earpieces, a plurality of TEDs and a controller, wherein one earpiece is configured so as to be insertable into the left ear canal of a patient and the other earpiece is configured so as to be insertable into the right canal of the patient, wherein at least one of said plurality of TEDs is thermally coupled to each earpiece and wherein said controller is operatively connected to each TED. The controller may be configured to selectively and separately activate each of said TEDs to deliver one or more thermal waveforms to the vestibular system and/or the nervous system of the patient. In some embodiments, the controller is configured to generate a prescription comprising a set of instructions for delivering one or more thermal waveforms to the vestibular system and/or the nervous system of the patient and to activate the TEDs to deliver the prescribed thermal waveform(s).

The vestibular stimulation device may comprise one or more heat sinks. In some embodiments, at least one heat sink is thermally coupled to each earpiece. In some embodiments, each TED thermally coupled to an earpiece is thermally coupled between the earpiece and at least one heat sink.

The vestibular stimulation device may comprise one or more sensors. In some embodiments, the sensor(s) is/are configured to provide feedback data to the controller. In some such embodiments, the controller is configured (e.g., with computer instructions (i.e., software)) to adjust one or more attributes of TED activation (e.g., magnitude, duration, wave pattern, etc.) in response to feedback data received from the sensor(s) with which it is associated. For example, the vestibular stimulation device may be configured such that, during delivery of a thermal waveform, the controller activates the TED(s) in a continuous or substantially continuous manner and repeatedly, continuously or substantially continuously adjusts one or more attributes of TED activation in response to feedback data received from one or more sensors (e.g., a temperature sensor configured to provide feedback data associated with the temperature of the ear canal of a patient).

The vestibular stimulation device may comprise a headband. In some embodiments, the headband is configured to position the earpiece(s) in the ear canal(s) of a patient.

As shown in FIG. 1, in some embodiments, the vestibular stimulation device 1 comprises a controller 11, a pair of earpieces 12a, 12b, a pair of TEDs 13a, 13b and a pair of heat sinks 15a, 15b, wherein one TED 13a is thermally connected between one heat sink 15a and an earpiece 12a that is configured so as to be insertable into the left ear canal of a patient, wherein the other TED 13b is thermally connected between the a heat sink 15b and an earpiece 12b that is configured so as to be insertable into the right ear canal of a patient and wherein the controller 11 is operatively connected to each of the TEDs 13a, 13b by a thermal stimulation conductive line 16a, 16b. In some such embodiments, each earpiece 12a, 12b is operatively connected to a sensor 14a, 14b (e.g., each earpiece may be thermally connected to a temperature sensor that is configured to detect the temperature of the earpiece), and each of the sensors 14a, 14b is operatively connected to the controller 11 by a wireless connection 17a, 17b (using a radiofrequency transceiver or a Bluetooth connection, for example).

A. Controller

Any suitable controller can be used to carry out the present invention, including, but not limited to, those described in U.S. Patent Publication Nos. 2010/0198204 and 2010/0198282; in U.S. patent application Ser. Nos. 12/970, 312 and 12/970,347 and in U.S. Provisional Application Nos. 61/497,761, the disclosure of each of which is incorporated herein by reference in its entirety.

The controller may be configured to activate at least one TED. In some embodiments, the controller is configured to activate at least one TED to deliver one or more thermal waveforms to the vestibular system and/or the nervous system of a patient (e.g., by heating and/or cooling the earpiece(s) that is/are thermally coupled to the TED. For example, the controller may be configured to activate the TED(s) based upon a prescription comprising a set of instructions for delivering one or more thermal waveforms to the vestibular system and/or the nervous system of a patient (i.e., the controller may be configured to activate the TED(s) so as to deliver the prescribed thermal waveform(s) to the vestibular system and/or the nervous system of the patient).

The controller may be configured to selectively and separately activate a plurality of TEDs. For example, the controller may be configured to selectively and separately activate the TED(s) thermally coupled to an earpiece inserted into the left ear canal of a patient and the TED(s) thermally coupled to an earpiece inserted into the right ear canal of a patient (e.g., to deliver a thermal waveform only to the left ear canal of the patient, to deliver a thermal waveform only to right ear canal of the patient or to simultaneously deliver different thermal waveforms to the left and right ear canals of the patient). Likewise, the controller may be configured to separately activate a plurality of TEDs thermally coupled to a single earpiece.

The controller may be configured to activate the TED(s) in any suitable manner, including, but not limited to, activation with direct current and/or electrical pulses. In some embodiments, the controller is configured to activate the TED(s) in a continuous or substantially continuous manner, adjusting one or more parameters of TED activation (e.g., magnitude, duration, pulse width, etc.) to deliver the desired thermal stimulus. For example, the controller may be configured such that it continuously or substantially continuously activates each of the TEDs with which it is operatively connected and delivers different thermal stimuli by modulating the type and/or level of activation applied to each TED.

The controller may be configured to activate the TED(s) to deliver any suitable thermal waveform or combination of thermal waveforms, including, but not limited to, those described in U.S. Provisional Patent Application Nos. 61/424,132, 61/498,096, 61/424,326, 61/498,080, 61/498,911 and 61/498,943, the disclosure of each of which is incorporated herein by reference in its entirety. In some embodiments, the controller is configured to activate the TED(s) to deliver one or more actively controlled, time-varying thermal waveforms to the vestibular system and/or the nervous system of a patient.

The controller may also be configured to activate the TED(s) to deliver a constant thermal stimulus to the ear canal(s) of a patient. For example, the controller may be configured to activate the TED(s) so as to maintain the temperature of a patient's ear canal at a target temperature (e.g., to hold a patient's right canal at 20° C. while a thermal waveform is delivered to the patient's left canal).

The controller may likewise be configured to deliver one or more placebo waveforms (i.e., to fool a patient into believing one or more thermal waveforms has been delivered even though no such delivery has occurred).

In some embodiments, the controller is operatively connected to at least one TED via a thermal stimulation conductive line. In those embodiments wherein the controller is operatively connected to a plurality of TEDs, the controller may be operatively connected to each TED via a separate thermal stimulation conductive line. In some such embodiments, each of the plurality of separate thermal stimulation conductive lines is bundled together into one or more thermal stimulation leads (e.g., the thermal stimulation conductive lines connected to the TED(s) thermally coupled to the right earpiece may be bundled separately from the thermal stimulation conductive lines connected to the TED(s) thermally coupled to the left earpiece). In some such embodiments, each thermal stimulation lead is connected to the controller via a lead interface (e.g., one or more thermal stimulation leads may be connected to the controller using an 18-pin connector).

In some embodiments, the controller is operatively connected to at least one TED via a wireless connection (using a radiofrequency transceiver or a Bluetooth connection, for example).

The controller may be configured to receive and/or transmit any suitable data, including, but not limited to, data associated with the parameters, indications and/or approvals of one or more thermal waveforms, data associated with one or more prescriptions, controller feedback data, data associated with the delivery of one or more thermal waveforms, data associated with the fit of one or more earpieces, physician feedback data and/or patient information.

The controller may be configured to receive and/or transmit data from/to various devices, including, but not limited to, a registry (e.g., a registry comprising data received and/or retrieved from a plurality of vestibular stimulation devices), a TED, a sensor and/or a portable memory device (e.g., an SD memory card). In some embodiments, the controller is configured to receive data associated with the parameters, indications and/or approvals of one or more thermal waveforms (e.g., idealized thermal waveforms) from a registry and/or a portable memory device (e.g., an SD memory card); to receive one or more prescriptions from a registry and/or a portable memory device (e.g., an SD memory card); to receive controller feedback data from one or more TEDs and/or one or more sensors; to receive data associated with the delivery of one or more thermal waveforms (e.g., idealized thermal waveforms) from one or more TEDs and/or one or more sensors; to transmit data associated with the delivery of one or more thermal waveforms (e.g., idealized thermal waveforms) to a registry and/or a portable memory device (e.g., an SD memory card); to transmit patient feedback data to a registry and/or a portable memory device (e.g., an SD memory card) and/or to transmit patient information to a registry and/or a portable memory device (e.g., an SD memory card).

The controller may be configured to receive and/or transmit data over any suitable wired or wireless communications channel, including, but not limited to, a LAN, the Internet, a public telephone switching network, Bluetooth, WLAN and the like.

In some embodiments, the controller comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the controller).

The controller's memory may comprise any suitable software and/or data, including, but not limited to, an operating system, applications, data and input/output (I/O) drivers.

As will be appreciated by one of skill in the art, the controller may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the controller may comprise any suitable application, including, but not limited to, one or more programs configured to implement one or more of the various features of the present invention. For example, the controller may comprise a waveform module that enables a user to generate and/or modify the parameters, indications and/or approvals of one or more thermal waveforms; a treatment module that enables a user to generate, modify, update and/or extend a prescription comprising a set of instructions for delivering one or more thermal waveforms to the vestibular system and/or the nervous system of a patient; a control module configured to activate one or more TEDs; a network module configured to receive and/or transmit data; a GUI module configured to display information and/or accept user input; a feedback module configured to receive, transmit, and/or analyze controller feedback data, data associated with the delivery of one or more thermal waveforms, data associated with the fit of one or more earpieces, physician feedback data and/or patient information; an alert generation module configured to generate one or more alert messages; a tone generation module configured to produce one or more audible tones; a visual indicator module configured to produce one or more visual indicators; an impedance module configured to detect and/or monitor the impedance between an earpiece inserted into the ear canal of a patient and an electrode affixed to a second location on/in said patient's body, a security module configured to prevent unauthorized use of the controller and/or a safety module configured to deactivate the controller in the event of a system malfunction and/or failure. In some embodiments, two or more of the aforementioned modules are combined to form a single module configured to carry out the function(s) of each of the individual modules (e.g., the controller may comprise a waveform-treatment module that enables a user to generate and/or modify one or more thermal waveforms and to generate, modify, update and/or extend a prescription). In some embodiments, one of the aforementioned modules is split into two or more distinct modules (e.g., the controller may comprise a waveform generation module that enables a user to generate the parameters, indications and/or approvals of one or more thermal waveforms and a waveform update module that enables a user to modify the parameters, indications and/or approvals of one or more thermal waveforms). In some embodiments, one or more of the functions described below with respect to one of the modules described below is performed by one of the other modules described below (e.g., the control module, rather than the feedback module, may be configured to receive/analyze controller feedback data).

Waveform Module.

In some embodiments, the controller comprises a waveform module whereby a user may generate and/or modify the parameters, indications and/or approvals of one or more thermal waveforms.

In some embodiments, the waveform module comprises software that enables a user to generate and/or modify the parameters of one or more thermal waveforms by point-to-point design and/or by utilizing mathematical functions. For example, the waveform module may comprise software that enables a user to generate and/or modify the parameters, indications and/or approvals of a thermal waveform by selecting/altering one or more parameters, including, but not limited to, shape, frequency, amplitude and duration. In some embodiments, the waveform module enables a user to retrieve/select a thermal waveform from a database and then modify the parameters of that thermal waveform to generate a new thermal waveform.

Figure 3:
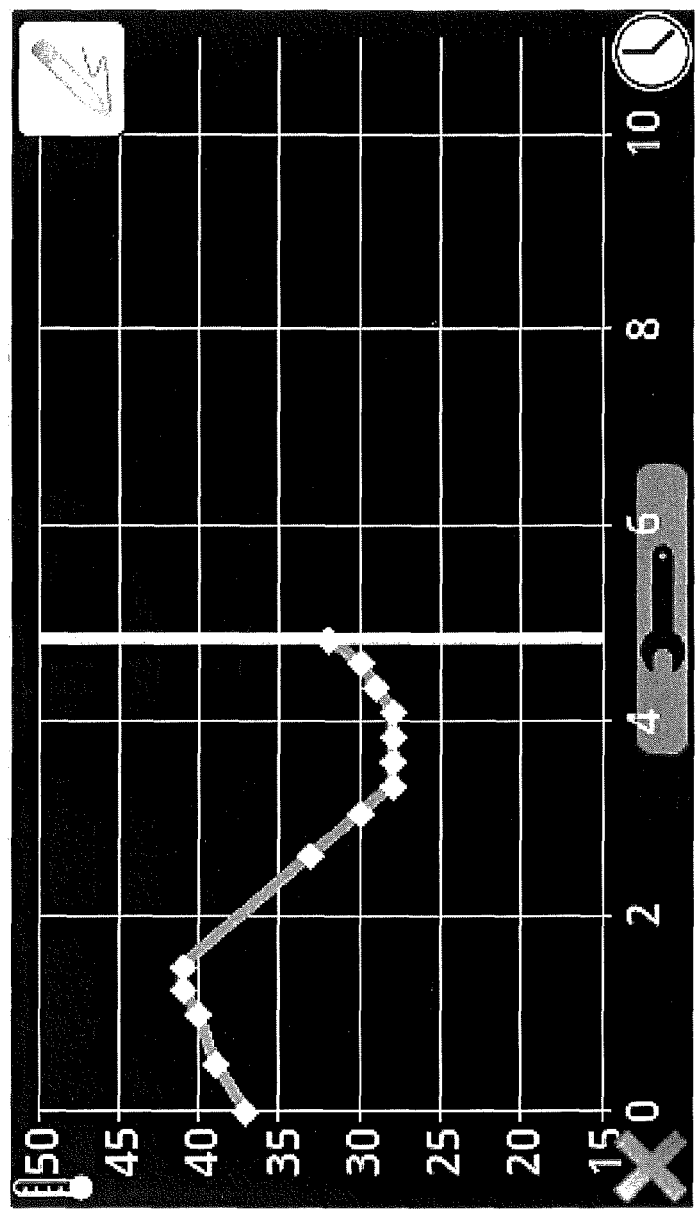
Figure 4:
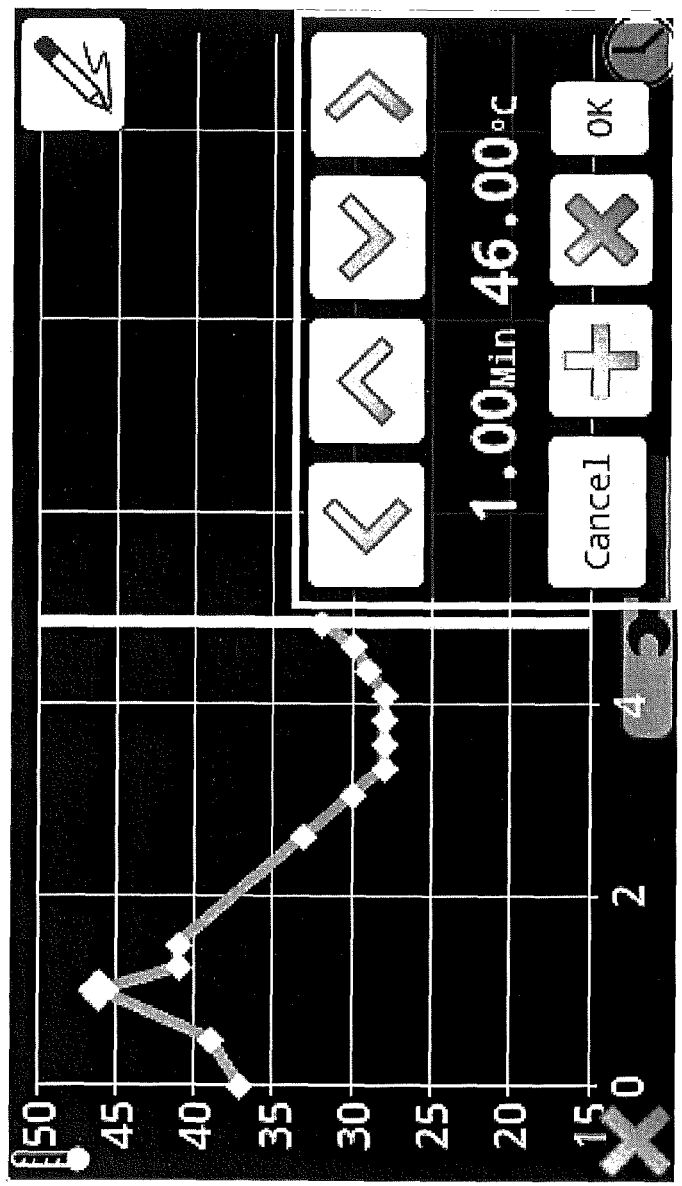

In some embodiments, the waveform module comprises software that enables a user to generate and/or modify the parameters, indications and/or approvals of one or more thermal waveforms using an interactive touch screen. For example, the waveform module may comprise software that enables a user to generate the parameters of a thermal waveform by drawing the desired waveform on an interactive touch screen (FIG. 3). Similarly, the waveform module may enable a user to modify the parameters of a thermal waveform by highlighting one or more points on the waveform and moving the point(s) to a new location (e.g., a higher/lower temperature) (FIG. 4).

In some embodiments, the waveform module comprises software that automatically adjusts the parameters of the thermal waveform(s) created by a user to account for system limitations. For example, the waveform module may comprise software that automatically adjusts the slope of a thermal waveform in accordance with the minimum/maximum temperature and/or the rate of temperature change that is achievable using a particular combination of earpiece(s), TED(s), etc. That is, the waveform module may comprise software that prevents a user from generating parameters for a thermal waveform that cannot be delivered because of system limitations.

In some embodiments, the waveform module comprises software that enables a user to protect one or more thermal waveforms (i.e., to prevent one or more users from modifying the parameters, indications and/or approvals of the thermal waveform(s) and/or from deleting the thermal waveform(s) from a waveform database). For example, the waveform module may comprise software that enables a user to protect one or more idealized thermal waveforms (e.g., by requiring users to enter a specified password prior to modifying and/or deleting the idealized thermal waveform(s)).

In some embodiments, the waveform module comprises software that enables a user to remove the protected status from one or more thermal waveforms. For example, the waveform module may comprise software that enables a user to remove the protected status from one or more idealized thermal waveforms (e.g., by entering the appropriate password).

In some embodiments, the waveform module is configured to automatically generate and/or modify the parameters, indications and/or approvals of one or more thermal waveforms (e.g., idealized thermal waveforms) in response to data received from one or more devices/modules. For example, the waveform module may be configured to automatically update one or more thermal waveforms responsive to data received from one or more TEDs and/or one or more sensors.

The waveform module may be configured to retrieve the parameters, indications and/or approvals of one or more thermal waveforms from any suitable database, including, but not limited to, a waveform database residing in the controller, a waveform database residing in a registry and/or a waveform database residing in a portable memory device (e.g., an SD memory card).

Waveform parameters, indications and/or approvals generated and/or modified by the waveform module may be stored in a database. In some embodiments, the generated/modified parameters, indications and/or approvals are stored in a waveform database comprising data associated with the parameters, indications and/or approvals of one or more thermal waveforms (e.g., idealized thermal waveforms). For example, the generated/modified waveform parameters, indications and/or approvals may be stored in a waveform database residing in the controller, a waveform database residing in a registry and/or a waveform database residing in a portable memory device (e.g., an SD memory card).

Treatment Module.

In some embodiments, the controller comprises a treatment module whereby a user (e.g., a physician) may generate, modify, update and/or extend a prescription. For example, the treatment module may enable a user to generate, modify, update and/or extend a prescription comprising a set of instructions for delivering one or more thermal waveforms to the vestibular system and/or the nervous system of a patient.

Figure 5:
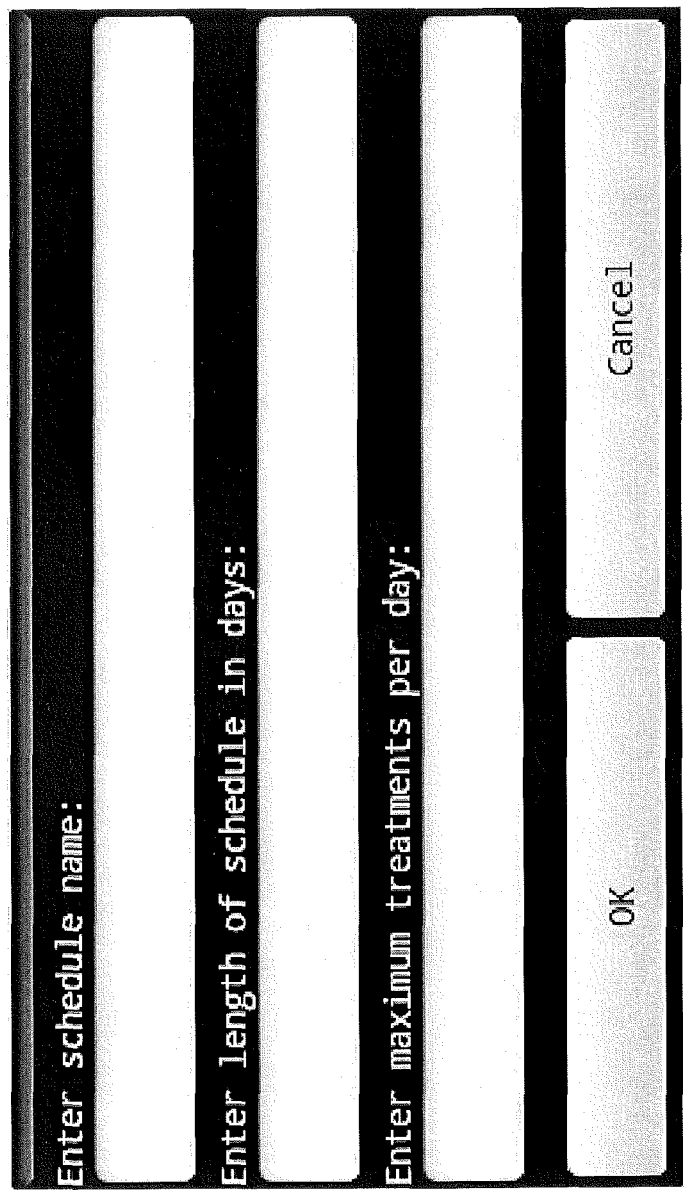
Figure 6:
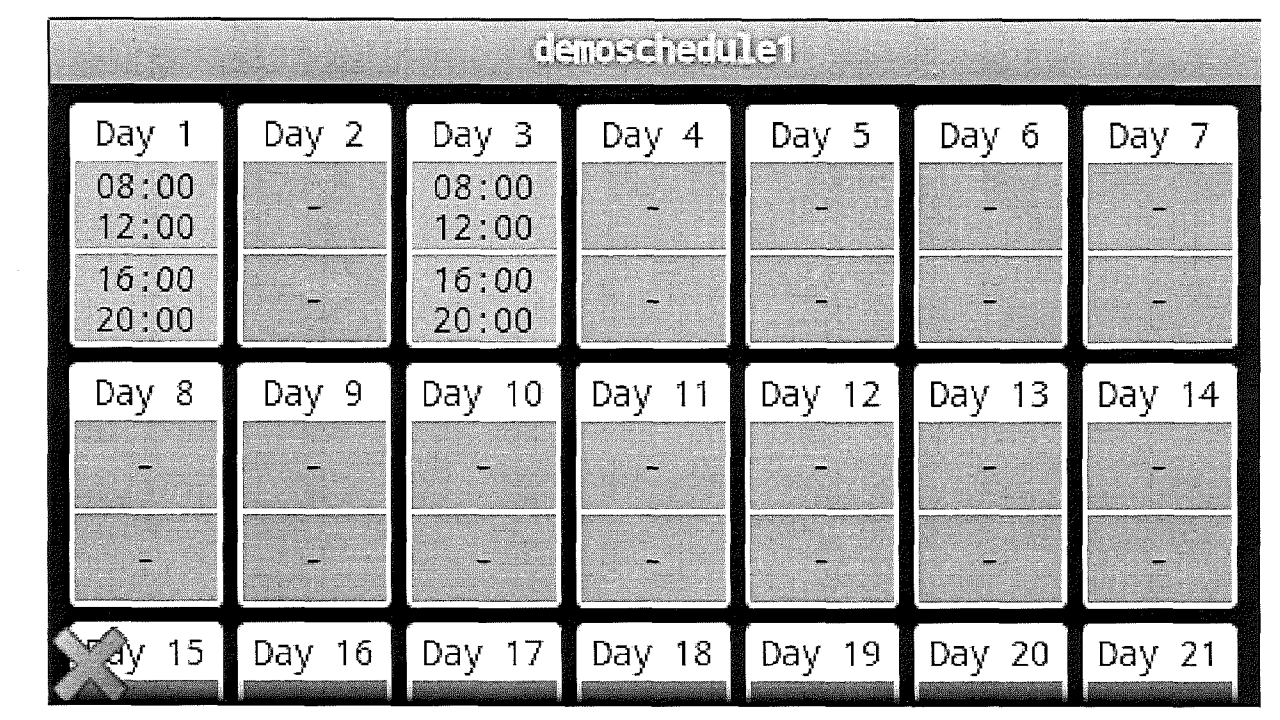
Figure 7:
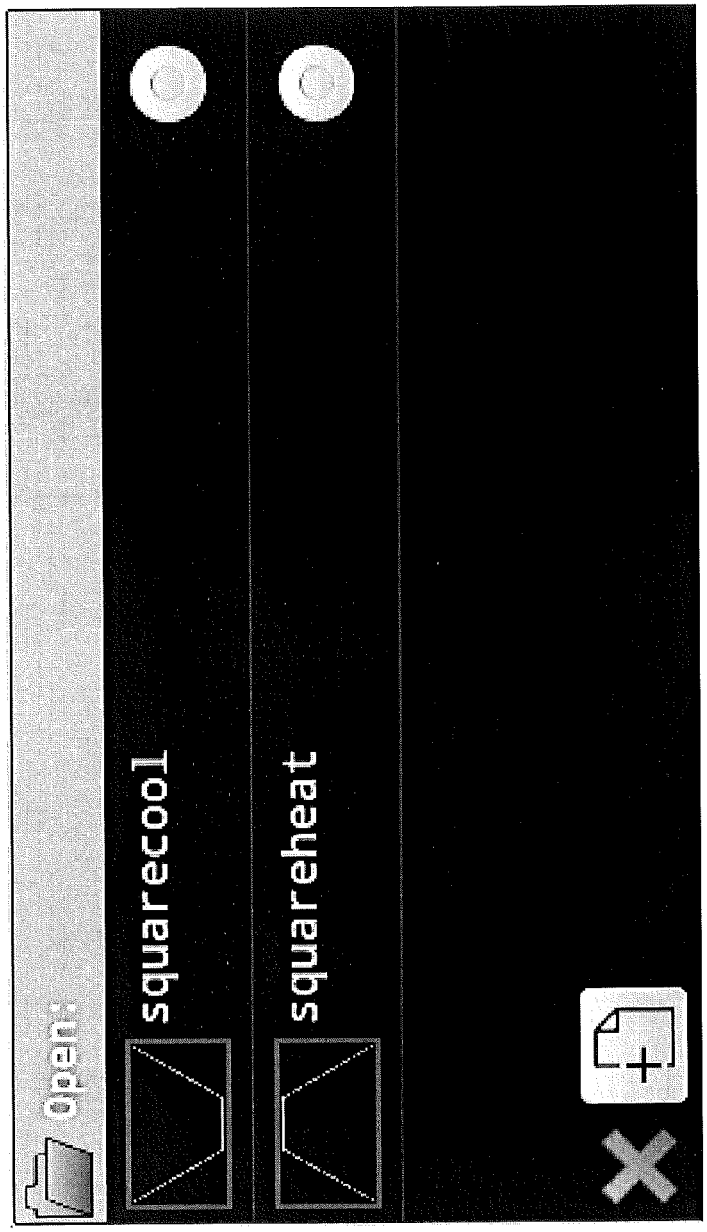
Figure 8:
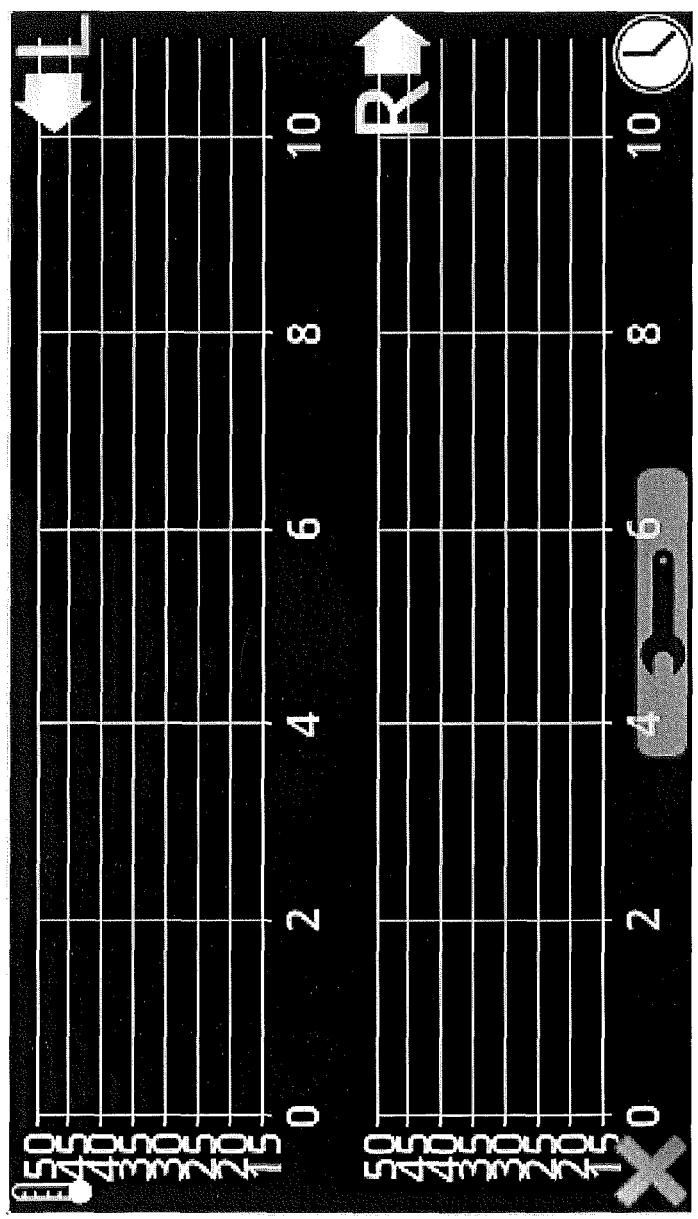
Figure 9:

In some embodiments, the treatment module comprises software that enables a user to select one or more thermal waveforms from a database (e.g., an idealized thermal waveform from an idealized waveform database) and to provide instructions as to when/how each of those waveforms should be administered. For example, a treatment module may comprise software that enables a user to provide instructions as to how long a treatment schedule is to last (FIG. 5), to provide instructions as to how many treatments may be administered each day (FIG. 5), to provide instructions as to how often each thermal waveform is to be administered (FIG. 6), to provide instructions as to what time(s) of day each thermal waveform is to be administered (FIGS. 6 and 9), to select one or more idealized thermal waveforms from a database (FIG. 7), to provide instructions regarding whether each of the selected thermal waveforms is to be delivered to the right and/or left ear canal of a patient (FIG. 8), etc.

Figure 10:

In some embodiments, the treatment module comprises software that enables a user to modify, update and/or extend a prescription by changing one or more parameters of the prescription (FIG. 10), including, but not limited to, which thermal waveform(s) are delivered, frequency with which the thermal waveform(s) is/are delivered, and the expiration date of the prescription. Any suitable prescription may be modified, updated and/or extended, including, but not limited to, prescriptions stored in a prescription database (e.g., a prescription database residing in the controller, in a patient control device, in a physician control device, in a physician support device, in a registry or in a portable memory device, such as a portable SD memory card).

The treatment module may be configured to retrieve/select thermal waveforms from any suitable database, including, but not limited to, a waveform database residing in the controller, a waveform database residing in a patient control device, a waveform database residing in a physician control device, a waveform database residing in a physician support device, a waveform database residing in a registry and/or a waveform database residing in a portable memory device (e.g., an SD memory card).

The treatment module may be configured to retrieve prescriptions from any suitable database, including, but not limited to, a prescription database residing in the controller, a prescription database residing in a registry and/or a prescription database residing in a portable memory device (e.g., an SD memory card).

Prescriptions generated, modified, updated and/or extended by the treatment module may be added to a database comprising one or more prescriptions. For example, the prescriptions may be stored in a prescription database residing in the controller, a prescription database residing in a registry and/or a prescription database residing in a portable memory device.

Control Module.

In some embodiments, the controller comprises a control module configured to activate at least one TED (i.e., to control the magnitude, duration, waveform and other attributes of stimulation delivered by the at least one TED). The control module may be configured to activate the TED(s) to deliver any suitable thermal waveform or combination of thermal waveforms, including, but not limited to, those described in U.S. Provisional Patent Application Nos. 61/424,132, 61/498,096, 61/424,326, 61/498,080, 61/498,911 and 61/498,943, the disclosure of each of which is incorporated herein by reference in its entirety.

In some embodiments, the control module is configured to selectively and separately activate a plurality of TEDs (e.g., by activating only one of said plurality of TEDs, by heating one TED and cooling another, by sequentially activating the TEDs, by activating different TEDs using different temperature/timing parameters, combinations of some or all of the foregoing, etc.).

In some embodiments, the control module is configured to activate the TED(s) based upon a prescription. For example, the control module may be configured to activate one or more TEDs based upon a prescription comprising a set of instructions for delivering one or more thermal waveforms to the vestibular system and/or the nervous system of a patient.

In some embodiments, the control module is configured to receive and/or retrieve instructions for delivering a thermal waveform from a database. For example, the control may be configured to receive and/or retrieve a prescription comprising a set of instructions for delivering one or more thermal waveforms to the vestibular system and/or the nervous system of a patient from a prescription database residing in the controller, from a prescription database residing in a registry and/or from a prescription database residing in a portable memory device (e.g., an SD memory card).

In some embodiments, the control module is configured to adjust one or more attributes of TED activation (e.g., magnitude, duration, wave pattern, etc.) in response to controller feedback data received from one or more TEDs and/or one or more sensors. For example, the control module may be configured to increase/decrease the magnitude of TED activation in response to controller feedback data indicating that an earpiece that is thermally coupled to the TED has not yet reached a target temperature (e.g., the control module may be configured to increase the current flowing through the TED in response to controller feedback data indicating that the temperature of the earpiece has not yet dropped to the target temperature in response to a cooling waveform).

Network module.

In some embodiments, the controller comprises a network module configured to receive, retrieve and/or transmit data. The network module may be configured to receive, retrieve and/or transmit data from/to any suitable device/module/database, including, but not limited to, other modules residing in the controller, databases residing in the controller, a registry, a TED, a sensor and a portable memory device (e.g., an SD memory card).

The network module may be configured to receive, retrieve and/or transmit data over any suitable wired or wireless communications channel, including, but not limited to, a LAN, the Internet, a public telephone switching network, Bluetooth, WLAN and the like.

The network module may be configured to receive, retrieve and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and/or patient information.

In some embodiments, the network module is configured to receive and/or retrieve data associated with the parameters, indications and/or approvals of one or more thermal waveforms from a waveform module/database residing in the controller, from a registry and/or from a portable memory device.

In some embodiments, the network module is configured to receive and/or retrieve one or more prescriptions from a treatment module residing in the controller, from a registry and/or from a portable memory device.

In some embodiments, the network module is configured to receive and/or retrieve controller feedback data, data associated with the delivery of one or more thermal waveforms and/or data associated with the fit of one or more earpieces from a control module residing in the controller, from an impedance module residing in the controller, from a feedback module/database residing in the controller, from one or more TEDs and/or from one or more sensors.

In some embodiments, the network module is configured to receive and/or retrieve patient feedback data, physician feedback data and/or patient information from a feedback module/database residing in the controller, from a GUI module residing in the controller, from a patient information database residing in the controller, from a registry and/or from a portable memory device.

In some embodiments, the network module is configured to transmit data associated with the parameters, indications and/or approvals of one or more thermal waveforms to a waveform module/database residing in the controller, to a treatment module residing in the controller, to a registry and/or a to portable memory device.

In some embodiments, the network module is configured to transmit one or more prescriptions to a treatment module residing in the controller, to a prescription database residing in the controller, to a registry and/or to a portable memory device.

In some embodiments, the network module is configured to transmit controller feedback data, data associated with the delivery of one or more thermal waveforms and/or data associated with the fit of one or more earpieces to a control module residing in the controller, to a feedback module/database residing in the controller, to a registry and/or to a portable memory device.

In some embodiments, the network module is configured to transmit patient feedback data, physician feedback data and/or patient information to a feedback module/database residing in the controller, to a patient information database residing in the controller, to a registry and/or to a portable memory device.

In some embodiments, the network module is configured to access a database comprising data associated with the parameters, indications and/or approvals of one or more thermal waveforms (e.g., idealized thermal waveforms). For example, the network module maybe configured to access a waveform database residing in the controller, a waveform database residing in a registry and/or a waveform database residing in a portable memory device.

In some embodiments, the network module is configured to access a database comprising one or more prescriptions. For example, the network module maybe configured to access a prescription database residing in the controller, a prescription database residing in a registry and/or a prescription database residing in a portable memory device.

In some embodiments, the network module is configured to access a database comprising controller feedback data, data associated with the delivery of one or more thermal waveforms, data associated with the fit of one or more earpieces, patient feedback data and/or physician feedback data. For example, the network module maybe configured to access a feedback database residing in the controller, a feedback database residing in a registry and/or a feedback database residing in a portable memory device.

In some embodiments, the network module is configured to access a database comprising patient information. For example, the network module maybe configured to access a patient information database residing in the controller, a patient information database residing in a registry and/or a patient information database residing in a portable memory device.

Graphical User Interface Module.

In some embodiments, the controller comprises a GUI module configured to display information and/or to accept user input. Any suitable GUI may be used, including, but not limited to, a keyboard, a mouse, an LCD display with one or more associated entry keys and an interactive touch screen. For example, the GUI may comprise a static pressure touch-sensitive display, a capacitive touch-sensitive display, a resistive touch-sensitive display, an electrostatic capacity proximity sensor, a magnetic proximity sensor and/or an infrared proximity sensor. See, e.g., U.S. Patent Publication Nos. 2011/0271222, 2011/0273575, 2011/0275414 and 2011/0275416.

The GUI module may be configured to display any suitable information, including, but not limited to, data associated with the delivery of one or more thermal waveforms. For example, the GUI module may be configured to display the current date and/or time (FIG. 10); the current temperature(s) of the earpiece(s) associated with the controller; the current temperature(s) of a patient's ear canal(s); the current temperature(s) of a patient's inner ear(s); the current temperature(s) of the heat sink(s) associated with the controller; one or more target temperatures (FIG. 11); the amount of time that has elapsed since the onset of delivery of one or more thermal waveforms (FIG. 11); the amount of time remaining in the delivery of one or more thermal waveforms (FIG. 11); the amount of time that has elapsed since the onset of a treatment session; the amount of time remaining in a treatment session; a graphical representation of the thermal waveform being applied (FIG. 11); the number of treatment sessions that have been administered for a prescription; the number of treatment sessions remaining in a prescription; the amount of time remaining until a prescription must be renewed/updated; the amount of remaining battery life, an alert message (e.g., a reminder to a patient that he/she is due for a treatment session); the target time/temperature parameters of one or more prescribed thermal waveform(s) (FIG. 11); the precise time/temperature parameters of the thermal waveform(s) delivered to a patient; the date/time of delivery of the thermal waveform(s) delivered to a patient; the temperature(s) of a patient's ear canal(s) at various time points before, during and/or after delivery of the thermal waveform(s); the temperature(s) of a patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from a patient's ear canal to the inner ear); reaction time (i.e., how long it took for a patient to react to one or more thermal waveforms); the effectiveness of one or more thermal waveforms (i.e., whether and to what extent symptoms were relieved, whether the thermal waveform(s) enhanced the effectiveness of another agent/therapy, etc.); the stability of a treatment (i.e., how long the effects of the treatment lasted); the instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood Ale levels, blood glucose levels and blood cortisol levels); saliva chemistry data (e.g., saliva cortisol levels); urine chemistry data (e.g., urine cortisol levels)), comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which a patient's inner ear cools in response to a cooling stimulus (e.g., data from a temperature sensor, such as thermistor, that monitors how quickly the inner ear cools in response to a cooling waveform); the rate at which a patient's inner ear warms in response to a warming stimulus (e.g., data from a temperature sensor, such as thermistor, that monitors how quickly the inner ear warms in response to a warming waveform) and/or patient comments regarding the subjective fit of his/her earpiece(s).

The GUI module may be configured to accept any suitable user input, including, but not limited to, instructions for generating and/or modifying the parameters, indications and/or approvals of a thermal waveforms; instructions for generating, modifying, updating and/or extending a prescription; patient feedback, physician feedback and/or patient information. For example, the GUI module may be configured to accept a pain score and/or patient comments regarding the effectiveness of a treatment session.

Figure 11:
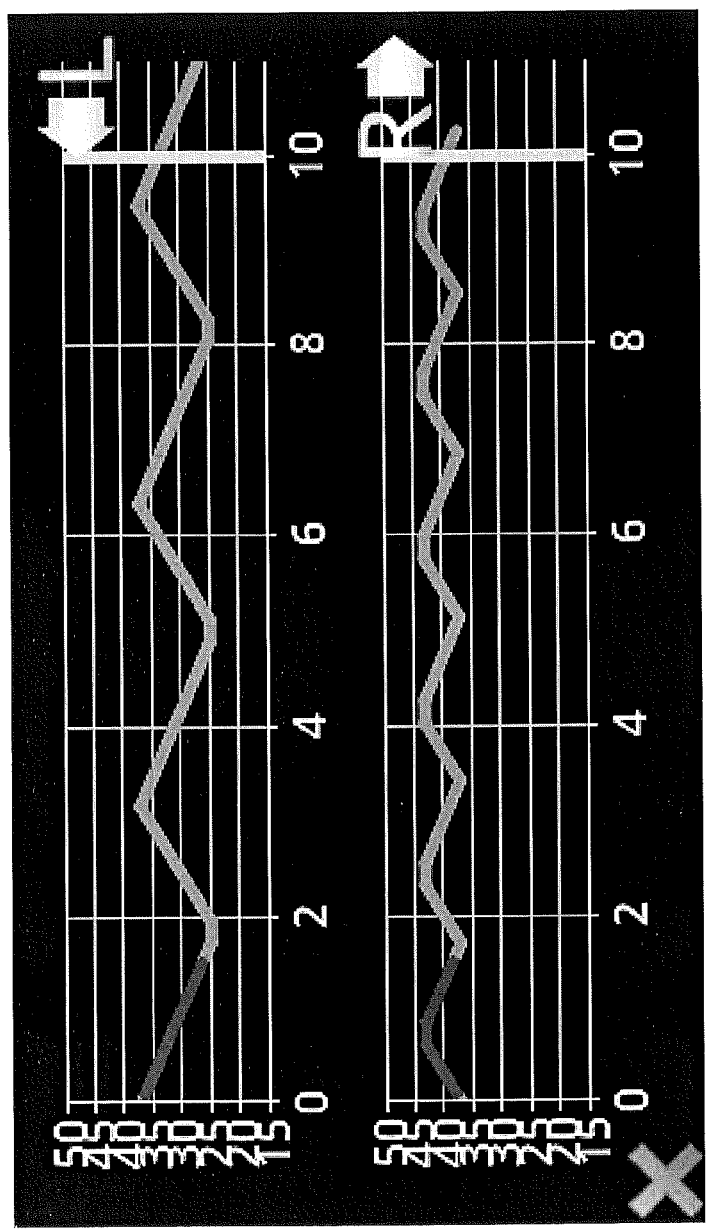

In some embodiments, the GUI module is configured to allow a user to initiate/stop a treatment session (e.g., by pushing/selecting an emergency shutoff button/icon) (FIG. 11).

Feedback Module.

In some embodiments, the controller comprises a feedback module configured to receive, transmit and/or analyze data.

The feedback module may be configured to receive and/or transmit data from/to any suitable device/module/database, including, but not limited to, other modules residing in the controller, databases residing in the controller, a registry, a TED, a sensor and a portable memory device (e.g., an SD memory card).

The feedback module may be configured to receive and/or transmit data over any suitable wired or wireless communications channel, including, but not limited to, a LAN, the Internet, a public telephone switching network, Bluetooth, WLAN and the like.

The feedback module may be configured to receive, transmit and/or analyze any suitable data, including, but not limited to, controller feedback data, data associated with the delivery of one or more thermal waveforms, data associated with the fit of one or more earpieces, patient feedback data, physician feedback data and/or patient information.

In some embodiments, the feedback module is configured to receive and/or analyze controller feedback data, data associated with the delivery of one or more thermal waveforms and/or data associated with the fit of one or more earpieces from an impedance module residing in the controller, from a feedback database residing in the controller, from one or more TEDs and/or from one or more sensors. For example, the feedback module may be configured to analyze the accuracy with which one or more prescribed waveforms was delivered to a patient, the fit of an earpiece based upon the rate at which the temperature of the earpiece changes in response to a cooling/warming waveform, the slew rate associated with one or more TEDs, the impedance between an earpiece positioned in the left ear canal of a patient and an earpiece positioned in the right ear canal of a patient, the impedance between an earpiece positioned in the ear canal of a patient and an electrode affixed to a second location on/in the patient's body, etc.

In some embodiments, the feedback module is configured to receive and/or analyze patient feedback data, physician feedback data and/or patient information from a GUI module residing in the controller, from a registry and/or from a portable memory device. For example, the feedback module may be configured to analyze the effectiveness of a given thermal waveform or combination of thermal waveforms (e.g., by analyzing pain scores entered before, during and after a treatment session), the effect(s) of one or more waveform modifications (e.g., by analyzing whether/how much a given waveform modification changed the effectiveness of a thermal waveform in treating a disease/disorder), etc.

In some embodiments, the feedback module is configured to transmit controller feedback data, data associated with the delivery of one or more thermal waveforms, data associated with the fit of one or more earpieces, patient feedback data, physician feedback data, patient information and/or data associated with its analysis to a control module residing in the controller, to a feedback database residing in the controller, to a patient information database residing in the controller, to a registry and/or to a portable memory device (e.g., an SD memory card).

Alert Generation Module.

In some embodiments, the controller comprises an alert generation module configured to generate one or more alert messages.

The alert generation module may be configured to generate any suitable alert message, including, but not limited to, a reminder that a patient is due for a treatment session; a reminder that a patient must enter patient feedback data (e.g., a pain score) following a treatment session; an indication of the number of treatment sessions remaining in a prescription; an error message indicating that a treatment session has been interrupted due to a system error; an alert indicating that one or more idealized thermal waveforms has been modified; an alert indicating that a given modification is likely to increase/decrease the effectiveness of a given thermal waveform and/or an alert indicating that a given thermal waveform, class of thermal waveforms or combination of thermal waveforms has been identified as being indicated and/or approved for use in the treatment of a disease/disorder; a reminder that a patient must contact his/her physician to update/extend his/her prescription and a warning that the controller's internal power supply is low.

In some embodiments, the alert generation module is configured to communicate with various devices/modules, including, but not limited to, a registry, a TED, a sensor, a portable memory device (e.g., an SD memory card) and other modules of the controller. For example, the alert generation module may be configured to provide instructions to the GUI module and/or the tone generation module for displaying one or more alert messages and/or for generation an audible tone to alert a user of the presence of the one or more alert messages. The graphical user interface module may be configured to display the one or more alert messages immediately upon generation or upon interaction with a user (e.g., an alert notification icon may be generated, with the alert message being displayed only after the user indicates that he/she wishes to view the message).

Tone Generation Module.

In some embodiments, the controller comprises a tone generation module configured to produce audible tones. In some such embodiments, the tone generation module comprises a piezo buzzer. Audible tones may be produced to alert a user to various circumstances/events, including, but not limited to, the start of a treatment session, the end of a treatment session, interruption of a treatment session, low battery power and the existence of an unread/unviewed alert message. Audible tones may be generated repeatedly in response to a single circumstance/event (e.g., an audible tone may be generated repeatedly until the user views/reads the message) and may become progressively louder and/or more frequent with time.

Visual Indicator Module.

In some embodiments, the controller comprises a visual indicator module configured to notify a user of the existence of an unread/unviewed alert message and/or to notify the user that a treatment session is in progress. In some such embodiments, the visual indicator module comprises an LED indicator light. The visual indicator module may be activated repeatedly in response to a single alert message (e.g., an LED light may be illuminated repeatedly until the user views/reads the message) or may remain activated until the user views/reads the message. In some preferred embodiments, an LED indicator light may be illuminated throughout a treatment session and deactivated upon completion of the treatment session, and may change color to signal various events within a treatment session (e.g., the light may appear blue during cooling periods and appear red during heating periods).

Impedance Module.

In some embodiments, the controller comprises an impedance module configured to detect and/or monitor the impedance and/or capacitance between an earpiece inserted into the ear canal of a patient and an electrode affixed to a second location on/in said patient's body. For example, the impedance module may be configured to deliver an electrical current to the earpiece and to measure and/or record the impedance and/or capacitance between the earpiece and the electrode.

In some embodiments, the impedance module may be configured to detect and/or monitor the impedance and/or capacitance between an earpiece inserted into the right ear canal of a patient and an earpiece inserted into the left ear canal of said patient. For example, the impedance module may be configured to deliver an electrical current to the earpiece inserted into the right ear canal of the patient and to measure and/or record the impedance and/or capacitance between the two earpieces.

Without wishing to be bound by theory, it is believed that if each of the earpieces is in substantially good thermal contact with the patient's ear canal, then the earpieces will also be in substantially good electrical contact with the patient's ear canals, and the patient's head will substantially complete an electrical circuit between the earpieces. However, if either of the earpieces is not in substantially good thermal contact with the patient's ear canal, then there will generally be poor electrical contact with the patient's ear canal, and the patient's head will not complete the electrical circuit between the earpieces and an open circuit will be detected by the impedance module.

The impedance value between an earpiece inserted into the ear canal of the patient and the electrode affixed to a second location (e.g., an earpiece inserted into the patient's other ear canal) may be used to estimate the thermal contact between the earpiece(s) and the patient's ear canal(s). In some embodiments, impedance values may be detected for a range of patients to determine a range of impedance values in which it may be assumed that the earpiece(s) is/are in substantially good thermal contact with the patient's ear canal(s). When a vestibular stimulation device is being fitted to a new patient, the impedance value may be detected, and if the impedance value is within the acceptable range, it may be assumed that there is substantially good thermal contact between the earpiece(s) and the patient's ear canal(s). In some embodiments, when a vestibular stimulation device is being fitted to a new patient, the impedance value between the earpiece inserted into the right ear canal of the patient and the earpiece inserted into the left canal of the patient may be detected and used as a patient-specific baseline to later determine whether the patient is using the vestibular stimulation device in the proper configuration (i.e., whether the earpieces are properly fitted into the patient's ear canals during a given treatment session).

The impedance module may be configured to monitor the impedance value between an earpiece inserted into the ear canal of a patient and an electrode affixed to a second location on/in said patient's body (e.g., between two earpieces), and the impedance values may be analyzed (e.g., by a medical health professional or the impedance module) to determine whether the earpiece(s) is/was properly fitted at various times before, during and/or after delivery of the thermal waveform(s). In some embodiments, the impedance module may be configured to provide feedback to the user if/when the impedance value indicates that the earpiece(s) are not in substantially good thermal contact with the patient's ear canal(s). In this configuration, the impedance module may provide an estimation of a degree of thermal contact between the earpiece(s) and the patient's ear canal(s) in real-time or in data recorded and analyzed at a later time.

The impedance module may be configured to provide controller feedback data to the control module so that the control module may modulate the amplitude of the waveform(s) delivered by the TED(s) responsive to the degree of thermal contact between the earpiece(s) and the patient's ear canal(s). For example, if the impedance module determines that there is a poor fit and poor thermal contact between the earpiece(s) and the ear canal(s), then the control module may increase the thermal output of the TED(s) to compensate for the poor thermal contact.

Security Module.

In some embodiments, the controller comprises a security module configured to prevent unauthorized use of the controller (i.e., to prevent unauthorized persons from using the vestibular stimulation device, to prevent authorized persons from using the vestibular stimulation device in an unauthorized manner, etc.).

Figure 12:
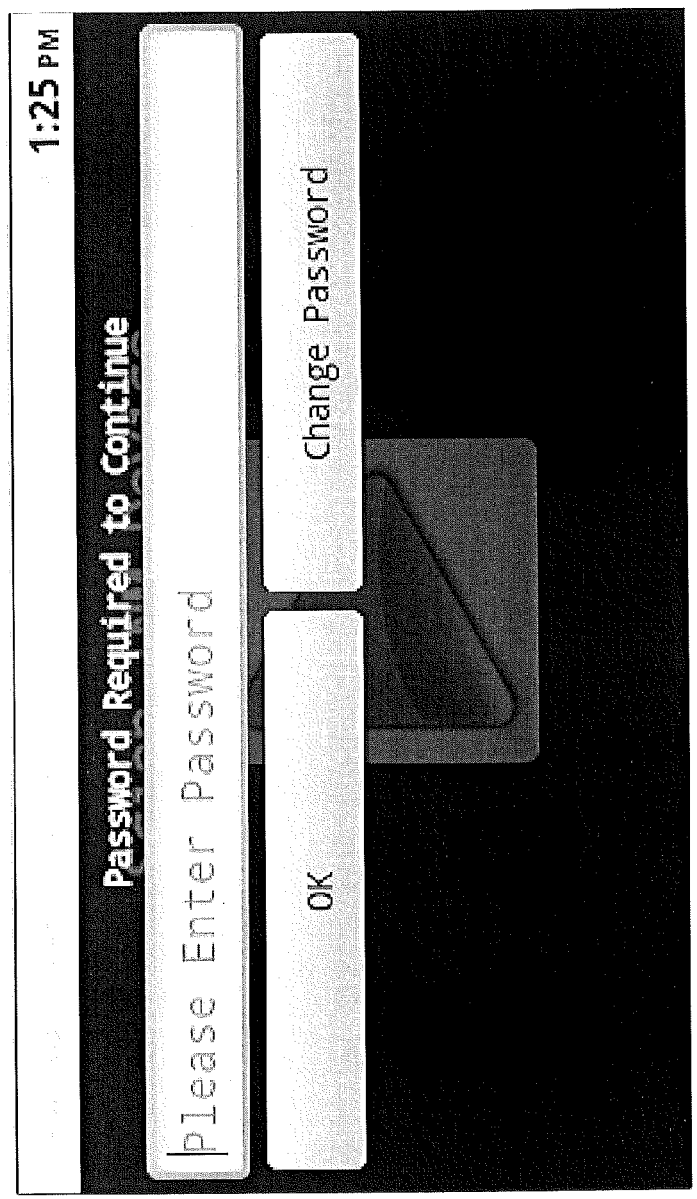

The security module may be configured to prevent unauthorized use of the controller using any suitable means of security, including, but not limited to, password protection and data encryption. For example, the security module may be configured such that a user is required to input a designated password prior to initializing treatment; generating and/or modifying a thermal waveform; generating, modifying, updating and/or extending a prescription; entering/viewing patient feedback data; entering/viewing physician feedback data and/or entering/viewing patient information (FIG. 12). In some embodiments, prescriptions are provided in an encrypted format, and the security module is configured such that the prescriptions can only be decrypted by the vestibular stimulation device assigned to or belonging to the patient for whom the prescription was generated. In some embodiments, prescriptions are provided in an encrypted format, and the security module is configured such that the prescriptions can only be decrypted by inputting a designated decryption key. In some embodiments, a patient may be required to purchase a decryption key and/or password for each treatment session, prescription, refill, etc.

Safety Module.

In some embodiments, the controller comprises a safety module configured to deactivate the controller in the event of a system malfunction and/or failure.

The safety module may be configured to deactivate the controller for any suitable reason, including, but not limited to, excessive heating and/or cooling of an earpiece, excessive heating and/or cooling of a heat sink, a loss of thermal coupling between an earpiece and the TED(s) with which it is associated, a loss of thermal coupling between a heat sink and the TED(s) with which it is associated, patient noncompliance (e.g., if the patient has removed the earpiece(s) during a treatment session) and faulty signaling from the controller to the associated TED(s).

In some embodiments, the safety module is configured to deactivate the controller if/when the temperature of an earpiece surpasses a specified safety threshold. For example, the safety module may be configured to deactivate the controller if/when the temperature of the earpiece drops below about 10° C. and/or rises above about 50° C.

In some embodiments, the safety module is configured to deactivate the controller if/when the temperature of a heat sink that is thermally coupled to an earpiece surpasses a specified safety threshold. For example, the safety module may be configured to deactivate the controller if/when the temperature of the heat sink drops below about 5° C. and/or rises above about 50° C.

In some embodiments, the safety module is configured to deactivate the controller if/when one or more of the activation signals sent from the controller to the associated TED(s) indicates that the system is may be operating outside of a predefined safety range. For example, the safety module may be configured to deactivate the controller if/when an activation signal sent from the controller to an associated TED exceeds the level of activation that would normally be required to deliver the prescribed thermal waveform in a properly functioning system.

As will be appreciated by one of skill in the art, the controller may comprise any suitable data, including, but not limited to, static and/or dynamic data used by the operating system, applications, I/O device drivers and other software components, controller feedback data, data associated with the parameters, indications and/or approvals of one or more thermal waveforms (e.g., idealized thermal waveforms), data associated with one or more prescriptions, data associated with the delivery of one or more thermal waveforms, data associated with the fit of one or more earpieces, patient feedback data, physician feedback data and patient information. For example, the controller may comprise a waveform database comprising data associated with the parameters, indications and/or approvals of one or more idealized thermal waveforms; a prescription database comprising data associated with one or more prescriptions; a feedback database comprising controller feedback data, data associated with the delivery of one or more thermal waveforms to the vestibular system and/or the nervous system of a patient, patient feedback data and physician feedback data and/or a patient history database comprising data associated with one or more patients. In some embodiments, two or more of the aforementioned databases are combined to form a single database comprising data from each of the individual databases (e.g., the controller may comprise a feedback-history database comprising data associated with the delivery of one or more thermal waveforms and patient information). In some embodiments, one of the aforementioned databases is split into two or more distinct databases (e.g., the controller may comprise a controller feedback database comprising controller feedback data, a delivery feedback database comprising data associated with the specific parameters of the thermal waveform(s) delivered to a patient, a patient feedback database comprising patient feedback data and a physician feedback database comprising physician feedback data). In some embodiments, one or more of the data types described below with respect to one of the databases described below is stored in one of the other databases described below (e.g., the patient information database, rather than the feedback database, may be configured to receive/store patient feedback data). In some embodiments, data is transmitted, received and/or stored in a controlled format (e.g., in a standardized format using forms/programs supplied by a registry). The controller may be configured to transmit, receive and store data in a manner that ensures compliance with any and all applicable laws and/or regulations (e.g., the Health Insurance Portability and Accountability Act of 1996 (P.L. 104-191; "HIPAA")).

Waveform Database.

In some embodiments, the controller comprises a waveform database configured to receive, transmit and/or store data associated with the parameters, indications and/or approvals of one or more thermal waveforms (e.g, one or more idealized thermal waveforms). In some such embodiments, the waveform database is configured such that one or more of the thermal waveforms stored therein is/are protected (e.g., users may be prevented from modifying and/or deleting the idealized thermal waveform(s) stored in the waveform database).

The waveform database may comprise any suitable type of memory including, but not limited to, cache, ROM, PROM, EPROM, EEPROM, flash memory, SRAM and DRAM. In some embodiments, the waveform database comprises a portable memory device, such as an SD memory card or a USB memory stick. For example, the waveform database may comprise an SD memory card interface and one or more prescriptions may be stored on a portable SD memory card.

The waveform database may be configured to receive and/or transmit data from/to any suitable device/module/database, including, but not limited to, modules residing in the controller, a registry, a TED, a sensor and a portable memory device (e.g., an SD memory card).

The waveform database may be configured to receive and/or transmit data over any suitable wired or wireless communications channel, including, but not limited to, a LAN, the Internet, a public telephone switching network, Bluetooth, WLAN and the like.

Prescription Database.

In some embodiments, the controller comprises a prescription database configured to receive, transmit and/or store one or more prescriptions, wherein each prescription comprising a set of instructions for delivering one or more thermal waveforms to the vestibular system and/or the nervous system of a patient.

The prescription database may comprise any suitable type of memory including, but not limited to, cache, ROM, PROM, EPROM, EEPROM, flash memory, SRAM and DRAM. In some embodiments, the prescription database comprises a portable memory device, such as an SD memory card or a USB memory stick. For example, the prescription database may comprise an SD memory card interface and one or more prescriptions may be stored on a portable SD memory card.

The prescription database may be configured to receive and/or transmit data from/to any suitable device/module/database, including, but not limited to, modules residing in the controller, a registry, a TED, a sensor and a portable memory device (e.g., an SD memory card).

The prescription database may be configured to receive and/or transmit data over any suitable wired or wireless communications channel, including, but not limited to, a LAN, the Internet, a public telephone switching network, Bluetooth, WLAN and the like.

Feedback Database.

In some embodiments, the controller comprises a feedback database configured to receive, transmit and/or store data.

The feedback database may comprise any suitable type of memory including, but not limited to, cache, ROM, PROM, EPROM, EEPROM, flash memory, SRAM and DRAM. In some embodiments, the feedback database comprises a portable memory device, such as an SD memory card or a USB memory stick. For example, the feedback database may comprise an SD memory card interface and one or more prescriptions may be stored on a portable SD memory card.

The feedback database may be configured to receive and/or transmit data from/to any suitable device/module/database, including, but not limited to, modules residing in the controller, a registry, a TED, a sensor and a portable memory device (e.g., an SD memory card).

The feedback database may be configured to receive and/or transmit data over any suitable wired or wireless communications channel, including, but not limited to, a LAN, the Internet, a public telephone switching network, Bluetooth, WLAN and the like.

The feedback database may be configured to receive/transmit and/or store any suitable data, including, but not limited to, controller feedback data, data associated with the delivery of one or more thermal waveforms, data associated with the fit of one or more earpieces, patient feedback data, physician feedback data and/or patient information. For example, the feedback database may comprise a log file detailing the target time/temperature parameters of one or more prescribed thermal waveform(s); the time/temperature parameters of the thermal waveform(s) delivered to a patient; the date/time of delivery of the thermal waveform(s) delivered to a patient; the temperature(s) of a patient's ear canal(s) at various time points before, during and/or after delivery of one or more thermal waveforms; the temperature(s) of a patient's inner ear(s) at various time points before, during and/or after delivery of one or more thermal waveforms; the fit of one or more earpieces at various time points before, during and/or after delivery of one or more thermal waveforms; an estimate of the thermal contact between one or more earpieces and a patient's ear canal(s) at various time points before, during and/or after delivery of one or more thermal waveforms; patient-specific time constants (e.g., a time constant associated with the transduction of heat from a patient's ear canal to the inner ear); a patient's reaction time (i.e., how long it took for a patient to react to one or more thermal waveforms); effectiveness of one or more thermal waveforms (i.e., whether and to what extent symptoms were relieved, whether the thermal waveform(s) enhanced the effectiveness of another agent/therapy, etc.); stability of a treatment (i.e., how long the effects of a treatment lasted); instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)); comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which an earpiece is cooled in response to a cooling stimulus (e.g., data from a temperature sensor, such as thermistor, that monitors how quickly the earpiece cools in response to a cooling waveform); the rate at which an earpiece is warmed in response to a warming stimulus (e.g., data from a temperature sensor, such as a thermistor, that monitors how quickly the earpiece warms in response to a warming waveform); the rate at which a patient's ear canal and/or inner ear cooled in response to a cooling stimulus (e.g., data from a temperature sensor, such as thermistor, that monitors how quickly the ear canal and/or the inner ear cools in response to a cooling waveform); the rate at which a patient's ear canal and/or inner ear warmed in response to a warming stimulus (e.g., data from a temperature sensor, such as a thermistor, that monitors how quickly the ear canal and/or the inner ear warms in response to a warming waveform); patient comments regarding the subjective fit of one or more earpieces; physician comments regarding the effectiveness of one or more thermal waveforms and/or physician comments regarding the effect(s) of one or more waveform modifications.

Patient History Database.

In some embodiments, the controller comprises a patient history database configured to receive, transmit and/or store patient information.

The patient history database may comprise any suitable type of memory including, but not limited to, cache, ROM, PROM, EPROM, EEPROM, flash memory, SRAM and DRAM. In some embodiments, the patient history database comprises a portable memory device, such as an SD memory card or a USB memory stick. For example, the patient history database may comprise an SD memory card interface and one or more prescriptions may be stored on a portable SD memory card.

The patient history database may be configured to receive and/or transmit data from/to any suitable device/module/database, including, but not limited to, modules residing in the controller, a registry, a TED, a sensor and a portable memory device (e.g., an SD memory card).

The patient history database may be configured to receive and/or transmit data over any suitable wired or wireless communications channel, including, but not limited to, a LAN, the Internet, a public telephone switching network, Bluetooth, WLAN and the like.

Patient information may comprise any suitable information that is associated with a patient, including, but not limited to, the patient's medical history, the patient's current symptoms (if any), the patient's present diagnosis (if any), the patient's current prescriptions (if any) and data associated with the delivery of one or more thermal waveforms to the vestibular system and/or the nervous system of the patient.

As will be appreciated by one of skill in the art, the controller may comprise any I/O device drivers, including, but not limited to, software routines accessed through the operating system by the applications to communicate with devices such as I/O ports, memory components, TEDs and/or sensors.

As will be appreciated by one of skill in the art, the controller may be configured (e.g., with computer instructions (i.e., software)) to operate in a plurality of distinct modes. In each mode, the controller may be configured to permit access to some modules, databases and/or functionalities and to prevent access to other modules, database and/or functionalities. For example, the controller may be configured to operate in a patient mode, wherein the user is allowed to perform patient-oriented tasks, such as starting/stopping a treatment session and/or providing feedback regarding the effectiveness of a treatment session, but is prevented from accessing other modules/databases/functionalities (e.g., the user may be prevented generating, modifying, updating and/or extending prescriptions). Similarly, the controller may be configured to operate in a physician mode, wherein the user is allowed to perform physician-oriented tasks, such as generating, modifying, updating and/or extending a prescription comprising a set of instructions for delivering one or more thermal waveforms to the vestibular system and/or the nervous system of a patient, but is prevented from accessing other modules/databases/functionalities (e.g., the user may be prevented from generating and/or modifying one or more thermal waveforms). Likewise, the controller may be configured to operate in a researcher mode, wherein the user is allowed to perform researcher-oriented tasks, such as generating and/or modifying one or more idealized thermal waveforms, but is prevented from accessing other modules/databases/functionalities (e.g., the user may be prevented from modifying the underlying operational parameters of the controller). In addition, the controller may be configured to operate in an engineer mode, wherein the user is allowed to access all of the controller's modules/databases/functionalities. Each mode may be protected via a unique security measure (e.g., the controller may be configured such that each mode is protected by a unique password).

Figure 13:
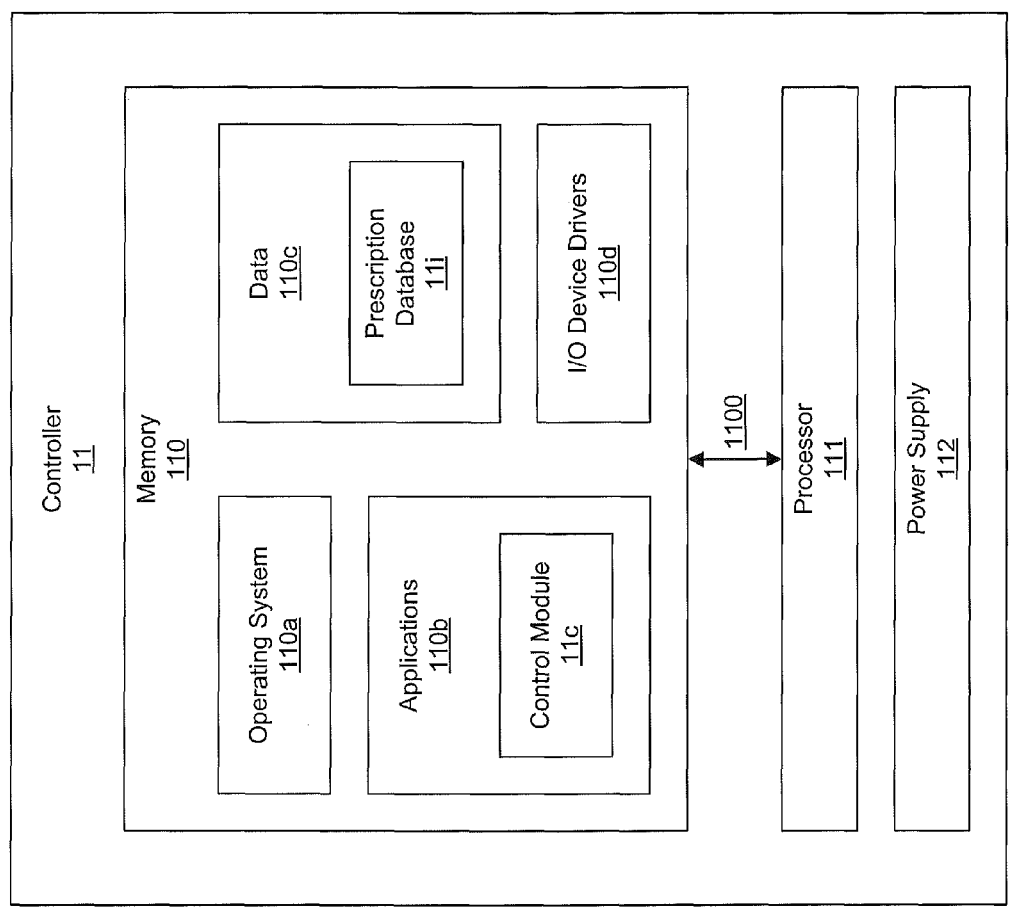
FIG. 13 is a block diagram of a controller according to some embodiments of the present invention.
Figure 14:
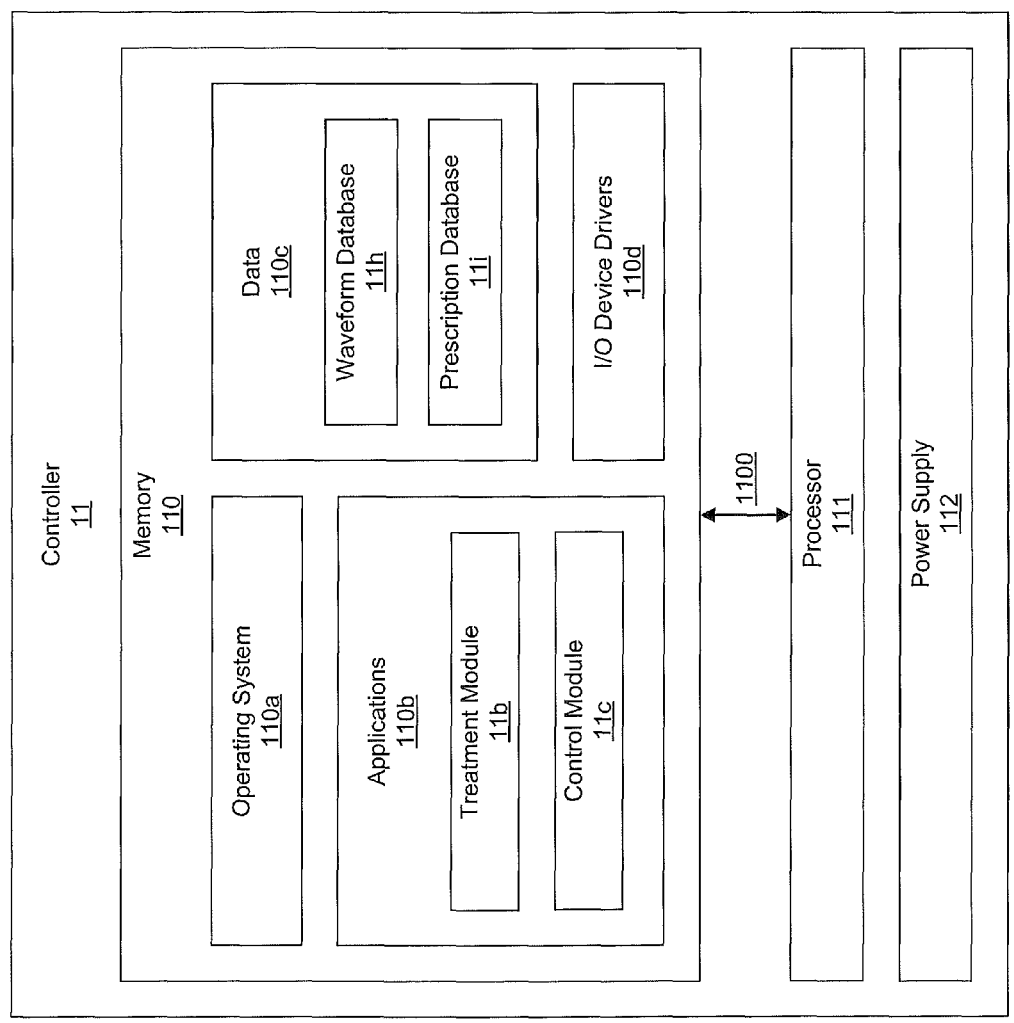
FIG. 14 is a block diagram of a controller according to some embodiments of the present invention.
Figure 15:
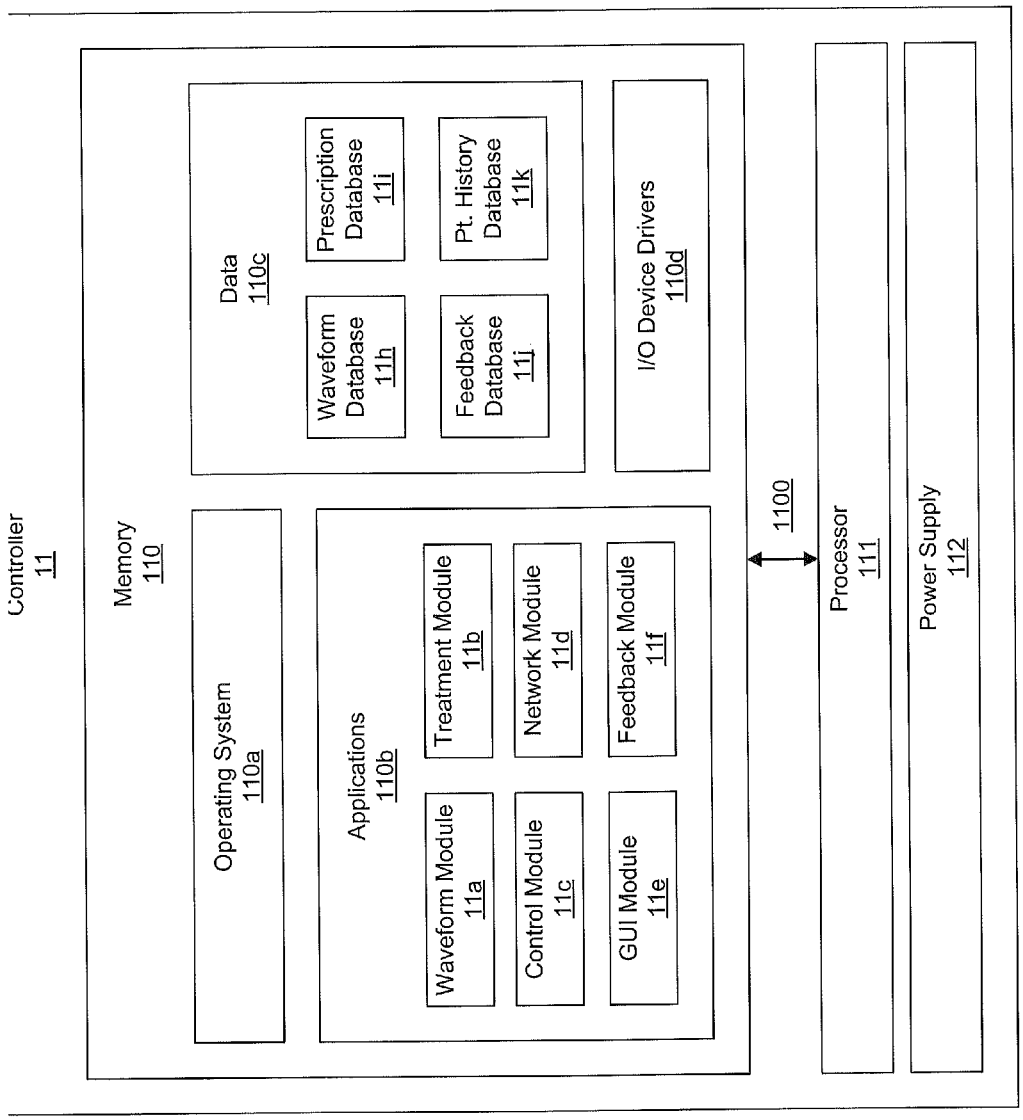
FIG. 15 is a block diagram of a controller according to some embodiments of the present invention.

As shown in FIGS. 13-15, in some embodiments of the present invention, the controller 11 comprises memory 110, a processor 111 and a power supply 112 (e.g., an internal power supply), wherein memory 110 is representative of the overall hierarchy of memory devices containing software and data used to implement the functionality of the controller 11 and wherein the processor 111 communicates with the memory 110 via an address/data bus 1100. In particular embodiments, memory 110 comprises an operating system 110a, applications 110b (e.g., a waveform module 11a configured to generate and/or modify the parameters, indications and/or approvals of one or more thermal waveforms; a treatment module 11b configured to generate, modify, update and/or extend a prescription comprising a set of instructions for delivering one or more thermal waveforms to the vestibular system and/or the nervous system of a patient; a control module 11e configured to activate at least one TED to deliver one or more thermal waveforms to the vestibular system and/or the nervous system of a patient; a network module 11d configured to receive and/or transmit data, a GUI module 11e configured to display information and/or accept user input and/or a feedback module 11f configured to receive, transmit, and/or analyze data), data 110c (e.g., a waveform database 11h comprising data associated with the parameters, indications and/or approvals of one or more thermal waveforms; a prescription database 11i comprising at least one prescription comprising a set of instructions for delivering one or more thermal waveforms to the vestibular system and/or the nervous system of a patient; a feedback database 11j comprising data associated with the delivery of one or more thermal waveforms and/or a patient history database 11k comprising patient information) and I/O drivers 110d. In some such embodiments, data 110c comprises one or more databases stored on a portable memory device. For example, data 110c may comprise an SD memory card interface and a portable SD memory card comprising a waveform database 11h, a prescription database 11i, a feedback database 11j and/or a patient history database ilk.

In some embodiments, the control module 11c is configured to activate one or more TEDs to delivery of one or more thermal waveforms to the vestibular system and/or the nervous system of a patient. For example, the control module 11e may be configured to activate the TED(s) based upon a prescription stored in the prescription database 11i. In some such embodiments, the prescription is stored on an SD memory card inserted into an SD memory card interface.

In some embodiments, the network module 11d is configured to receive data associated with the parameters, indications and/or approvals of one or more thermal waveforms from the waveform module 11a, a registry and/or a portable memory device (e.g., an SD memory card) and to transmit the data to the waveform database 11h for storage. In some such embodiments, the data is stored on an SD memory card inserted into an SD memory card interface.

In some embodiments, the network module 11d is configured to retrieve data associated with the parameters, indications and/or approvals of one or more thermal waveforms from the waveform database 11h, a registry and/or a portable memory device (e.g., an SD memory card) and to transmit the data to the waveform module 11a and/or the treatment module 11b.

In some embodiments, the network module 11d is configured to receive one or more prescriptions from the treatment module 11b, a registry and/or a portable memory device (e.g., an SD memory card) and to transmit the prescription(s) to the prescription database 11i for storage. In some such embodiments, the prescription(s) is/are stored on an SD memory card inserted into an SD memory card interface.

In some embodiments, the network module 11d is configured to retrieve one or more prescriptions from the prescription database 11i, a registry and/or a portable memory device (e.g., an SD memory card) and to transmit the prescription(s) to the treatment module 11b and/or the control module 11c.

In some embodiments, the network module 11d is configured to receive controller feedback data, data associated with the delivery of one or more thermal waveforms and/or data associated with the fit of one or more earpieces from the control module 11c, one or more TEDs 13a, 13b, one or more sensors 14a, 14b, a registry and/or a portable memory device (e.g., an SD memory card) and to transmit that data to the feedback database 11j for storage. In some such embodiments, the data is stored on an SD memory card inserted into an SD memory card interface.

In some embodiments, the network module 11d is configured to receive patient feedback data from the GUI module 11e and to transmit that data to the feedback database 11j for storage. In some such embodiments, the patient information is stored on an SD memory card inserted into an SD memory card interface.

In some embodiments, the network module 11d is configured to retrieve controller feedback data, data associated with the delivery of one or more thermal waveforms, data associated with the fit of one or more earpieces and/or patient feedback data from the feedback database 11j and to transmit the data to the control module 11c, the feedback module 11f, a registry and/or a portable memory device (e.g., an SD memory card).

In some embodiments, the network module 11d is configured to receive patient feedback data from the GUI module 11e and to transmit that data to the feedback database 11j for storage. In some such embodiments, the patient information is stored on an SD memory card inserted into an SD memory card interface.

In some embodiments, the network module 11d is configured to retrieve patient feedback data from the feedback database 11j and to transmit the data to the feedback module 11f, a registry and/or a portable memory device (e.g., an SD memory card).

In some embodiments, the network module 11d is configured to receive patient information from the GUI module 11e, a registry and/or a portable memory device (e.g., an SD memory card) and to transmit that data to the patient history database 11k for storage. In some such embodiments, the patient information is stored on an SD memory card inserted into an SD memory card interface.

In some embodiments, the network module 11d is configured to retrieve patient information from the patient history database 11k and to transmit the patient information to a registry and/or a portable memory device (e.g., an SD memory card).

Figure 16:
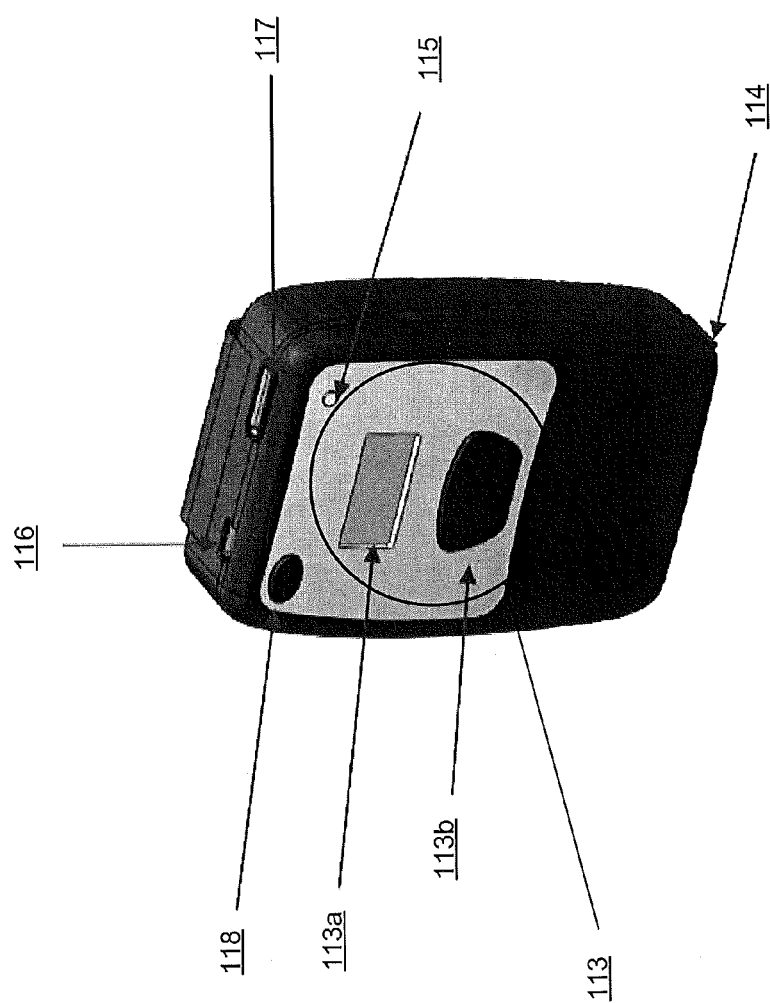
FIG. 16 is an illustration of a controller according to some embodiments of the present invention.

FIG. 16 is an illustration of a controller of the present invention. As shown therein, in some embodiments, the controller may comprise a graphical user interface 113 comprising an LCD display 113a configured to display data associated with the delivery of one or more thermal waveforms and a treatment start/stop button 113b whereby a patient may initiate and/or terminate a treatment session, an SD memory card interface 114 into which an SD memory card comprising a prescription may be inserted, an LED indicator light 115 configured to notify a patient of the occurrence of various events (e.g., the start of a treatment session or the generation of an alert message), a USB interface 116 configured to transmit/receive data and/or to recharge an internal power supply, a lead interface 117 whereby a patient may operatively connect one or more thermal stimulation leads and an on/off button 118.

Figure 17:
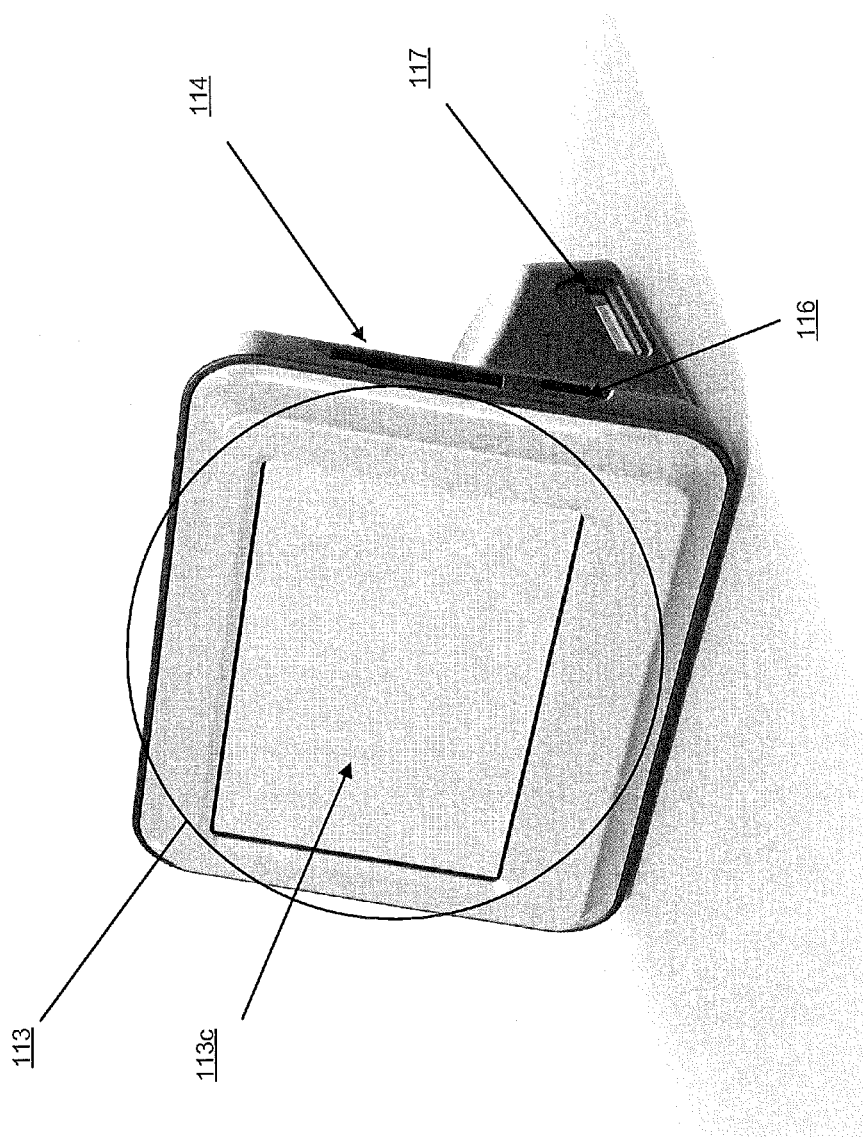
FIG. 17 is an illustration of a controller according to some embodiments of the present invention.

FIG. 17 is an illustration of another controller of the present invention. As shown therein, in some embodiments, the controller may comprise a graphical user interface comprising an interactive touchscreen 113c, an SD memory card interface 114 into which an SD memory card may be inserted, a USB interface 116 configured to transmit/receive data and/or to recharge an internal batter supply and a lead interface 117 whereby a user may operatively connect one or more thermal stimulation leads.

B. Earpiece.

The vestibular stimulation device may comprise one or more earpieces. Earpieces of the present invention may be configured so as to be insertable into the left ear canal and/or the right ear canal of a patient.

Any suitable earpiece can be used to carry out the present invention, including, but not limited to, those described in U.S. Patent Publication Nos. 2010/0198204 and 2010/0198282; in U.S. patent application Ser. Nos. 12/970,312 and 12/970,347; in U.S. Provisional Application Nos. 61/497,761; in U.S. Design Pat. No. D645,455, the disclosure of each of which is incorporated herein by reference in its entirety.

Earpieces of the present invention may comprise any suitable material, including, but not limited to, a rigid, thermally conductive material (e.g., a metal or a metal alloy). For example, the earpiece(s) may comprise aluminum or an aluminum alloy (e.g., 6061 aluminum).

Earpieces of the present invention may be of any suitable size/shape. In some embodiments, the earpiece(s) comprise(s) a distal end configured so as to be insertable into the left ear canal and/or the right ear canal of a patient and a proximal end configured so as to be thermally connected to one or more TEDs. In some embodiments, each earpiece weighs between about 1 and about 10 grams (e.g., about 9 grams or less or about 4 grams or less).

Earpieces of the present invention may possess any suitable heat transfer properties. In some embodiments, the earpiece(s) is/are more efficiently heated than cooled. For example, the earpiece(s) may have a slew rate of about 15° C. per minute or greater during delivery of a cooling stimulus and a slew rate of about 20° C. per minute or greater during delivery of a warming stimulus.

Earpieces of the present invention may comprise a thermally conductive covering. For example, a thermally conductive cushion may cover one or more portions of the earpiece(s) (e.g., the portion of an earpiece that is inserted into the ear canal of a patient during use may be covered in a thermally conductive cushioning material to increase thermal contact between the earpiece and the ear canal (i.e., by conforming to the shape of the ear canal)). The thermally conductive covering may comprise any suitable material, including, but not limited to, coating materials that must be reapplied to the earpiece(s) before each use (e.g., water, water-based lubricants, thermal grease, gels and the like) and reusable coating materials (e.g., a thermally conductive plastic sheath or sleeve).

Earpieces of the present invention may comprise a thermally insulating covering. For example, an insulating sleeve may cover one or more portions of the earpiece(s) (e.g., the portion of an earpiece that remains outside the ear canal of a patient during use may be covered in an insulating sleeve to reduce heat transfer between the earpiece and the outer ear of the patient). The insulating covering may comprise any suitable material, including, but not limited to, coating materials that must be reapplied to the earpiece(s) before each use (e.g., mineral oil, polypropylene, gels and the like) and reusable coating materials (e.g., a thermally insulative sheath or sleeve). In some embodiments, the thermally insulating covering comprises a silicone sleeve.

Earpieces of the present invention may comprise an electrically insulating covering. For example, an electrically insulating coating may cover one or more portions of the earpiece(s) (e.g., the portion of an earpiece that is inserted into the ear canal of a patient during use may be coated with an electrically insulating coating to prevent electrical conductance between the earpiece and the ear canal). The electrically insulating covering may comprises any suitable material, including, but not limited to, metal oxides (e.g., aluminum oxide), glass, porcelain and composite polymer materials. In some embodiments, the surface of an earpiece comprising aluminum is anodized to produce an aluminum oxide coating that electrically insulates the surface of the earpiece.

Earpieces of the present invention may comprise a protective coating. For example, a protective coating may cover one or more portions of the earpiece(s) (e.g., the portion of an earpiece that is inserted into the ear canal of a patient during use may be coated with a protective coating to prevent the underlying surface of the earpiece from coming into contact with the surface of the ear canal during use). The protective coating may comprise any suitable material, including, but not limited to, metals and metal alloys (gold, silver, copper and alloys thereof).

As will be appreciated by one of skill in the art, earpieces of the present invention may comprise a single covering/coating that fulfills multiple purposes. For example, the a thermally conductive coating applied to the portion of an earpiece that is inserted into the ear canal of a patient during use may also prevent the underlying surface of the earpiece from coming into contact with the surface of the ear canal during use.

As will be appreciated by one of skill in the art, earpieces of the present invention may comprise multiple coatings. For example, the earpiece(s) may comprise both a thermally conductive covering and a thermally insulative covering (e.g., a thermally conductive cushion may cover the portion of an earpiece that is inserted into the ear canal of a patient during use and an insulating sleeve may cover the portion of an earpiece that remains outside the ear canal of a patient during use).

As shown in FIGS. 18A-18C, an earpiece 12 of the present invention may comprise a base cavity 120, a tip cavity 121, one or more base apertures 122, and a pressure-relief channel 123.

The base cavity 120 may be configured to receive a TED such that the TED may be thermally coupled to the earpiece 12 by mounting the TED on an interior cavity surface of the base cavity 120.

The tip cavity 121 may be configured to receive a sensor (e.g., a sensor configured to detect the temperature of the earpiece).

The base apertures 122 may be configured to provide a passageway for one or more wires and/or cables (e.g., a thermal stimulation lead connected to a TED, a wire connected to the sensor 14, etc.).

The pressure-relief channel 123 may be configured to provide a pathway through which air and/or moisture may flow during and/or after insertion of the earpiece 12 into the ear canal of a patient (e.g., to reduce the pressure in the ear canal during and/or after insertion of the earpiece 12 and/or to allow moisture to escape the ear canal during and/or after insertion of the earpiece 12). The pressure-relief channel 123 may be of any suitable length and depth (i.e., any length/depth that is sufficient to provide air flow from the interior of the ear canal at the distal tip of the earpiece to the external air outside of the ear canal during and/or after insertion of the earpiece 12). For example, the pressure-relief channel 123 may be generally as long as a side of the earpiece 12 and may be about 0.5 millimeters to 2 millimeters deep. The pressure-relief channel 123 may be located in any suitable location in/on the earpiece (e.g., embedded in an outer surface of earpiece 12 or passing through the interior of the earpiece 12 so as to provide a conduit between the interior of the ear canal and the exterior environment).

C. Thermoelectric Device

The vestibular stimulation device may comprise one or more TEDs. TEDs of the present invention may be operatively connected to one or more controllers and may be used deliver one or more thermal waveforms to the vestibular system and/or the nervous system of a patient (e.g., by warming and/or cooling an earpiece inserted into the ear canal of said patient).

Any suitable thermoelectric device can be used to carry out the present invention, including, but not limited to, those described U.S. Pat. Nos. 5,974,806, 6,229,123, 6,977,360, 7,024,865, 7,098,393, 7,202,443 and 7,205,675; in U.S. Patent Publication Nos. 2004/0199266 and 2010/0198204 and 2010/0198282; in U.S. patent application Ser. Nos. 12/970,312 and 12/970,347; and in U.S. Provisional Application Nos. 61/497,761, the disclosure of each of which is incorporated herein by reference in its entirety. For example, the vestibular stimulation device comprises one or more thin film TEDs (including, but not limited to, those described in U.S. Pat. No. 6,300,150 and U.S. Patent Publication Nos. 2006/0086118 and 2007/0028956).

TEDs of the present invention may comprise any suitable material. For example, the TED(s) may comprise a thermoelectric material such as bismuth telluride. In some embodiments, the TED(s) comprise a P-type thermoelectric element and an N-type thermoelectric element that are electrically coupled in series and thermally coupled in parallel.

TEDs of the present invention may be of any suitable size/shape. In some embodiments, the TED(s) is/are of a generally rectangular shape, with typical rectangular areas being about 2×1 mm or about 5×2 mm or more and with a typical height profile of about 1.0 mm, about 0.65 mm or about 0.5 mm or less.

TEDs of the present invention may be configured to sense the temperature of the earpiece(s) and/or the heat sink(s) with which it is associated.

As will be appreciated by one of skill in the art, in those embodiments comprising a plurality of TEDs, the TEDs may be arranged in any suitable manner. For example, the TEDs may be positioned adjacent one another in a linear array, a two-dimensional array or a three-dimensional array (e.g., at a density of about 5, 10 or 20 per square centimeter to about 100, 200 or 400 per square centimeter or more).

As will be appreciated by one of skill in the art, in those embodiments comprising a plurality of TEDs, the TEDs may be thermally coupled to one another. For example, the TEDs may be thermally coupled to one another (e.g., through a common heat sink) such that thermal energy displaced by one TED can be at least partially offset by thermal energy displaced by another TED (e.g., by heating tissue with one TED while cooling adjacent tissue with an adjacent TED).

D. Heat Sink

The vestibular stimulation device may comprise one or more heat sinks. In some embodiments, at least one heat sink is thermally coupled to each earpiece. In some embodiments, each TED thermally coupled to an earpiece is thermally coupled between the earpiece and at least one heat sink. In some embodiments, the heat sink(s) may be thermally isolated from the earpiece(s) except insofar as they are thermally coupled to opposite sides of the TED(s). In those embodiments comprising a pair of earpieces, each earpiece may be thermally coupled to a separate heat sink and/or to a common heat sink.

Any suitable heat sink can be used to carry out the present invention, including, but not limited to, those described in U.S. Patent Publication Nos. 2010/0198204 and 2010/0198282; in U.S. patent application Ser. Nos. 12/970,312 and 12/970,347; and in U.S. Provisional Application Nos. 61/497,761, the disclosure of each of which is incorporated herein by reference in its entirety.

Heat sinks of the present invention may comprise any suitable material, including, but not limited to, metal alloys. For example, the heat sink(s) may comprise aluminum or an aluminum alloy (e.g., 6061 aluminum).

Heat sinks of the present invention may be of any suitable size/shape. In some embodiments, the heat sink(s) comprise(s) a plurality of fins. Such fins may be from about 1 to about 500 mm in height, preferably about 1 to about 100 mm. In some embodiments, each heat sink weighs between about 30 grams and about 70 grams.

Heat sinks of the present invention may be passively and/or actively cooled. For example, each heat sink may be associated with one of more fans configured to increase air flow over the heat sink, thereby facilitating heat dissipation from the heat sink.

E. Sensors

The vestibular stimulation device may comprise one or more sensors. In some embodiments, the sensor(s) is/are configured to transmit controller feedback data, data associated with the delivery of one or more thermal waveforms to the vestibular system and/or the nervous system of a patient and/or data associated with the fit of one or more earpieces to the controller. In some such embodiments, the controller is configured (e.g., with computer instructions (i.e., software)) to adjust one or more attributes of TED activation (e.g., magnitude, duration, wave pattern, etc.) in response to feedback data received from the sensor(s) with which it is associated. The sensor(s) may be configured to transmit data to the controller over any suitable wired or wireless communications channel, including, but not limited to, a LAN, the Internet, a public telephone switching network, Bluetooth, WLAN and the like.

Any suitable sensor can be used to carry out the present invention, including, but not limited to, those described in U.S. Pat. Nos. 7,578,793, 7,558,622, 7,396,330, 7,215,994, 7,197,357, 7,087,075 and 6,467,905; in U.S. Patent Publication No. 2010/0198282; in U.S. patent application Ser. Nos. 12/970,312 and 12/970,347; and in U.S. Provisional Application Nos. 61/497,761, the disclosure of each of which is incorporated herein by reference in its entirety. For example, the vestibular stimulation device may comprise one or more of a galvanic skin resistance sensor, a position sensor, a motion detector, a blood pressure sensor, a heart rate sensor, a blood gas level sensor, an electrocardiogram sensor, an electroencephalogram sensor, an electrooculogram sensor, an electronystragmography sensor, a breathing rate sensor, a nystagmus sensor and a temperature sensor. Numerous such sensors are known and can be operatively associated with the systems described herein in accordance with known techniques or variations thereof that will be apparent to those skilled in the art given the present disclosure.

In some embodiments, the vestibular stimulation device comprises one or more temperature sensors. In some such embodiments, the vestibular stimulation device comprises a temperature sensor configured to provide controller feedback data associated with the temperature of the heat sink, a temperature sensor configured to provide controller feedback data associated with the temperature of the earpiece, a temperature sensor configured to provide controller feedback data associated with the temperature of the ear canal of the patient and/or a temperature sensor configured to provide controller feedback data associated with the temperature of the inner ear of the patient. In some embodiments, each earpiece comprises a sensor (e.g., an infrared sensor) configured to detect the temperature of the inner ear.

F. Headband

The vestibular stimulation device may comprise a headband. In some embodiments, the headband is configured to position the earpiece(s) in the ear canal(s) of a patient. In some embodiments the headband is adjustable. It should be appreciated that, while the headband may be worn over the head, it may also be positioned under the chin, behind the head and/or over the ear(s).

Any suitable headband can be used to carry out the present invention, including, but not limited to, those described in U.S. patent application Ser. Nos. 12/704,872; 12/970,312 and 12/970,347; in U.S. Provisional Application Nos. 61/287,873; 61/303,984, 61/304,059 and 61/497,761, the disclosure of each of which is incorporated herein by reference in its entirety.

G. Operation.

As noted above with respect to FIG. 1, the vestibular stimulation device 1 may comprise a controller 11 that is operatively connected to a TED 13*a* that is thermally connected to an earpiece 12*a* that is configured so as to be insertable into the left ear canal of a patient and to a TED 13*b* that is thermally connected to an earpiece 12*b* that is configured so as to be insertable into the right ear canal of a patient. In some such embodiments, the controller 11 (e.g., a controller 11 as described above with respect to FIG. 14) is configured to enable a user to deliver one or more thermal waveforms to the vestibular system and/or the nervous system of a patient by:
 a) generating and/or modifying the parameters, indications and/or approvals of one or more thermal waveforms using the waveform module 11a;
 b) transmitting the generated/modified parameters, indications and/or approvals to the treatment module 11b and/or storing the generated/modified parameters, indications and/or approvals in the waveform database 11h;
 c) generating a prescription comprising a set of instructions for delivering one or more thermal waveforms to the vestibular system and/or the nervous system of the patient by:
  i) receiving one or more thermal waveforms from the waveform module 11a and providing instructions as to how each thermal waveform is to be administered to the patient using the treatment module 11b; or
  ii) selecting one or more thermal waveforms from the waveform database 11h and providing instructions as to how each thermal waveform is to be administered to the patient using the treatment module 11b;
 d) transmitting the generated prescription to the control module 11c and/or storing the generated prescription in the prescription database 11i; and/or
 e) delivering one or more thermal waveform(s) to the vestibular system and/or the nervous system of the patient by:
  i) receiving a prescription comprising a set of instructions for delivering one or more thermal waveforms to the vestibular system and/or the nervous system of the patient from the treatment module 11b and activating the TEDs 13a, 13b in accordance with the instructions; or
  ii) retrieving a prescription comprising a set of instructions for delivering one or more thermal waveforms to the vestibular system and/or the nervous system of the patient from the prescription database 11i and activating the TEDs 13a, 13b in accordance with the instructions.

In some such embodiments, the controller 11 (e.g., a controller 11 as described above with respect to FIG. 15) is configured to enable a user to deliver one or more thermal waveforms to the vestibular system and/or the nervous system of a patient by:
 a) receiving and/or retrieving the parameters, indications and/or approvals of one or more thermal waveforms from a registry and/or a portable memory device using the network module 11d;
 b) storing the received/retrieved parameters, indications and/or approvals in the waveform database 11h and/or transmitting the received/retrieved parameters, indications and/or approvals to the waveform module 11a and/or the treatment module 11b;
 c) generating and/or modifying the parameters, indications and/or approvals of one or more thermal waveforms using the waveform module 11a;
 d) transmitting the generated/modified parameters, indications and/or approvals to the treatment module 11b and/or storing the generated/modified parameters, indications and/or approvals in the waveform database 11h;
 e) receiving and/or retrieving a prescription from a registry and/or a portable memory device using the network module 11d;
 f) storing the received/retrieved prescription in the prescription database 11i and/or transmitting the received/retrieved prescription to the treatment module 11b and/or the control module 11e;
 g) generating a prescription comprising a set of instructions for delivering one or more thermal waveforms to the vestibular system and/or the nervous system of the patient by:
  i) receiving one or more thermal waveforms from the network module 11d and/or the waveform module 11a and providing instructions as to how each thermal waveform is to be administered to the patient using the treatment module 11b;
  ii) selecting one or more thermal waveforms from the waveform database 11h and providing instructions as to how each thermal waveform is to be administered to the patient using the treatment module 11b;
  iii) receiving a prescription from the network module 11d and modifying the instructions as to how each thermal waveform is to be administered to the patient using the treatment module 11b;
  ii) retrieving a prescription from the prescription database 11i and modifying the instructions as to how each thermal waveform is to be administered to the patient using the treatment module 11b;
 h) transmitting the generated prescription to the control module 11e and/or storing the generated prescription in the prescription database 11i; and/or
 i) delivering one or more thermal waveform(s) to the vestibular system and/or the nervous system of the patient by:
  i) receiving a prescription comprising a set of instructions for delivering one or more thermal waveforms to the vestibular system and/or the nervous system of the patient from the treatment module 11b and activating the TEDs 13a, 13b in accordance with the instructions; or
  ii) retrieving a prescription comprising a set of instructions for delivering one or more thermal waveforms to the vestibular system and/or the nervous system of the patient from the prescription database 11i and activating the TEDs 13a, 13b in accordance with the instructions.

Also as noted above with respect to FIG. 1, the vestibular stimulation device 1 may further comprise a pair of sensors 14a, 14b, wherein one of the sensors 14a is operatively connected to the earpiece 12a that is configured so as to be insertable into the left ear canal of the patient, wherein the other sensor 14b is operatively connected to the earpiece 12b that is configured so as to be insertable into the right ear canal of the patient and wherein the controller 11 is operatively connected to each of the sensors 14a, 14b via a wireless connection 17a, 17b. In some such embodiments, controller 11 (e.g., a controller 11 as described above with respect to FIG. 15) is configured such that controller feedback data received from the sensors (e.g., data associated with the temperature of the earpiece(s), data associated with the temperature of the patient's ear canal(s), data associated with the rate at which an earpiece is warmed/cooled in response to a warming/cooling stimulus, etc.) is used by the control module 11c to ensure that the appropriate thermal waveform(s) is delivered to the vestibular system and/or the nervous system of the patient (e.g., the control module 11c may be configured to increase/decrease the magnitude of TED 13a activation if/when controller feedback data from the sensor 14b associated with the left earpiece 12a indicates that the temperature of the earpiece 12a is not at the appropriate temperature given the parameters of the prescribed thermal waveform).

Figure 19:
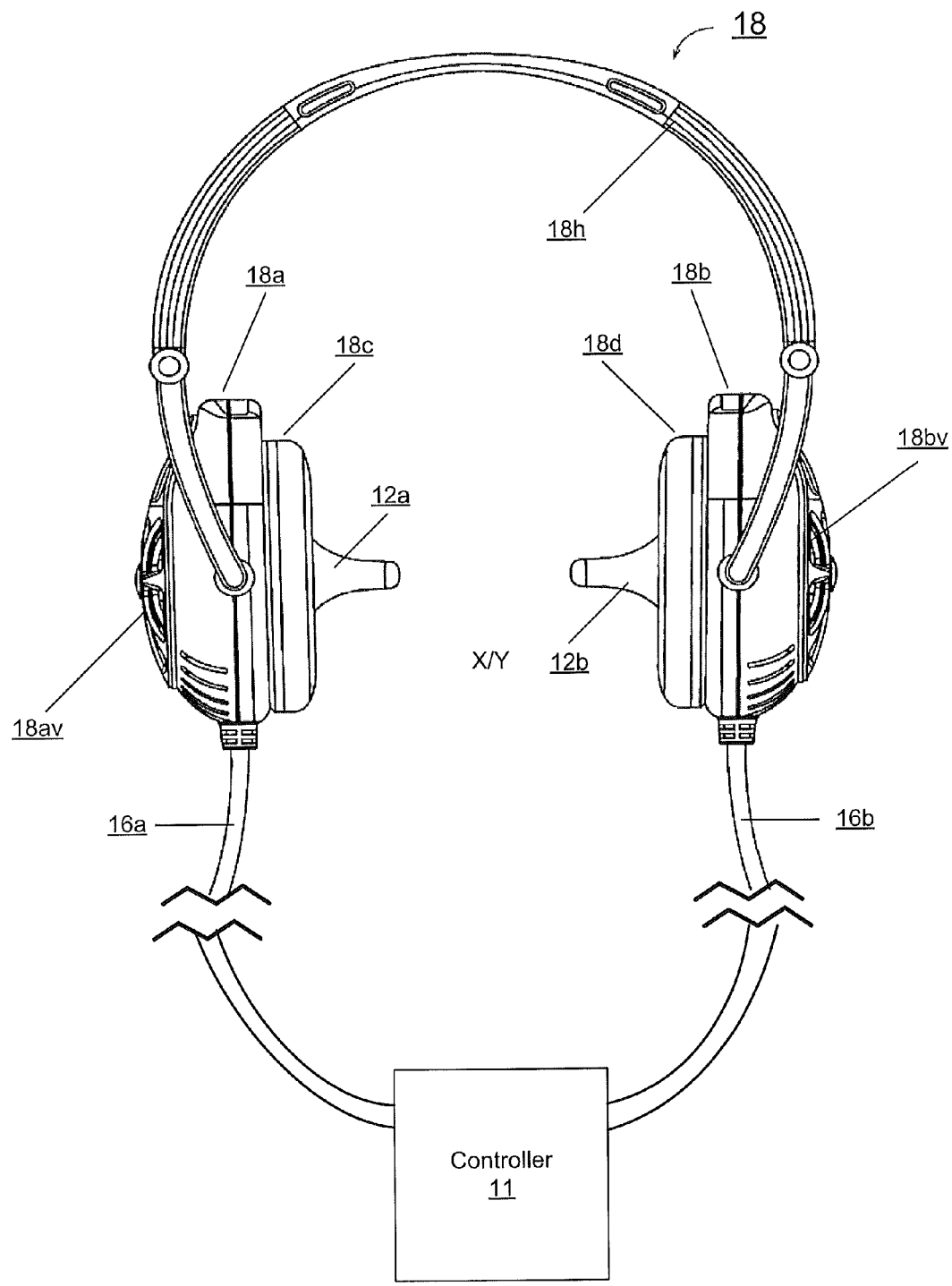
FIG. 19 is a perspective view of a vestibular stimulation device according to some embodiments of the present invention.

As shown in FIG. 19, in some embodiments, the vestibular stimulation device comprises a controller 11 and a headset 18. As shown therein, the headset may comprise a headband 18h configured to position a first earpiece 12a in the left ear canal of a patient and to position a second earpiece 12b in the right ear canal of the subject; a first heat sink thermally coupled to the first earpiece 12a (as shown, the first heat sink is concealed within a first housing 18a, the ventilation apertures 18av of which allow for heat exchange between the first heat sink and the ambient environment), a second heat sink thermally coupled to the second earpiece 12b (as shown, the first heat sink is concealed within a second housing 18b, the ventilation apertures 18bv of which allow for heat exchange between the second heat sink and the ambient environment); a first TED thermally coupled between the first earpiece 12a and the first heat sink (as shown, the first TED is concealed within the first housing 18a); a second TED 13b thermally coupled between the second earpiece 12b and the second heat sink (as shown, the second TED 13b is concealed within the second housing 18b); a first sensor operatively connected to the first TED and the controller 11 (as shown, the first sensor is concealed within the first earpiece 12a; a second sensor operatively connected to the second TED and the controller 11 (as shown, the second sensor is concealed within the second earpiece 12a; a first cushion 18c connected to the first housing 18a and a second cushion 18d connected to the second housing 18b. In some such embodiments, the controller is operatively connected to the first and second TEDs by a pair of thermal stimulation leads 16a, 16b. In some such embodiments, the controller 11 is operatively connected to the first and second sensors via a wireless connection (e.g., via a radiofrequency transceiver or a Bluetooth connection). In some such embodiments, one or both of the first and second cushions 18c, 18d is configured to be adjustable (e.g., the first cushion 18c and/or the second cushion 18d may comprise an inner chamber that may be inflated/deflated to adjust the firmness and/or the size of the cushion, thereby allowing a user to adjust the fit of the vestibular stimulation device (i.e., to adjust how far the first and/or second earpiece 12a, 12b inserts into the patient's ear canal by increasing/decreasing the amount of gas/liquid in the inner chamber)).

Figure 20:
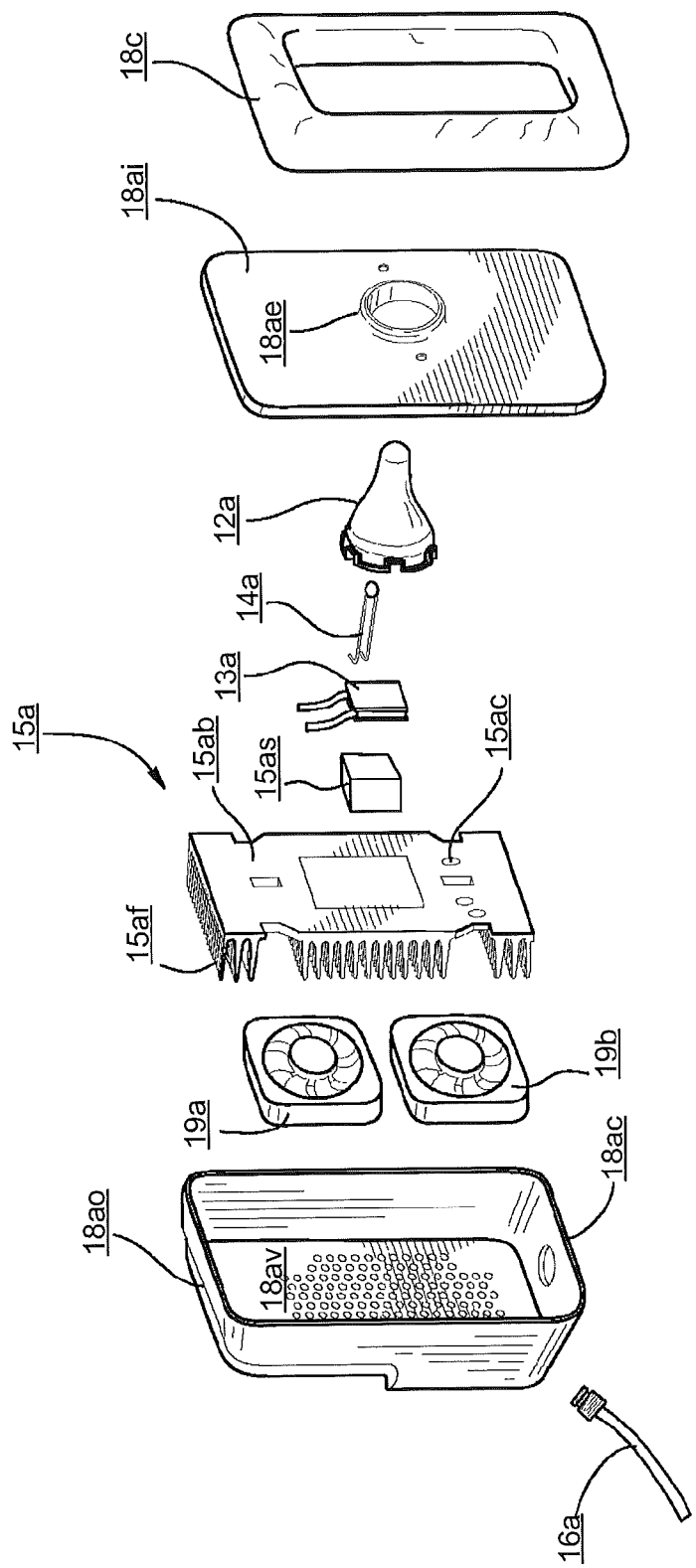
FIG. 20 is an exploded view of a vestibular stimulation device headset housing according to some embodiments of the present invention.

As discussed above with respect to FIG. 19, in some embodiments of the present invention, various components of the vestibular stimulation device 1 are concealed within the first and/or second housings 18a, 18b. FIG. 20 provides an exploded view of a first housing 18a according to some embodiments of the present invention. As shown therein, the first housing 18a may conceal a first TED 13a; a first sensor 14a; a first heat sink 15a, said first heat sink 15a comprising a first heat sink base 15ab, a first heat sink spacer 18 as, a plurality of fins 15af and a plurality of cable apertures 15ac to provide passageways for one or more wires and/or cables (e.g., one or wires connected to the first TED 13a and/or one or wires connected to the first sensor 14a), and two heat dissipating fans 19a, 19b. The first earpiece 12a may be thermally connected to the first TED 13a and the first heat sink 15a as shown in FIGS. 21A-21B. The first TED 13a may be positioned on the top surface 15as' of the heat sink spacer 15as and inside the base cavity 120a of the first earpiece 12a and may be adhered to the heat sink 15a and/or the first earpiece 12a using a thermally conductive adhesive (e.g., silver paste). The first sensor 14a may be positioned inside the tip cavity 121 of the first earpiece 12a and may be configured to provide controller feedback data associated with the temperature of the first earpiece 12a to the controller (as discussed above). Upon activation, the heat dissipating fans 19a, 19b may facilitate the transfer of heat between the first heat sink 15a and the ambient environment by increasing air flow across the first heat sink 15a. The outer member 18ao of the first housing 18a comprises ventilation apertures 18av to further facilitate the transfer of heat between the first heat sink 15a and the ambient environment (by increasing the flow of air across the first heat sink 15a) and a cable aperture 18ac to provide a passageway for one or more wires and/or cables (e.g., the thermal stimulation lead 16a and/or one or wires connected to the first sensor 14a). The inner member 18ai of the first housing 18a comprises an earpiece aperture 18ae through which the distal portion of the first earpiece 12a protrudes. As will be appreciated by one skilled in the art, the second housing 18b may be similarly configured.

3. WAVEFORM STIMULUS AND TREATMENT SESSIONS

"Waveform" or "waveform stimulus" as used herein refers to the thermal stimulus (heating, cooling) delivered to the ear canal of a subject through a suitable apparatus to carry out the methods described herein. "Waveform" is not to be confused with "frequency," the latter term concerning the rate of delivery of a particular waveform. The term "waveform" is used herein to refer to one complete cycle thereof, unless additional cycles (of the same, or different, waveform) are indicated. As discussed further below, time-varying waveforms are preferred over constant temperature applications in carrying out the present invention.

In some embodiments, the waveform stimulus is an actively controlled waveform or actively controlled time-varying waveform. "Actively controlled waveform" or "actively controlled time-varying waveform" as used herein refers to a waveform stimulus in which the intensity of the stimulus or temperature of the earpiece delivering that stimulus, is repeatedly adjusted, or substantially continuously adjusted or driven, throughout the treatment session, typically by control circuitry or a controller in response to active feedback from a suitably situated temperature sensor (e.g., a temperature sensor mounted on the earpiece being driven by a thermoelectric device), so that drift of the thermal stimulus from that which is intended for delivery which would otherwise occur due to patient contact is minimized.

In general, a waveform stimulus used to carry out the present invention comprises a leading edge, a peak, and a trailing edge (see, e.g., FIG. 22). If a first waveform stimulus is followed by a second waveform stimulus, then the minimal stimulus point therebetween is referred to as a trough.

The first waveform of a treatment session is initiated at a start point, which start point may be at or about the subject's body temperature at the time the treatment session is initiated (typically a range of about 34 to 38 degrees Centigrade, around a normal body temperature of about 37 degrees Centigrade (temperature changes and amplitudes are given with reference to normal body temperature herein, unless indicated otherwise). The lower point, 34, is due to the coolness of the ear canal. It typically will not be above about 37 unless the patient is febrile). Note that, while the subject's ear canal may be slightly less than body temperature (e.g., about 34 to 36 degrees Centigrade), the starting temperature for the waveform is typically body temperature (the temp of the inner ear), or about 37 degrees Centigrade. In some embodiments, however, the temperature of the treatment device may not have equilibrated with the ear canal prior to the start of the treatment session, and in such case the start point for at least the first waveform stimulus may be at a value closer to room temperature (about 23 to 26 degrees Centigrade).

The waveform leading edge is preferably ramped or time-varying: that is, the amplitude of the waveform increases through a plurality of different temperature points over time (e.g., at least 5, 10, or 15 or more distinct temperature points, and in some embodiments at least 50, 100, or 150 or more distinct temperature points, from start to peak). The shape of the leading edge may be a linear ramp, a curved ramp (e.g., convex or concave; logarithmic or exponential), or a combination thereof. A vertical cut may be included in the waveform leading edge, so long as the remaining portion of the leading edge progresses through a plurality of different temperature points over time as noted above.

The peak of the waveform represents the amplitude of the waveform as compared to the subject's body temperature. In general, an amplitude of at least 5 or 7 degrees Centigrade is preferred for both heating and cooling waveform stimulation. In general, an amplitude of up to 20 or 22 degrees Centigrade (below body temperature) is preferred for cooling waveform stimulation. In general, an amplitude of up to 8, 10 or 12 degrees Centigrade (above body temperature) is preferred for heating waveform stimulus. The peak of the waveform may be truncated (that is, the waveform may reach an extended temperature plateau), so long as the desired characteristics of the leading edge, and preferably trailing edge, are retained. For heating waveforms, truncated peaks of long duration (that is, maximum heat for a long duration) are less preferred, particularly at higher heats, due to potential burning sensation.

The waveform trailing edge is preferably ramped or time-varying: that is, the amplitude of the waveform decreases through a plurality of different temperature points over time (e.g., at least 5, 10, or 15 or more distinct temperature points, or in some embodiments at least 50, 100, or 150 or more distinct temperature points, from peak to trough). The shape of the trailing edge may be a linear ramp, a curved ramp (e.g., convex or concave; logarithmic or exponential), or a combination thereof. A vertical cut may again be included in the waveform trailing edge, so long as the remaining portion of the trailing edge progresses through a plurality of different temperature points over time as noted above.

The duration of the waveform stimulus (or the frequency of that waveform stimulus) is the time from the onset of the leading edge to either the conclusion of the trailing edge or (in the case of a vertically cut waveform followed by a subsequent waveform). In general, each waveform stimulus has a duration, or frequency, of from one or two minutes up to ten or twenty minutes.

A treatment session may have a total duration of one, two, five or ten minutes, up to 20 or 40 minutes, or even 60 or 80 minutes, or more, depending on factors such as the specific waveform or waveforms delivered, the patient, the condition being treated, etc. In a treatment session, a plurality of waveforms may be delivered in sequence (see, e.g. FIG. 22). In general, a treatment session will comprise 1, 2 or 3 waveforms, up to about 10 or 20 waveforms delivered sequentially. Each individual waveform may be the same, or different, from the other (see, e.g., FIG. 22). When a waveform is followed by a subsequent waveform, the minimum stimulus point (minimum heating or cooling) between two consecutive peaks is referred to as the trough. Like a peak, the trough may be truncated, so long as the desired characteristics of the trailing edge, and the following next leading edge, are retained. While the trough may represent a return to the subject's current body temperature, in some embodiments minor thermal stimulation (cooling or heating; e.g, by 1 or 2 degrees up to 4 or 5 degrees Centigrade) may continue to be applied at the trough (or through a truncated trough). The treatment sessions may be continuous, or may be interrupted by short pauses of up to 1 or 2 minutes, or more.

Treatment sessions are, in some embodiments, once a day, though in some embodiments more frequent treatment sessions (e.g. two or three times a day) may be employed. Day-to-day treatments may be by any suitable schedule: every day; every other day; twice a week, etc., as needed by the subject. The overall pattern of treatment is thus typically chronic (in contrast to "acute," as used in one-time experimental studies).

In some embodiments, the time-varying thermal waveforms are sufficient to induce nystagmus over a time of at least four, five, ten, or fifteen minutes, or more, up to a time of thirty minutes or one hour, or more. Nystagmus may be as measured by videonystagmography and/or by electronystagmography, and may increase or decrease or even cease for brief periods over the treatment period, but is substantially present for the treatment period.

4. THERMAL MODEL OF CALORIC VESTIBULAR STIMULATION

The thermodynamic details of how the cupola is actually stimulated, the ultimate cause of excitation or inhibition of a given branch of the vestibulocochlear nerve, is important in describing the principles of the present invention.

The temporal bone, which overlies the inner ear, is filled with voids (filled with cells and fluids but sometimes just air) leading to a net thermal conductivity that may be lower than that of dense bone. Zeigmeister & Bock (*Acta Otolaryngologica* 88, 105-9 (1979)) indicate that the effective thermal diffusivity will vary in patients based on the degree of pneumatization of the temporal bone. However, this is generally based on observations of the induction of nystagmus, which is a secondary effect of the first-order stimulation by direct afferents of the vestibular nerve.

Compact bone in the region of interest provides the most efficient thermal pathway. X-rays of the region indicate that there are high conductivity thermal paths (in 3-dimensions) that compete with paths through the bone with air pockets. In the model below, a value of thermal diffusivity closer to that of compact bone is chosen. To initiate caloric vestibular stimulation, the most important "target" is the most distal extent of the external auditory meatus (ear canal). Air is an effective thermal insulator and therefore the air gap in the middle ear (variously referred to as the mastoid antrum or cavity, epitympanic cavity) is not the primary pathway for thermal conduction from the ear canal to the horizontal (also called lateral) semicircular canal (however, there is some evidence of radiative cooling of the distal wall of the mastoid cavity during the initial induction of CVS). That is, the temporal bone is the primary thermal conduit and thus the CVS thermal source should be in intimate contact with it to ensure good thermal transfer.

The obvious boundary for the CVS probe is the tympanic membrane, which must not be pierced. For water and air calorics, the entire ear canal is filled and this is advantageous in terms of contact with the temporal bone (though one does have to guard against the development of stagnant eddies against the ear drum). Once the CVS source starts to act on the temporal bone, the thermal wave travels around the epitympanic cavity (most strongly along inner surface, which is compact bone, at first) until it reaches the far side of the cavity, above the point where the stapes contacts the oval window. The horizonal (also called lateral) semicircular canal can be viewed as a ring embedded in bone that has a point of close tangency to the epitympanic cavity. It is this section of that canal that experiences the effect of the thermal wave first. As the thermal wave progresses, it moves deeper into the distal side of the epitympanic cavity and ultimately reaches the distal side of the horizontal canal.

The object of CVS is to develop (and maintain) a temperature difference across the diameter of the horizontal canal. The speed with which the temperature gradient is experienced by the horizontal canal depends on the cooling effects of blood entering and leaving the region and any individual variation in the anatomy of a patient. The fit of the earpiece is an important as well. It should be noted that the endolymph in the other two semicircular canals and in the utricle and saccule may also develop convection currents that lead to altered phasic firing, but for simplicity we focus on the horizontal canal.

A large caloric stimulus leads to a shorter duration of stimulation. A robust thermal wave will, more quickly, flow deeper into the boney housing of the horizontal canal and the temperature gradient across it will be nullified more quickly. The various thermal models in the literature (e.g., Proctor et al., *Acta Otolaryngol* 79, 425-435 (1975)) simplify the real anatomy even further and consider a layer of skin on top of a honey region that contains the semicircular canal.

Moving to the semicircular canals themselves, there are anatomic features of interest for modeling CVS. The inner wall of each canal is a tough, membranous structure, which contains the endolymph (The Vestibular System; Highstein et al. editors, Springer (New York), 2004). The membranous tube is connected to a layer of lamellar bone, which forms the hard (enduring) portion of the canal. Between the honey layer and membranous layer is another fluid called the perilymph. Therefore the literature refers to a honey and a membranous labyrinth when describing the semicircular canals. The membranous tube is thought not to deform appreciably and therefore is viewed as being rigidly attached to the temporal bone and moves with the head. The endolymph, however, moves "independently" in the canal. Note that the cupula, a gelatinous diaphragm in the ampulla (the widened portion of the semicircular canal), is a complete barrier in the canal and thus endolymph cannot truly circulate around the loop of the canal. Hence the cupula is pushed to one side or the other by movement of the endolymph. Intuitively, this movement is most easily understood by thinking about sudden rotation about the vertical axis of the body. The endolymph will "slosh up against" the cupula, pushing it in the direction of motion of the endolymph. As we will see, the effects of the present invention on the endolymph is less intuitive and involves complexities.

A key feature of the movement of the cupula is that in one direction it leads to an increase in the firing rate of the hair cells in the crista (innervated end of the ampulla) whereas movement in the opposite direction leads to a decrease in the rate (relative to a tonic or steady-state level of roughly 100 Hz). Thus there is an inhibitory or excitatory influence on the tonic firing rate of the afferent vestibular nerve innervating the horizontal canal based on the direction of endolymph movement. This influence is, indeed, what leads to the onset of nystagmus during CVS with a directional dependence on the temperature of the stimulus, though nystagmus is decoupled (in time) from the initial activation of the brainstem.

One of the complex aspects of the collection of semicircular canals is that they have fluid connections between them. Therefore, they can exchange endolymph. This means that CVS to the horizontal canal can actually have effects on the other two canals (anterior and posterior). A further complication of the naming of the anatomy is that the horizontal canal is not really horizontal, but tilts by approximately 20 degrees so that it is high on the anterior side of the head. Thus, when a patient tilts back 70 degrees (the head lying on a 20 degree incline above a horizontal surface), the "horizontal" canal is then oriented so that the loop is roughly vertical. For diagnostic CVS, the patient is often reclined in this manner because it is thought that the effect of CVS is maximized as a result of receiving the stimulation while in this posture.

The thermodynamics of endolymph flow in the semicircular canals has been the subject of several papers. In classical fluid mechanics, a mathematical formalism for non-compressible fluids called the Navier-Stokes equations must be used to understand flow dynamics. In practice, this is a complicated undertaking and it is often necessary to resort to numerical modeling. Here, we present an idealized model of the horizontal SCC and how thermodynamics influences the character of neuro stimulation.

FIG. 23 shows an idealized form of the horizontal SCC (stippled) that is being heated on one side (wavy lines) and cooled on the other (cross-hatched). The cupula is shown in dark grey and the arrow represent endolymph flow. On the right, an expanded region representing the ampulla has been added. When the endolymph is heated, it will rise (less dense, or expanded in volume) and push on the center of the cupula. There is a small boundary layer of endolymph that adheres more strongly to the sidewall of the canal and we ignore that here. Once the endolymph hits the cupula, it will exert most of the distortion centrally because the cupula is most easily deformed there and because there is a circulatory aspect to the convection driven endolymph: rise up the center and fall down along the sides. The bulge of the ampulla introduces a sudden expansion in volume, which will complicate the movement of convection driven endolymph (shown conceptually on the right). The same basic convective flow will occur, but the ampulla will most likely create more turbulence and therefore, potentially, more complicated low amplitude movement of the cupula. In analyzing nystagmus, a simple view that considers only the upward displacement of the cupula is adopted (and that's reasonable for the gross nystagmic movement). Most likely the cupula exhibits time-varying "flutter," especially for lower amplitude distortion. Under rotational stimulus, the cupula is pressed to one side and then rebounds. Caloric stimulation, especially when the temperature gradient is weak or changing, sets up a much more complicated series of deformational forces. Therefore one would expect a complex time series of excitatory and inhibitory firings of the hair cells (at the "base" of the cupula called the crista). It is again important to note the great sensitivity to motion of the cupula and its ability to respond across a wide dynamic range of impulsive forces (big bumps versus subtle head movements). Further, as noted earlier, the three SCC's do communicate by fluid connections (restricted ones), and it is reasonable to expect that some level of attenuated stimulation of the anterior and posterior SCC's will occur both directly (they respond to caloric stimulation) and in conjunction with stimulation of the horizontal canal. And as noted, endolymph motion in the utricle and saccule, set up by convection currents, may also lead to changes in the phasic firing rates of some vestibular nerve afferents.

Let us briefly consider the case of stimulation of the horizontal SCC in a less favorable position for CVS-generated nystagmus—that is, when the head is tilted somewhat forward (the horizontal canal is close to being horizontal). The literature seems to maintain that inducing nystagmus at a 20° forward tilt will not occur. However, even in that case one would expect some time-varying deformation of the cupula due to turbulence in the endolymph.

When the horizontal canal is close to the horizontal position in the gravitational field (referring again to the analogy of a bubble in fluid), the heated endolymph will still tend to move up to the cupula and deform it. There is some evidence in the literature that the hair cells fire with a chaotic time pattern, suggesting again that turbulence may cause some "flutter" of the cupula due to convection currents in the endolymph.

Heating Versus Cooling Caloric Vestibular Stimulation.

Endolymph, the active fluid in the vestibular labyrinth, is predominantly water. Water expands and contracts in a nonlinear fashion with temperature. A larger change in volume occurs at temperature deltas above body temperature (37° C.) than below it. For example, to achieve the same change in volume in going from 37° C. to 47° C., one needs to go from 37° C. to 23° C. Since volume change corresponds to the displacement of the cupula in the horizontal semicircular canal, it corresponds to the magnitude of the phasic frequency shift away from the tonic firing frequency of the hair cells, which innervate the vestibular nerve.

Additionally, a cold caloric stimulus acts to reduce the firing frequency whereas a warm caloric stimulus increases it. Taking the tonic firing rate to be roughly 100 Hz, cold CVS can only, maximally, reduce the firing rate to close to 0 Hz. Warm CVS, on the other hand, can increase the phasic firing frequency beyond 200 Hz, perhaps to as high as 400 Hz. This creates an additional asymmetry that favors warm CVS in terms of the intensity of stimulus to the cochlear nerve.

Zhou et al. (*J Neurochem* 95, 221-229 (2005)) posit that stimulation of the fastigial nucleus has a neuroprotective effect by frustrating apoptosis in mitochondria. CVS stimulates the fastigial nucleus. The goal is to prescribe properly titrated treatment by the present invention for patients across a range of diseases. The fMRI study by Marcelli et al. ("Spatio-temporal pattern of vestibular information processing after brief caloric stimulation," *Eur J Radiol* 70, 312-316 (2009)) showed activation in the brainstem, cerebellum, thalamus, and insular cortex after a brief (1.5 second) cold caloric stimulation. The activation lasted for more than 200 seconds and was most noticeable in the brainstem. Further, this study did not see a correlation between activation and the onset time for nystagmus (though they did not rule this out completely).

There are three primary modes of carrying out the present invention: (1) time varying excitatory; (2) time varying inhibitory; and (3) time varying excitatory and inhibitory. The magnitude of the stimulus (i.e., the temperature difference with respect to body temperature) is not independent of the time over which the influence of that temperature delta will continue once the external thermal stimulus ceases. For example, the application of a 4° C. stimulus for 1 minute will result in a large magnitude effect on the endolymph that will frustrate a rapid change back to a higher temperature. As noted above, such a pulse would lead to faster adaptation and would then become more variable as the endolymph warms and develops turbulent eddies. A lower magnitude stimulus can be varied more quickly, since the system is not driven so far out of equilibrium.

Large amplitude, square waveform caloric vestibular stimulation results in a decreased ability to rapidly vary the "sign" (inhibitory/excitatory) of hair cell stimulation and leads to faster adaptation effects (return towards tonic hair cell firings) and therefore negates the advantage of longer CVS delivery duration. The present invention provides a way to produce a full range of cupular stimulation patterns so as to effectively titrate chronic treatment protocols for patient benefit without losing efficacy due to adaptation and without inducing undesirable side effects that can accompany the use of current irrigator-type CVS devices.

5. SUBJECTS FOR TREATMENT

Subjects may be treated with the present invention for various reasons. In some embodiments, disorders for which treatment may be carried out include, include, but are not limited to, headaches, depression, anxiety (e.g. as experienced in post-traumatic stress disorder ("PTSD") or other anxiety disorders), spatial neglect, Parkinson's disease, seizures (e.g., epileptic seizures), diabetes (e.g., type II diabetes), etc. Subjects may be treated to enhance cognition or cognitive reserve, to enhance long term memory, to enhance short term memory, to enhance long term memory, etc.

Additional disorders and conditions that can be treated by the methods and systems of the present invention include, but are not limited to, neuropathic pain (e.g., migraine headaches), brain injury (acute brain injury, excitotoxic brain injury, traumatic brain injury, etc.), spinal cord injury, body image or integrity disorders (e.g., spatial neglect), tinnitus, visual intrusive imagery, neuropsychiatric disorders (e.g. depression), bipolar disorder, neurodegenerative disorders (e.g. Parkinson's disease), asthma, dementia, insomnia, stroke, cellular ischemia, metabolic disorders, (e.g., diabetes), post-traumatic stress disorder ("PTSD"), addictive disorders, sensory disorders, motor disorders, and cognitive disorders.

"Headache" as used herein includes, but is not limited to, primary headaches such as migraine headaches, tension-type headaches, trigeminal autonomic cephalagias, and other primary headaches; as well as secondary headaches. See, e.g., International Headache Society Classification ICHD-II.

"Migraine headaches" that may be treated by the invention may be acute or chronic, and unilateral or bilateral. The migraine headache may be of any type, including but not limited to migraine with aura, migraine without aura, hemiplegic migraine, ophthalmoplegic migraine, retinal migraine, basilar artery migraine, abdominal migraine, vestibular migraine, probable migraine, etc.

"Vestibular migraine" as used herein refers to migraine with associated vestibular symptoms, including but not limited to head motion intolerance, unsteadiness, dizziness, and vertigo. "Vestibular migraine" as used herein includes, but is not limited to, those conditions sometimes also referred to as vertigo with migraine, migraine associated dizziness, migraine-related vestibulopathy, migrainous vertigo, and migraine-related vertigo. See, e.g., R. Teggi et al., *Headache* 49, 435-444 (2009).

"Tension-type headache" that may be treated by the invention include infrequent episodic tension-type headache, frequent episodic tension-type headache, chronic tension-type headache, and probable tension-type headache, etc.

"Trigeminal autonomic cephalagias" that may be treated by the invention include cluster headache, paroxysmal hemicranias, short-lasting unilateral neuralgiform headache attacks with conjunctival injection and tearing, and probable trigeminal autonomic cephalagias.

"Other primary headaches" that may be treated by the invention include primary cough headache, primary exertional headache, primary headache associated with sexual activity, hypnic headache, primary thunderclap headache, hemicranias continua, and new daily-persistent headache.

"Cluster headache", also sometimes known as "suicide headache," is considered different from migraine headache. Cluster headache is a neurological disease that involves, as its most prominent feature, an immense degree of pain. "Cluster" refers to the tendency of these headaches to occur periodically, with active periods interrupted by spontaneous remissions. The cause of the disease is currently unknown. Cluster headaches affect approximately 0.1% of the population, and men are more commonly affected than women (in contrast to migraine headache, where women are more commonly affected than men).

Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vaculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Metabolic disorders that may be treated by the present invention include diabetes (particularly type II diabetes), hypertension, obesity, etc.

Addiction, addictive disorders, or addictive behavior that may be treated by the present invention includes, but is not limited to, alcohol addiction, tobacco or nicotine addiction (e.g., using the present invention as a smoking cessation aid), drug addictions (e.g., opiates, oxycontin, amphetamines, etc.), food addictions (compulsive eating disorders), etc.

In some embodiments, the subject has two or more of the above conditions, and both conditions are treated concurrently with the methods and systems of the invention. For example, a subject with both depression and anxiety (e.g., PTSD) can be treated for both, concurrently, with the methods and systems of the present invention.

Without wishing to be limited to any one theory of the invention, in some embodiments the disorder may be treated through activation of the fastigial nucleus and corresponding mitochondrial activation by the methods described herein. Such disorders, treated in such manner, are referred to as "mitochondrial disorders" or "mitochondrial dysfunction disorders" as discussed further below.

6. WAVEFORM TITRATION OVER TIME

As noted above, in the present invention, the waveform stimulus is preferably titrated over time in the course of treating a particular patient. Titration can be carried out by any suitable technique.

Figure 24:
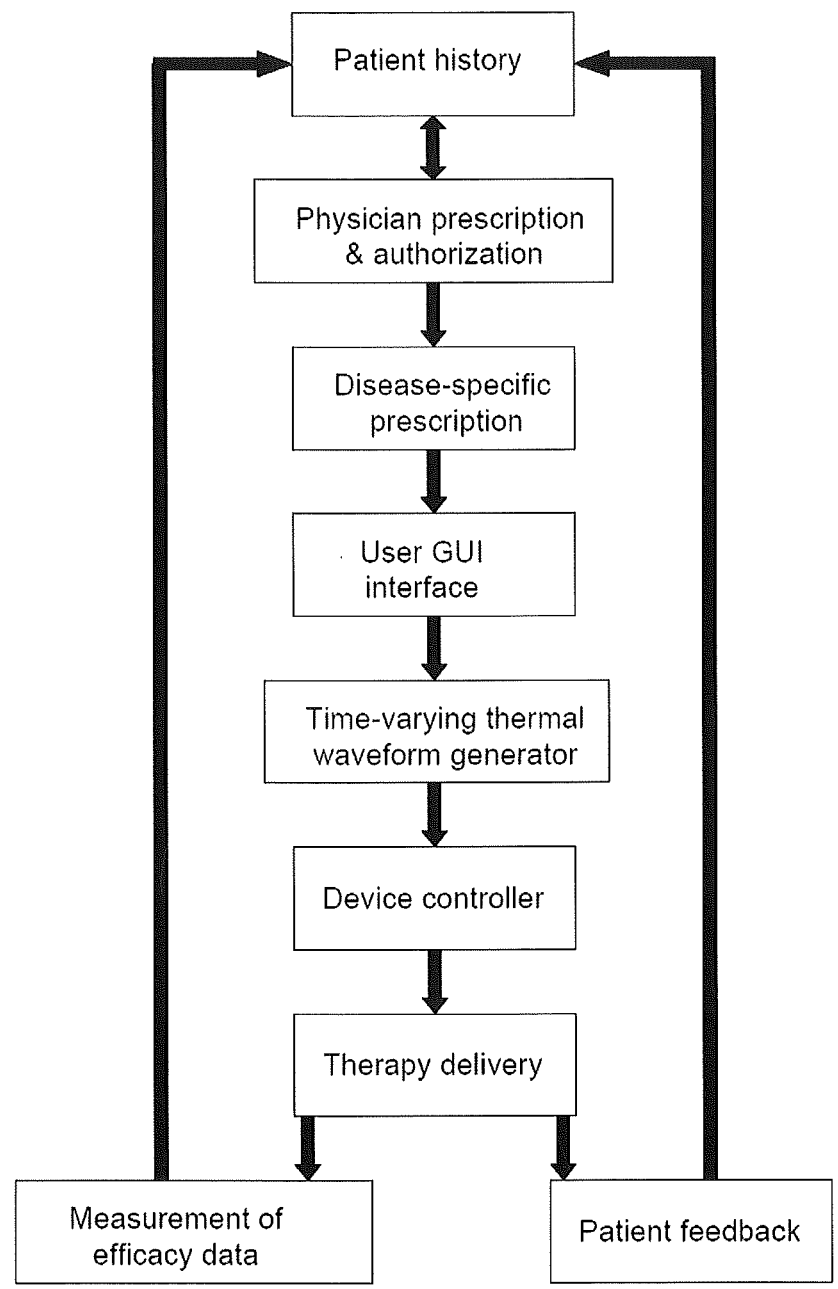
FIG. 24. A schematic diagram of a hierarchical flow of activities around the initiation and continuation of caloric vestibular stimulation (CVS).

In one embodiment as shown in FIG. 24, a hierarchical flow of activities around the initiation and continuation of CVS therapy exists. A qualified physician starts by taking a patient history and establishes that the patient's disease is appropriate for CVS therapy. That information is stored in the patient history database module. The physician then accesses a library of existing treatment waveforms appropriate to the patient's disease. The physician gathers biometric data on the patient, which could include height and weight, but also may include results of a direct measurement of the thermal conduction parameters from that patient's ear canal to the inner ear (facilitated, e.g., by an IR sensor that assesses the temperature of the inner ear over time as a function of the applied thermal waveform to the ear canal). The physician thus modifies timing parameters, etc. of the disease-specific thermal waveform to better match the physiology of the patient.

The physician downloads the CVS prescription to the patient GUI interface on the CVS treatment unit. This may be done in the physician's clinic or remotely via a phone, internet, or wireless transfer protocol. The patient GUI interface transfers the prescription data to a time-varying thermal waveform generator, which in turn enables the CVS device controller. The CVS device is then activated and will, as frequently as daily, or even several times a day, enable the patient to receive a therapeutic treatment. After treatment, the patient will be prompted to input feedback via the patient GUI interface with respect to the efficacy of treatment. Additionally, the physician may request, at a frequency of his or her choosing, patient data on efficacy and/or side effects (examples of which include, but are not limited to, magnetic resonance imaging data, EEG data, blood pressure data, pulse data, pulse oximetry data, galvanic skin response data, blood, saliva, or urine chemistry data, nystagmography data, blood glucose data, cerebral blood flow data (e.g., as determined by any suitable technique such as ultrasound or transcranial Doppler sonography) observed parameters such as facial expressions, verbal or written responses to interviews, etc.). The patient feedback and measurement data is then entered into the patient history database and accessed by the physician (e.g., to confirm patient compliance with a particular course of treatment).

Based on the patient's progress with CVS therapy, the physician may choose to increase the level or duration of CVS stimulus, to decrease the level or duration of CVS stimulus, to alter the stimulus waveform, combinations of the foregoing, to continue at the current stimulus level and duration, or stop therapy. Any modifications to the therapy prescription will be input to the patient history database and lead to the creation of a new prescription for successive patient treatments. In some embodiments the physician will review the patient's progress and decide whether to extend the prescription, for example on a 30-day cycle.

Figure 25:
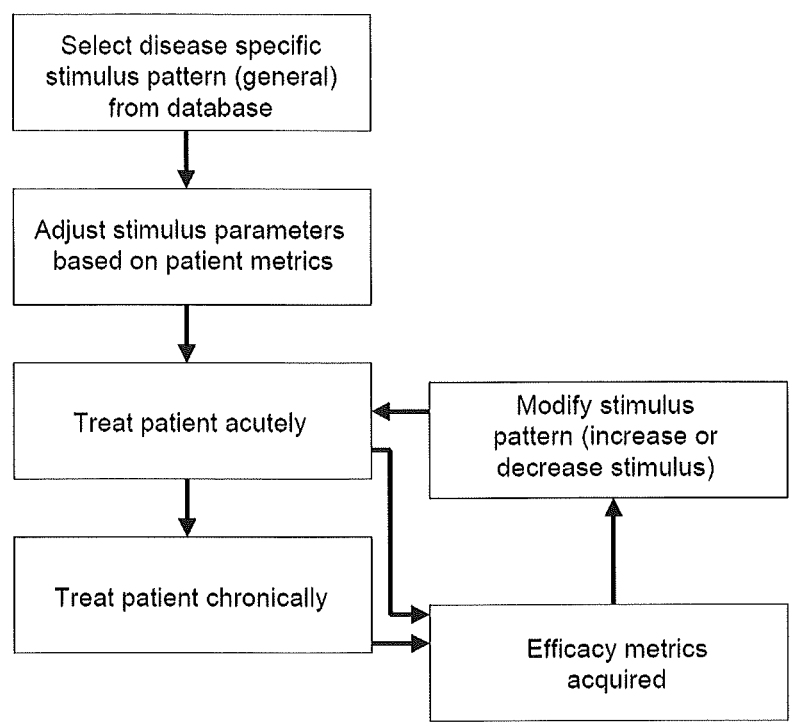
FIG. 25. A schematic diagram of physician monitoring and titration of caloric vestibular stimulation.

In order to properly track a patient's progress with CVS therapy, both acute and chronic efficacy data will be collected by the treating physician. The assessment of efficacy will dictate the course of therapy. Referring to FIG. 25, and as previously noted, the physician selects an appropriate therapeutic thermal waveform from a database of disease-specific waveforms. That general waveform may be modified by patient-specific metrics such as gender, age, medical conditions, height and weight, but also may include results of a direct measurement of the thermal conduction parameters from that patient's ear canal to the inner ear (facilitated, e.g., by an IR sensor that assesses the temperature of the inner ear over time as a function of the applied thermal waveform to the ear canal).

As acute treatment of the patient commences, the patient's subjective feedback (e.g., verbal reports, automated survey responses to questions regarding efficacy and/or side-effects, etc.) and the results of objective efficacy measurements will be collected by the physician. Objective efficacy metrics include, but are not limited to, nystagmography data, electroencephalography (EEG) data, magnetic resonance imaging (MRI) data, pulse data, blood pressure data, galvanic skin response (GSR) data, blood chemistry data (e.g., complete blood count, blood sugar levels such as determined by blood A1c levels or the blood A1c test, blood glucose levels, blood cortisol levels, etc.), saliva chemistry data, and urine chemistry data (e.g., urine cortisol levels), etc.). Based on the progress of the patient, optionally with reference to other patients with the same disease state, the physician may decide to alter the CVS prescription. In some embodiments, progression to chronic treatment preferably does not occur until the desired efficacy has been achieved by the physician by iterative administration of various acute treatments.

Nystagmography data can be collected by any suitable technique, including but not limited to videonystagmography and electronystagmography. Various devices for carrying out nystagmography are known, including but not limited to those described in U.S. Pat. Nos. 7,892,180; 6,800,062; 5,517,021; 5,360,971; 4,474,186; 4,320,768; and 4,155,352.

Once chronic or maintenance treatment commences, the physician can optionally continue to collect patient feedback (including both subjective feedback and objective efficacy metrics) on chronic efficacy and may, at his discretion, collect objective efficacy metrics to ensure that his therapeutic goals for the patient are maintained.

7. FASTIGIAL NUCLEUS ACTIVATION AND MITOCHONDRIAL DYSFUNCTION DISORDERS

As noted above, in some embodiments the present invention acts through activation of the fastigial nuclei in the cerebellum and associated mitochondrial activation, as discussed further below.

Migraine; Central Sensitization.

An earlier reported acute migraine pain study using crude, cold-water-induced CVS (Kolev, Ognyan Caphalalgia 10:16709 How caloric vestibular irritation influences migraine attacks (1990)), showed short-term positive benefits. Cold water calories is impractical for chronic treatment, nor can it induce the range of cupular dynamics enabled by the present invention. Ongoing studies by the present inventors (discussed in pertinent part below), indicate that pain alleviation and disease modulation have been achieved for subjects and that the present invention has a useful effect on migraine patients who have been refractory to other treatments for many years.

Figure 26:
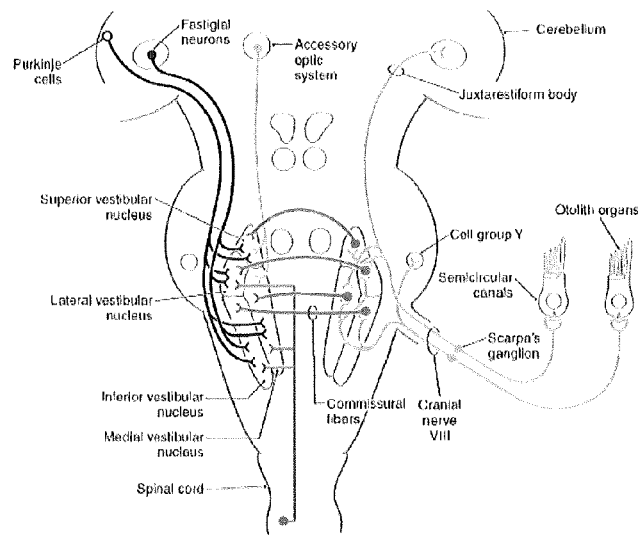
FIG. 26. A schematic illustration of the brain stem of a human subject, showing vestibular organs making afferent connections to the vestibular nuclei in the brainstem. The connection to the fastigial nuclei (FN) is also shown.

Without wishing to be necessarily limited to any one theory of the present invention, the results with migraine may be explained by the neurological effects generated by vestibular stimulation. The brainstem (see FIG. 26) is involved in the initial response to pain (Petrovic et al., Brainstem involvement in the initial response to pain. *NeuroImage* 22, 995-1005 (2004)). Abnormal brainstem activation is specific to migraines (Bahra et al., Brainstem activation specific to migraine headache. *The Lancet* 357, 1016-1017 (2001); Weiller et al., Brain stem activation in spontaneous human migraine attacks, Nature Publishing Group (1995); Moulton et al., Interictal Dysfunction of a Brainstem Descending Modulatory Center in Migraine Patients. *PLoS ONE* 3(11): e3799 (2008)); and TNM beneficially stimulates the brainstem (Minderhoud et al., On the nature of brainstem disorders in severe head injured patients: A study on caloric vestibular reactions and neurotransmitter treatment, *Acta Neurochirurgic* 34, No 1-4, 23-35)) as well as the cerebellum and numerous cortical regions. Using an appropriate dosing protocol, the present invention stimulates and initiates multiple cortical neuromechanisms, including activating thalamic pathways (Schiff et al., Does vestibular stimulation activate thalamocortical mechanisms that reintegrate impaired cortical regions; McGeoch et al., Behavioral evidence for vestibular stimulation as a treatment for central post-stroke pain. *Journal of Neurosurgery, Neurology & Psychiatry* 79 (11):1298), releasing cortical serotonin (MA Fu-rong et al., Effects of caloric vestibular stimulation on serotoninergic system in the medial vestibular nuclei of guinea pigs. *Chin Med J* 120(2):120-124 (2007)) and causing CGRP-suppression (Seong-Ki Ahn et al., Colocalization of S-HT Receptor and Calcitonin Gene Related Peptide in rat Vestibular Nuclei), as well as activating the brainstem itself (Minderhoud et al., On the nature of brainstem disorders in severe head injured patients: A study on caloric vestibular reactions and neurotransmitter treatment. *Acta Neurochirurgica*, 34, No 1-4, 23-35) and the fastigial nucleus (Zhou et al., Mitochondria are involved in the neurogenic neuroprotection conferred by stimulation of cerebellar fastigial nucleus, *J. Neurochem*, 95 221-229 (2005)).

Migraine is representative of several diseases or disorders that involve central neuropathic pain. Central sensitization, created either at the time of insult or onset or later as a secondary effect, is a common factor.

Mood Disorders.

Mood disorders (primarily depression) are often co-morbid with migraines. In studies by the present inventor, two subjects had failed all pharmacological interventions for their migraines, had been migraine-pain-refractory for several years and, in the case of one, had a failed occipital nerve stimulator (ONS) implant. Additionally, both subjects suffered from and were being treated for depression. Past, acute experiments with crude, thermal water-induced CVS have suggested the potential to improve mood and risk-taking behavior (Dodson, Vestibular Stimulation in Mania: A case Report, *J Neurol Neurosurgery Psychiatry* 75(1); 168-169 (2004); Tamagni et al., Vestibular Stimulation Reduces Unrealistic Optimism, *Nature Proceedings*, 4519, 1 (2010); Soza Reid et al., Asymmetries of vestibular dysfunction in major depression, *Neuroscience* 144, 128-134 (2007); Pettigrew et al., A "sticky" interhemispheric switch in bipolar disorder. *Proc R. Soc Lond. B.* (1998)). However, no longer-term therapeutic regimen resulted from such experiments. Treatment of subjects by the present invention were targeted primarily at refractory migraine indications, but both subjects experienced significant improvement in their mood disorder.

Traumatic Brain Injury (TBI), Concussion, and Stroke.

Vestibular pathology and TBI resulting from blast exposure (BITBI) are often co-morbid (Scherer & Schubert, Traumatic Brain Injury and Vestibular Pathology as a Comorbidity After Blast Exposure. *Physical Therapy* 89, No 9, 980-992 (2009)); and increasingly there is greater recognition that even mild concussions can later negatively affect both physical and mental health. TBI normally involves a constellation of symptoms, often including dizziness, mood disorders, migraines, tinnitus, spatial disorientation and cognitive dysfunction. Given the potential breadth and reach of cortical, cerebellar and brainstem activation from the present invention in providing controlled CVS, it is well-suited as a therapy option, either alone or as an adjuvant treatment.

Post Tramatic Stress Disorder (PTSD), Obsessive Compulsive Disorder (OCD), Attention-Deficit Hyperactive Disorder (ADHD), Anxiety Disorders, and Eating Disorders.

Each of these indications is a complex, multimodal neurological disorder. The present invention, by accessing neural mechanisms related to all cortical regions, the cerebellum and the brainstem, is well-suited to address them, either as a standalone treatment or as adjuvant therapy. Intrusive visual imagery or thoughts and/or erroneous body image is associated with all of these neurological disorders. PTSD, for example, is prototypical with respect to intrusive imagery and memories (Liberzon et al., The functional neuroanatomy of PTSD: A critical review. *Prog Brain Res.* 167:151-69 44 (2008); Speckens et al., Intrusive memories and rumination in patients with post-traumatic stress disorder: A phenomenological comparison. *Memory,* 15:3, 249-257). No pharmaceutical currently available on the market is known to suppress disruptive imagery, but vestibular stimulation can (Mast et al., Visual mental imagery during caloric vestibular stimulation. *Neuropsychologia,* 44(1): 101-109 (2006)). CVS activates the vestibular system ("VS"), leading to a reciprocal inhibition of higher-level visual cortex function associated with intrusive imagery (Holmes et al., Can playing the computer game "tetris" reduce the build-up of flashbacks for trauma. A proposal from cognitive science. *Plos One,* 4 (1) (2009); Stuart et al., The influence of visuospatial grounding task on intrusive images of a traumatic film. *Behav. Res. Ther.,* 44(4); 611-619 (2008); Lilley et al., Visuospatial working memory interference with recollections of trauma. British Journal of Clinical Psychology, 48, 309-321 (2009)). Activation of the VS should therefore impair encoding of traumatic memories and reduce vividness of imagery reactivation. The VS is known to be involved with an individual's self-perception of body image, and vestibular stimulation can correct erroneous self-perception of such image.

Patients who suffer from these neurological disorders are at risk for co-morbidities of headaches, depression, spatial disorientation, panic disorder and other manifestations of agoraphobia (Asmundson et al., Panic disorder and vestibular disturbance: An overview of empirical findings and clinical implications. *Journal of Psychosomatic Res,* 44, 107-120 (1998); Tull, Trauma, PTSD and Panic Disorder, About.com, (Jun. 28, 2010)). As discussed, the present invention has the ability to address these dysfunctions, disturbances and disorders. Additionally, inadequate neural production of serotonin is a strong predictor of poor response to PTSD therapy (Davis et al., Post-traumatic stress disorder and serotonin: New directions for research and treatments. *Revue de psychiatrie at de neuroscience.* 22, (1997)) and is associated with some of these other disorders, and CVS treatments are reported to release significant amounts of serotonin (MA Fu-rong et al., Effects of caloric vestibular stimulation on sertoninergic system in the medial vestibular nuclei of guinea pigs. *Chin Med J,* 120(2):120-124 (2007)).

Neuroprotection and Neuroenhancement.

The potential for neural modulation through vestibular stimulation to provide neuroprotection and neuroenhancement, including enhancement of spatial memory, has been reported in the literature (Golanov et al., Neurogenic neuroprotection. *Cellular and molecular neurobiology,* 23 (2003); Smith et al., Move It or Lose It—Is Stimulation of the Vestibular System Necessary for Normal Spatial Memory? *Hippocampus* 20(1); 36-43 (2010); Lay et al., Mild sensory stimulation completely protects the adult rodent cortex from ischemic stroke. *PLOS One* 5, e11270 (2010); Bachtold et al., Spatial- and verbal-memory improvement by cold-water caloric stimulation in healthy subjects. *Exp Brain Res* 136:128-132 (2001)). The neural mechanisms involved are defined and extensive, due to the multiplicity of pathways from the VS to various cortical regions, the cerebellum and the brainstem. Vestibular stimulation appears to activate the Fastigial nuclei, reduce cardiac impairment and modulate against excitotoxin and ischemic neuronal injury (Siebold et al., Fastigial Nucleus Activity During Different Frequencies and Orientations of Vertical Vestibular Stimulations in the Monkey. *Journal Neurophysiology,* 82, 34-41 (1999); Siebold et al, Rostral Fastigial Nucleus Activity in the Alert Monkey During Three-Dimensional Head Movements, *Journal Neurophysiology,* 77, 1432-1446 (1997); Yidong Wei et al., Preventive Effect of Fastigial Nucleus on Oxidative Damage in Rats Undergoing Acute Myocardial Infarction, *Journal of Health Science* 54(3) 330-334 (2008); Glickstein et al., Intrinsic Neurons of Fastigial Nucleus Mediate Neurogenic Neuroprotection against Excitotoxic and Ischemic Neuronal Injury in Rat. *The Journal of Neuroscience,* 19(10) 4142-4154), and, by employing different stimulus intensities and durations, CVS selectively enhances left or right brainstem function, accompanied by either minimal or significant cortical activity in, selectively, one or both hemispheres.

Examples of how this invention applies principles of neurology to pain management and other indications include, but are not limited to, the following:

The neural effects that result from vestibular stimulation last for several days after the stimulation occurs. Providing brief treatment with the present invention prior to an individual's being exposed to potential TBI or other neurological stress will be neuroprotective.

Phantom limb pain (PLP) is a significant risk for all amputees (Ramachandran and Hirstein, The perception of phantom limbs. The D. O. Hebb Lecture. *Brain.* 121(9), 1603-1630), especially for patients who undergo combat-related traumatic amputations (Ketz, The Experience of Phantom Limb Pain in Patients With "Combat-Related Traumatic Amputations. *Arch Phys Med Rehabil,* 89, 1127-1132). Stimulating the VS triggers the process of reconstruction of the global body schema for amputees (Andre, et al., Temporary Phantom Limbs Evoked by Vestibular Caloric Stimulation in Amputees. *Neuropsychiatry, Neuropsychology & Behavior Neurology,* 14(3): 90-196 (2001)), and vestibular stimulation has been shown to be effective in addressing PLP (Ketz, The Experience of Phantom Limb Pain in Patients With "Combat-Related Traumatic Amputations. *Arch Phys Med Rehabil,* 89, 1127-1132) and somatoparaphrenia (denial of ownership of a body part) (Lopez et al., Body ownership and embodiment: Vestibular and multisensory mechanisms. *Neurophysiol Clin* 38(3): 149-61 (2008); Bisiach et al., Remission of Somatoparaphrenic delusions through vestibular stimulation. *Neuropsychologia.* 29 (10), 1029-1031 (1991); Lopez et al., How vestibular stimulation interacts with illusionary hand ownership. *Consciousness and cognition* 19 33-4738 (2010); Ramachandran, Can Vestibular Caloric stimulation be used to treat apotemnophillia? *Medical Hypothesis,* 69 250-25239 (2007)). Those understandings are consistent with the vestibular system's being involved with an individual's sense of wellbeing and with body image (Moseley, I can't find it! Distorted body image and tactile dysfunction in patients with chronic low back pain. *Pain,* 140(1), 239-243 (2008)). Delivering the present invention to amputees both before and after amputation is likely to reduce incidence of PLP, surgical pain and rejection of a prosthesis. There are reports of simple CVS addressing anosognosia (the denial of existence of disability) (Cappa et al., Remission of hemi-neglect and anosognosia during vestibular stimulation. *Neuropsychologia* 25 (5); 775-782 (1987); Ramachandran VS, Anosognosia in parietal lobe syndrome. *Conscious Cogn.* 4 (1); 22-51 (1995)), which frequently affects patients with post-stroke spatial neglect but also is a disorder associated with amputations.

Providing patients with the present invention prior to a surgical procedure, particularly a neurosurgical procedure, is likely to reduce surgical-related trauma via control of neuroinflammation and to enhance analgesia via modulation of peripheral and central sensitization. Preemptive analgesia is a strategy often deployed via a pharmaceutical agent, using Cox-2 Inhibitors or opiates.

Additional Examples

Figure 27:
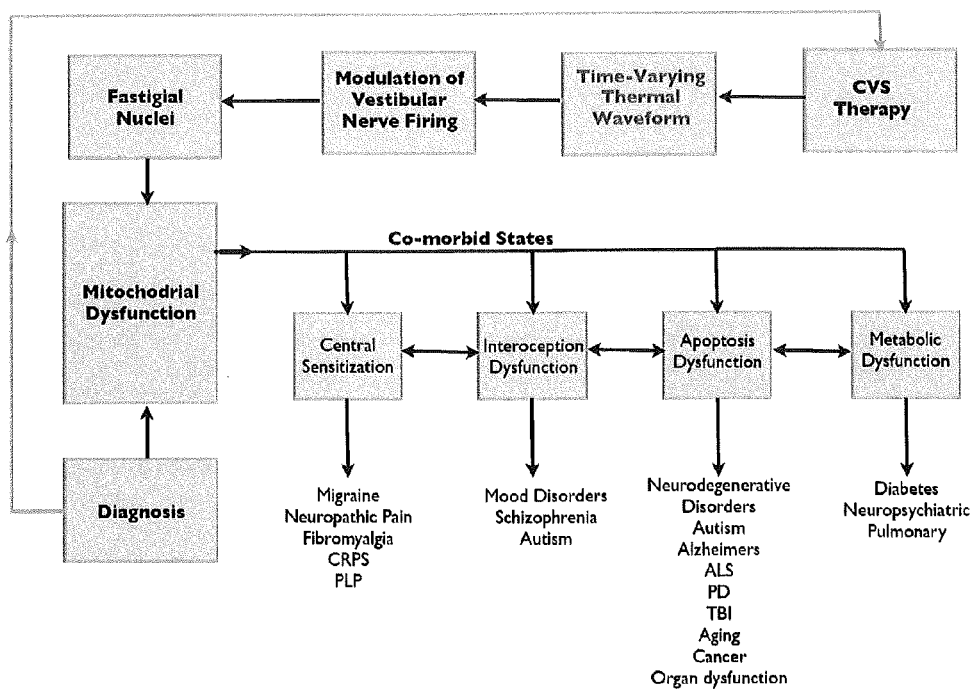
FIG. 27. A schematic diagram of illustrative diseases treated by caloric vestibular stimulation through activation of the fastigial nuclei in accordance with the present invention.

The present invention is also useful in treating neurodegenerative diseases (e.g., dementias, Alzheimer's Disease, Parkinson's Disease, amyotrophic lateral sclerosis (ALS) and Huntington's Disease), epilepsy and seizures and type II diabetes. The relationship between the present invention and these example diseases is illustrated in FIG. 27. Mitochondrial dysfunction leads to a wide variety of pathologies. Via the effect of the present invention on the fastigial nuclei (FN) (see FIG. 26) in particular, it likely activates an innate neuroprotective effect mediated by the FN.

The present invention is explained in greater detail in the following non-limiting Examples.

Example 1

Long Duration Square Wave Administration

A male subject in his forties and good health, naïve to CVS treatment, was administered cold caloric vestibular stimulation to his right ear in a square waveform pattern. The pattern was of cooling to 10 degrees Centigrade (as compared to normal body temperature of about 37 degrees Centigrade) as a "step" function or "square wave" with one symmetric square wave being delivered for a time period of 20 minutes. The subject was observed by others to be slurring his words, and was asked to remain seated for a time of two hours following the treatment session as a precaution. Otherwise, no long-term deleterious effects were observed.

Example 2

Sawtooth Wave Administration

The same subject described in EXAMPLE 1 was subsequently treated by administering cold caloric vestibular stimulation to the right ear in a sawtooth waveform pattern of cooling to 20 degrees Centigrade (as compared to normal body temperature of about 37 degrees Centigrade) in a symmetric sawtooth waveform pattern, without gaps, at a frequency of one cycle or waveform every five minutes, for a total duration of approximately 10 minutes and a delivery of a first and second waveform. Unlike the situation with the square wave pattern described in Example 1, the subject continued to perceive the temperature cycling up and down.

Example 3

Maximum Waveform Amplitude

The same subject described in Examples 1-2 was administered cold caloric vestibular stimulation to the right ear as a sawtooth cooling waveform at different amplitudes in a titration study. A maximum perceived sensation of cyclic cooling was perceived at a peak amplitude of about 17 degrees Centigrade (or cooling from normal body temperature to a temperature of about 20 degrees Centigrade). Cooling beyond this did not lead to additional gains in the sensation of cyclic cooling perceived by the subject.

Example 4

Minimum Waveform Amplitude

Modeling of the human vestibular system indicates that the cupula (the structure within the semicircular canals pushed by the movement of fluid therein and which contain hair cells that convert the mechanical distortion to electrical signals in the vestibular nerve), is stimulated by caloric vestibular stimulation at chilling temperatures of 5 or 7 degrees Centigrade below body temperature.

Example 5

Maximum Waveform Frequency

Modeling of the human vestibular system indicates that a slew rate faster than 20 degrees Centigrade per minute (which would enable one 20 degree Centigrade waveform every two minutes) is not useful because the human body cannot adapt to temperature changes at a more rapid rate. While maximum frequency is dependent in part on other factors such as waveform amplitude, a maximum frequency of about one cycle every one to two minutes is indicated.

Example 6

Minimum Waveform Frequency

Modeling of the human vestibular system indicates that a continuous, time-varying waveform is most effective in stimulating the vestibular system, as stagnation and adaptation of the cupula is thereby minimized. While minimum frequency is dependent in part on other factors such as the waveform amplitude, a minimum frequency of about one cycle every ten to twenty minutes is indicated.

Example 7

Treatment Session Duration

To permit delivery of at least a first and second waveform, a duration of at least one or two minutes is preferred. As noted above and below, results have been reported by patients with treatment durations of ten and twenty minutes. Hence, as a matter of convenience, a treatment session duration of not more than 30 or 40 minutes is preferred (though longer sessions may be desired for some conditions, such as acute care situations).

Example 8

Treatment of Migraine Headache with Sawtooth Waveforms

A female patient in her early fifties with a long standing history of migraine suffered an acute migraine episode with symptoms that consisted of a pounding headache, nausea, phonophobia, and photophobia. Right ear cold caloric vestibular stimulation was performed using the sawtooth waveform, essentially as described in Example 2 above, with a temperature maximum of 17 degrees (chilling from body temperature) for 10 minutes (for a total delivery of two cycles). At the conclusion of the treatment the patient reported that her headache and associated symptoms were no longer present. At a reassessment one day later, the patient reported that the headache had not returned.

Example 9

Treatment of Diabetes with Sawtooth Waveforms

The same subject described in examples 1-3 suddenly developed an episode of extreme urination (10 liters per day), thirst for ice water, and associated fatigue. Urinary testing suggested the onset of diabetes mellitus, for which there was strong family history.

The patient's initial weight as taken at his primary care physician indicated a recent 20 pound weight loss. The first attempt to obtain a glucose reading from the patient resulted in an out of range result (this result typically occurs with glucose levels in excess of 600 mg/dl). The patient was hospitalized and received hydration and IV insulin therapy. The patient's first glucose level after this treatment was 700 mg/dl. The glucose level were brought down to approximately 350 and treatment with an oral antihyperglycemic agent was initiated.

Follow-up care after hospital discharge with the subject's primary care physican. expanded the oral antihyperglycemic agent therapy to include both metformin and JANUVIA™ sitagliptin. In addition, a strict exercise program of 30-45 minutes 5 to 6 days per week and diet control were instituted. Daily glucose levels via finger stick were taken 2 to 3 times per day.

At this point the patient's baseline hemoglobin A1c (Hb A1c) level was 9.8%, as compared to normal levels of 5 to 6%.

The patient then began daily treatment with caloric vestibular stimulation. The treatment was carried out for a time of ten minutes, once a day for about a month, after which the treatment was continued two to three times a week for three additional months (with each treatment session being about 10 minutes in duration). The caloric vestibular stimulation was delivered to the patient's right ear, as a sawtooth cooling waveform as described in Example 2. At the conclusion of these treatments, the patient's HB A1c level was 5.3%. As a result, the patient was removed from all hypoglycemic agents.

Most oral antihyperglycemic agents lower a patient's Hb A1c level by approximately 1 to 2% (see generally S. Inzucchi, Oral Antihyperglycemic Therapy for Type 2 Diabetes, *JAMA* 287, 360-372 (Jan. 16, 2002)). In contrast, this patient's initial value was 9.5, and dropped to 5.3.

Example 10

Alternate Waveform Shapes

Figure 28:
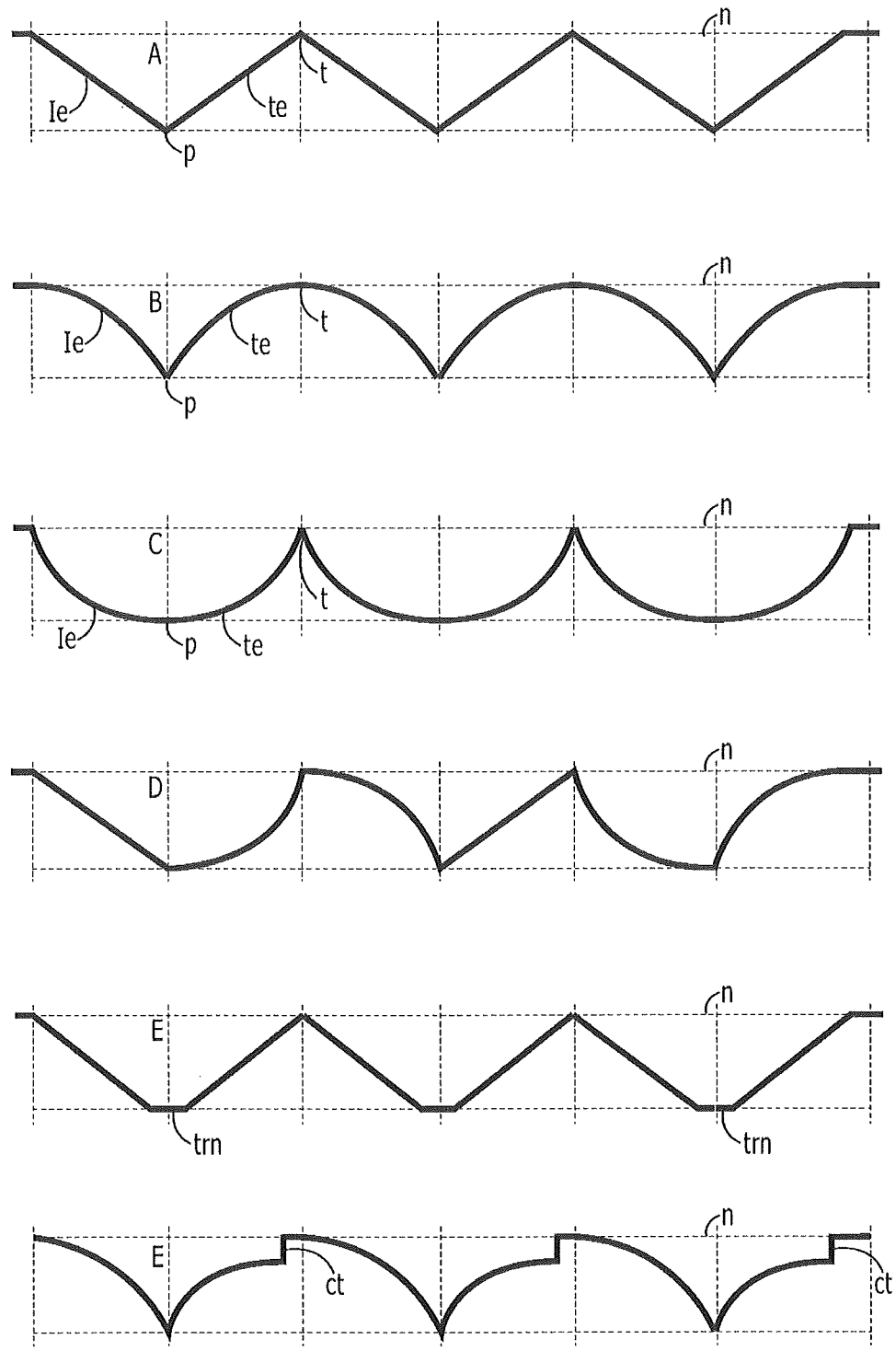
FIG. 28. A schematic diagram of various non-limiting examples of waveform stimuli that may be used to carry out the present invention. While each line A through E illustrates several cycles of a given frequency and waveform shape, note that "waveform" herein generally refers to a single cycle of a given frequency and waveform shape.

The sawtooth waveform described in the examples above was symmetric and linear, as illustrated in FIG. 28A, where line dashed line "n" represents the subject's normal body temperature (typically about 37 degrees Centigrade). Modeling of the vestibular system indicates that waveforms of similar amplitude and frequency, but with a variation in shape, are also effective, such as the "logarithmic" or "convex" waveform of FIG. 28B, and the "exponential" or "concave" waveform of FIG. 28C. All waveforms generally include a leading edge ("le"), a trailing edge ("te"), a peak ("p") and a trough ("t").

While FIGS. 28A through 28C all show three consecutive waveforms of the same shape, amplitude, and frequency, the consecutive waveforms can be varied in shape as shown in FIG. 28D, and can be varied in amplitude or duration as well (preferably each consecutive waveform within the parameters noted above), to produce still additional waveforms and sequences of waveforms which are useful in carrying out the present invention.

In addition, while the waveforms of FIGS. 28A through 28D are shown as continuous, minor disruptions can be included therein, such as truncations ("trn"; for example, as shown in FIG. 28E,) or vertical cuts ("ct"; for example, as shown in FIG. 28F) to produce still additional waveforms and sequences of waveforms which are useful in carrying out the present invention.

The peak for all waveforms of FIGS. 28A-28E is cooling by 17 degrees Centigrade from normal body temperature to a temperature of 20 degrees Centigrade, and the trough for all waveforms is a return to normal body temperature, giving an amplitude of 17 degrees Centigrade. The frequency for all illustrated waveforms is 1 cycle (or one complete waveform) every five minutes. While 3 cycles of the same waveform are illustrated for clarity, note that in some of the examples above only two cycles are delivered over a total treatment or session duration of ten minutes.

Example 11

Patient Orientation

It was noted that a patient who was sitting up (watching television) and receiving a cold caloric vestibular stimulation (CVS) treatment reported perceiving a different effect than perceived in prior sessions. Upon reclining to about 45 degrees, she did receive the earlier effect.

The "standard" angle of recline for diagnostic CVS is about 60 degrees (or equivalently 30 degrees above horizontal). The reason for this positioning is that the "horizontal" SCC is tilted up by about 30 degrees (higher on rostral side) (More recent x-ray measurements put the angle at closer to 20+/−7 degrees.) The intent with diagnostic CVS is to reorient the horizontal SCC so that it is substantially vertical, thus maximizing the effect of the convective flow set up by calorics.

Hence, if the subject is reclined to about 20 degrees above horizontal (and supine), then a cold stimulus leads to inhibition or a phasic rate less than the tonic rate. For a warm stimulus, this situation is reversed (phasic rate increases above tonic).

Further, cold simulation tends to activate principally the contralateral brain structures whereas hot leads to principally ipsilateral activation. For example, in V. Marcelli et al. (*Eur. J. Radiol.* 70(2): 312-6 (2009)), the authors did a left ear, cold stimulation by water irrigation and saw right-side activation in the brainstem, cerebellum, etc. The patient was presumably nearly reclined in the MRI magnet.

Empirical tests and modeling indicate that approximately 20 degrees Centigrade absolute cooling (17 degrees Centigrade below body temperature) is the lower limit beyond which the cupula is maximally deformed and therefore the phasic rate change is maximal. On the warming side, more than about 7 degrees or so above body temperature becomes uncomfortable. This level of temperature heating within the ear canal will not lead to maximal deformation of the cupula. Therefore, there is an asymmetry in terms of ability to span the full frequency spectrum of phasic firing rates. However, the increase in the phasic firing rate is not constrained in the manner of a decrease—that is, the phasic firing rate can only approach zero, relative to the tonic rate of roughly 100 Hz, whereas the phasic rate can exceed 200 Hz.

Since inverting the patient changes the sign of the inhibitory/excitatory motion of the cupula, the following can be seen: Using a cold stimulus, of 20 degrees absolute, but now orient the patient so that his head is tilted forward by from 75 to 20 degrees from the vertical position. This will invert the horizontal SCC relative to the image above and now the cold stimulus will result in an excitatory increase in the phasic firing rate. For clarity, tilting the head forward by 20 degrees makes the horizontal SCC substantially horizontal. Tilting beyond that now starts to invert it so that at 110 degrees (tilted forward), the horizontal SCC will be in a vertical orientation, but now 180 degrees flipped from what is used in conventional diagnostic caloric vestibular stimulation. So, the "general rule" for treatment of having the patient reclined by 45-90 degrees can be expanded to include "tilted forward" by 75-120 degrees.

Thus a protocol is seen where, using only cold stimulus, one can cover the entire range of phasic firing rates simply by reorienting the patient at the appropriate points during the time course of treatment.

Note that this type of inversion should also lead to an inversion in the side of the brain that is primarily activated. Specifically, if cold stimulation leads to principally contralateral activation in the "rightside up" orientation, then it should lead to principally ipsilateral activation in the "upside down" orientation.

Example 12

Thermal Modeling of Caloric Vestibular Stimulation

Equation (4) of Proctor et al. (Acta Otolaryngol 79, 425-435, 1975) can be extended for an arbitrary sequence of heating and/or cooling steps. Equation (4) is a fairly simple usage of the 1-dimensional diffusion equation. Therefore, the model is not exact. The temperature difference across the horizontal canal (i.e., the thermal driving gradient) is approximated:

$$\Delta T = \frac{A_1}{\sqrt{t}} e^{\frac{-B}{t}} + \frac{A_2}{\sqrt{t-t_1}} e^{\frac{-B}{(t-t_1)}} + \ldots + \frac{A_n}{\sqrt{t-t_n}} e^{\frac{-B}{(t-t_n)}} \quad (1)$$

$$\text{where: } A_n = \frac{-LT_n}{\sqrt{\pi a}} \text{ and } B = \frac{x^2}{4a}$$

L=distance across horizontal canal (mm); default=6

$T_n$=difference between applied temperature and previous temperature (° C.)

a="thermal diffusivity" of temporal bone (mm2/sec); this may vary in patients, but compact bone paths will dominate the thermal. The literature lists values from 0.14-0.25, but this is based on the onset of nystagmus as the "stimulation time." Marcelli et al. showed a much faster, actual brainstem activation time after CVS, which did not relate to the onset of nystagmus. Literature estimates for the thermal diffusivity of hard bone range from 0.45-0.55 to 1.6. A value of 0.5 is assumed here, based on x-rays of the compact, wet bone in the region of interest.

x=the effective thermal distance (mm) between external ear canal and the edge of horizontal semicircular canal; default=7.5 mm ΔT=the temperature difference across the semicircular canal (° C.); distal minus proximal temperature.

$t_n$=time at which new stimulus starts.

Default values for the constants are listed next to the definitions. CVS application times that are short compared to the response time of the patient may not be very different from a longer pulse at a lower temperature due to thermal smoothing effects. Literature reports of the maximum phasic firing rate are about 100 Hz. That is, +/−100 Hz away from the tonic firing rate, which is on the order of 100 Hz. The maximum deformation of the cupula at its center is, correspondingly, about 77 microns. Thermal gradients that imply a deformation greater than this value would tend to lead to saturation of the phasic firing rate. At the other end of the scale, the minimum detectable volume change in the SCC is on the order of 25 picoliters and this corresponds to a change in the phasic rate of roughly 0.5 Hz. This indicates a minimum temperature gradient across the SCC of ~0.02° C. The obvious requirement is that the body's homeostatic temperature regulation must ensure a constant temperature across the 6 mm wide canal to a value on that order.

Another simplification used in the model was to ignore the temperature dependence of the bulk coefficient of thermal expansion of water (with the simplifying assumption that endolymph has roughly the thermal properties of water). This assumption will lead to an apparent saturation of the phasic firing rate at higher temperature (roughly 27° C.) than will actually occur. Below body temperature, the phasic rate may not saturate until the lower 20's.

The volume of the horizontal SCC is estimated to be: 3.2E-3 cc. The change in volume due to a temperature difference ΔT is: 3.8E-4*3.2E-3*ΔT=1.22E-6 ΔT.

The volume of the "lens" of the cupula when deformed to its maximal (saturation of the phasic firing rate) extent is roughly: 4.4E-6 cc Therefore, the change in the phasic rate: Δf=27.7*ΔT in Hz.

The relationship between the applied thermal waveform and the phasic firing rate of the afferents of the vestibular branch of the 8th cranial nerve can thus be modeled for a square waveform stimulus (such as in Example 1 above) as shown in FIG. 29 herein, and for a time-varying, saw tooth, waveform stimulus (such as in Example 2 above) as shown in FIG. 30 herein.

Note that there is little distortion of the time-varying waveform of FIG. 30, as compared to the square waveform of FIG. 29, because the body can track the more gradual temperature changes.

There is a tendency for the values to skew a small amount vertically (e.g., the temperature delta goes slightly above body temp at points). This effect appears to be non-physical and is simply a limit of the approximate model employed. The same appears true of the firing rate going positive.

The "tips" of the sawtooth waveforms appear to exceed the maximum change in phasic firing rate of 100 Hz (this is seen in the square wave as well). This may be because the coefficient of thermal expansion of the endolymph changes with temperature and was not corrected in the model above. This would result in an overestimate of the firing rate for a given temperature in the plot. Therefore, the firing rate may not, in fact, saturate (i.e., will stay below a delta of 100 HZ) at 20 C. The loss of a sense of improvement reported in Example 3 above for temperatures below about 17 to 20 degrees Centigrade may be due to the cupula of the vestibular canal "pegging" (achieving its maximal physical distortion) and the firing rate saturating.

Example 13

Treatment of Chronic Migraines and Refractory Depression

A female subject was a headache sufferer with a 10-year history of debilitating, chronic migraines, the last five being refractory. She had failed all pharmaceutical interventions. The patient underwent an occipital nerve stimulator implant for headaches, with good symptom-management for approximately one year, at which point the device was no longer effective. Co-morbid with her migraine headaches was depression, which was only partially responsive to pharmaceutical management. Subject was placed on disability from her employment.

The subject was treated using a five-day therapy paradigm consisting of daily treatments comprising a square waveform pattern of cooling to 20 degrees Centigrade, at a frequency of one cycle every ten minutes, for a total duration of ten minutes while the patient was in a reclined position of thirty degrees above horizontal. Video images of the subject were captured before, during and after each treatment session and were used to assess the effectiveness of the treatment (e.g., by assessing the patient's mood).

For all active, in-process migraine episodes, within 5-15 minutes after completion of a treatment, subject experienced pain attenuation. Chronic headache indication was alleviated on the 4$^{th}$ day of treatment, with concurrent progressive improvement in her mood over the course of the five days. The treatment course peaked at day 5. The subject became pain-free, with complete resolution of mood symptoms. She remained pain-free for 63 days after the therapy was completed, at which time her migraine headaches began to recur, but without return of clinical mood symptoms.

The five-day therapy paradigm was repeated. The subject responded more quickly to this second longitudinal therapy, with her chronic headaches disappearing on the 3$^{rd}$ day of treatment. She remained pain-free for five weeks.

Figure 31:
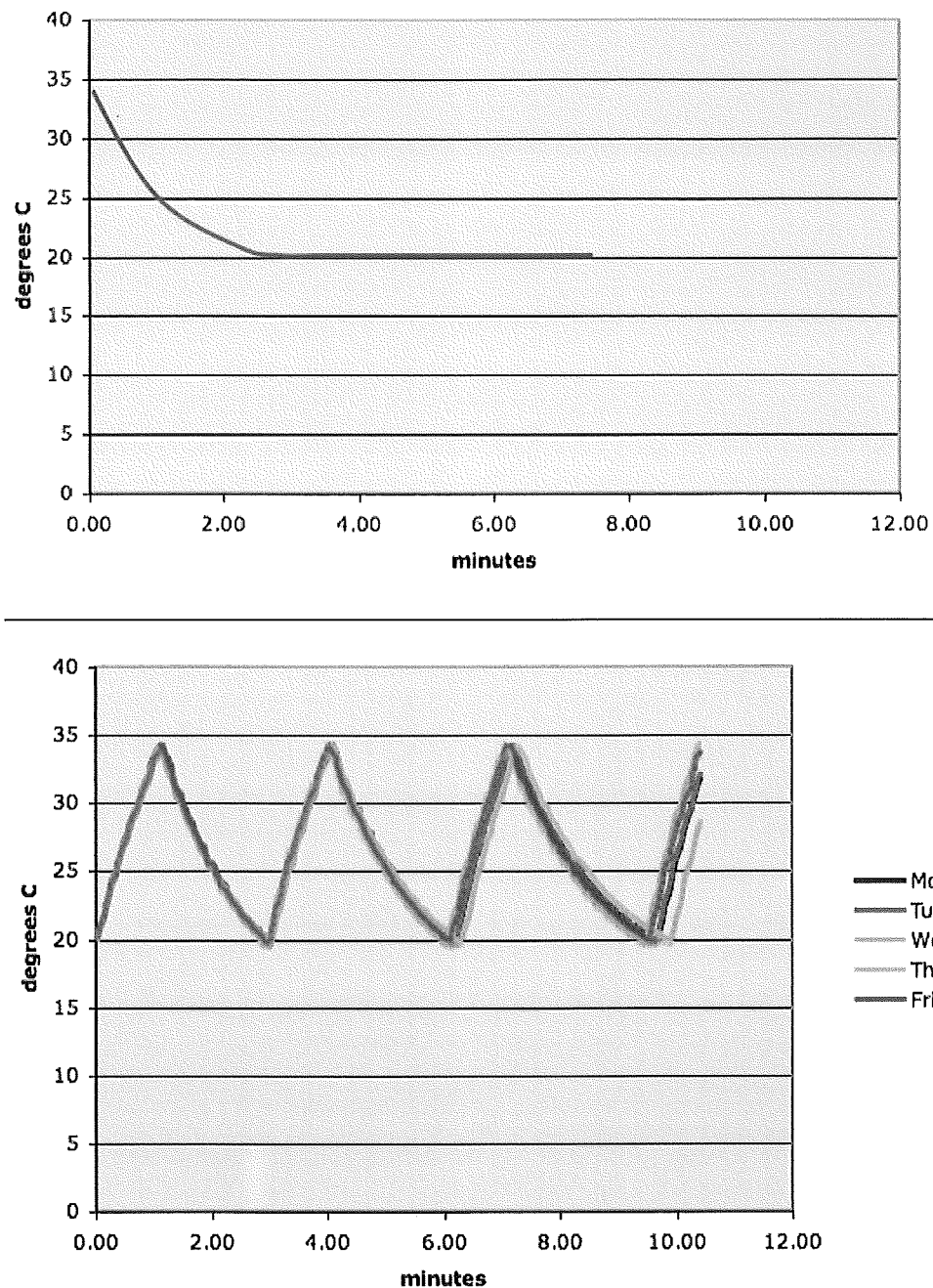
FIG. 31. Sawtooth waveforms for treatment of a chronic migraine patient.
Figure 32:
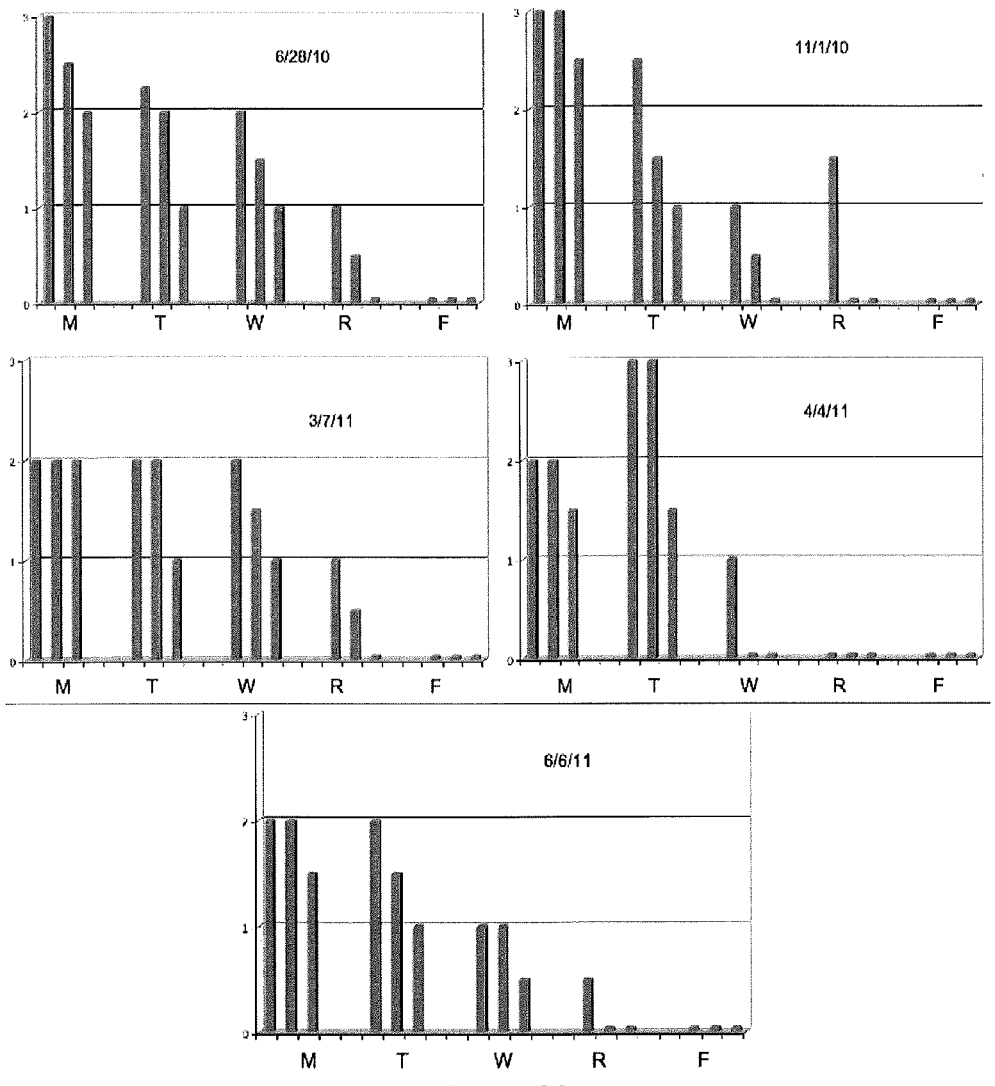
FIG. 32. Pain scores reported by the patient treated with the sawtooth waveforms of FIG. 31.

Later, the patient was treated with a sawtooth waveform (FIG. 31) (lower temperature of 20° C.) employing a daily treatment duration of 10 minutes. By the end of the treatment week, the patient was pain free (using a 0-3 pain scale where 3 is severe, 2 is moderate, 1 is mild, and zero is no pain). The chart (FIG. 32) shows pain scores, each day, pre-treatment, immediately after treatment, and 2 hours after treatment. All CVS treatments were to the right ear using cold stimulation. Additionally, after each treatment week, the patient stayed pain free for times varying from 2-9 weeks. The patient additionally reported feelings of high energy and resolution of co-morbid depression.

Example 14

Treatment-Associated Dizziness in Migraine Patient

Figure 33:
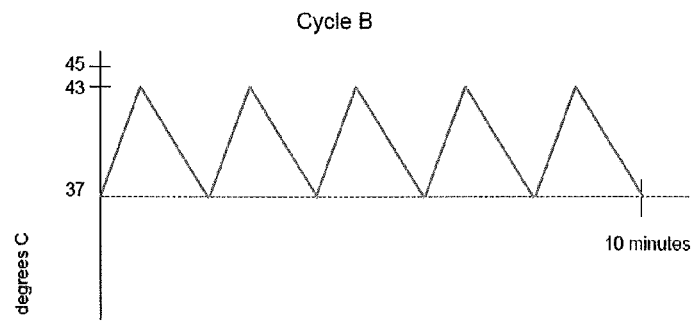
FIG. 33. Sawtooth waveforms for treatment of a migraine patient.

The same subject described in example 8 had right ear CVS treatment using a heating, to approximately 42-43 degrees, sawtooth waveform for 10 minutes as illustrated in FIG. 33, with a contiguous repeat for an additional 10 minutes. The treatment was effective in resolving her acute migraine pain. Additionally, the treatment had a soporific effect but also caused slight dizziness. The subject did not note the feeling of dizziness in example 8 using cold stimulation.

Example 15

Treatment of Cluster Headache and Treatment-Associated Dizziness

The same subject described in example 1 underwent the same CVS treatment described in example 14. He too reported a feeling of slight dizziness that was not apparent during cold CVS stimulation.

Example 16

Vestibular Migraine Treatment in Female Patient

A female subject in her late 30's had a history of migraine with associated vertigo (vestibular migraine). The subject has a history of vestibular dysfunction and slight co-morbid depression. The subject was treated on a near daily basis, between 20-40 minutes per day, with cold stimulation (down to 20° C.) CVS before switching to warm CVS, with a maximum temperature of 48° C. All CVS treatments used a sawtooth pattern with left-ear stimulation due to more severe vestibular dysfunction in the right ear. This subject did not note dizziness as a side effect of the warm CVS treatment, suggesting that her vestibular system, due to dysfunction, is more immune to CVS (and thus she must treat more aggressively to gain benefit). A parent of the subject commented on a change in the subject's speech and "spirit" during phone conversations while using cold CVS. The switch to warm CVS resulted in additional mood and motivational elements. Colleagues commented on enhanced interpersonal interactions and an increased sense of confidence. The subject stated: "for the last couple of year I've felt as if my brain has burnt out, it feels so much better since the warm treatments."

Example 17

Vestibular Migraine Treatment in Male Patient

A male in his 40's developed sudden onset migraine with vestibular dysfunction that led to effective disability and inability to go to work. The subject was not helped by medications and sought the advice of multiple physicians at two prominent academic research hospitals. The subject was treated on a near daily basis for 10-20 minutes a day with cold CVS (down to 20° C.) CVS before switching to warm CVS, with a maximum temperature of 42° C. The subject, like the subject in example 16, did not experience dizziness with the introduction of warm CVS treatments, possibly associated with the vestibular dysfunction accompanying his migraines. CVS treatments are soporific for this patient. The subject's wife notes a pronounced change since CVS treatments were started. Whereas prior to CVS treatment the subject was loath to get out of bed, since CVS treatment the subject has returned to part-time work with his employer.

Example 18

Treatment of Diabetic Patient with Warm Sawtooth Stimulation

Figure 34:
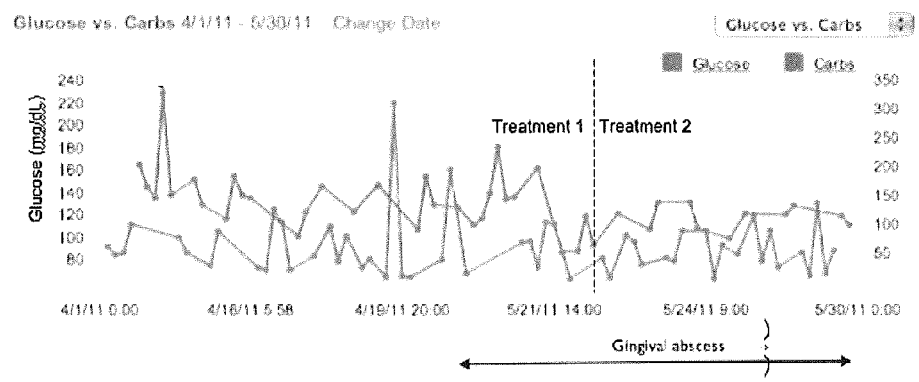
FIG. 34. Serum glucose readings for a diabetic patient treated with a sawtooth waveform.

The same subject described in example 9 switched from cold CVS to warm CVS for the control of his type II diabetes. He treated with a sawtooth waveform that oscillated between 34 and 43° C. The average heating slew rate was typically above 40° C./min and the average cooling slew rate was typically greater than 10° C./min. Since commencing CVS therapy, the subject has stopped taking medications, which were previously necessary to maintain serum glucose near a normal range. At the time of diagnosis, the subject's A1c value was 9.8. At the time shown at the end of the chart below, that value was reduced to 5.6 (again, with no medications). A1c is viewed as a better long-term marker of diabetes control than serum glucose (it doesn't fluctuate). The normal range is about 4-6. For diabetics, the recommendation is that anything below 7 is a good target. The chart in FIG. 34 shows a record of the subject's serum glucose readings and the possible additional improvement realized with the switch from cold to warm CVS in terms of reduced variability. The subject also had a gingival abscess during the period shown and such infections can lead to oxidative stress and impaired glucose control (see generally J. Southerland et al., Diabetes and Periodontal Infection: Making the Connection, *Clinical Diabetes* 23, 171-178 (2005)). The infection did not disrupt the subject's glucose maintenance.

Glucose readings taken at 7 AM and 10 PM; CVS treatment in evening. Treatment 1: 34 to 17 degree C. sawtooth waveform, 20 minute duration. Treatment 2: 34 to 43 degree C. sawtooth waveform, two 20 minute treatment per day. Glucose levels are more controlled with treatment 2. No other diabetes medications were in use during the testing period. The subject reported that the warm sawtooth CVS differed slightly from the cold sawtooth CVS in that it appeared to have increased potency as noted by the feeling of increased dizziness and mild nausea, which appear consistently with each treatment. Glucose levels tend to drop 10-30 points approximately 60 minutes or more after the treatment. The subject reported that combining exercise in proximity to the TNM therapy appeared to cause a glucose decrease of 30 to 50 points.

Example 19

Treatment of PTSD Patient

A male in his mid 60's was wounded three times as a Medic in Vietnam and had a history of post-traumatic stress disorder. His manner is described as introverted and his mood depressive. After the commencement of cold CVS treatments, the subject's wife reported that he started becoming more extroverted. She reported that "she did not know who this person was speaking to her this morning"; that he was planning getting together with friends; that usually he would only do this if forced; that he expressed interest in going to Africa for a photo safari; that she started thinking "where is my husband?" After a second treatment, the subject reported continuous sleep throughout the night (usually he would usually wake up 3-4 times). He commented that "insomniacs should use this." The subject reported feeling energized. The subject was usually unable to recall dreams, but awoke with visual flashback of events in Vietnam, not unpleasant just old visual memories, and returned to sleep. The subject traditionally avoided driving but now is driving with substantially less hesitation. The subject is a serious amateur painter and both the subject and his spouse report significant positive developments in his painting style and productivity since commencement of his CVS. Upon interruption of CVS therapy, PTSD symptoms gradually returned almost to baseline one week after CVS stopped.

Example 20

Treatment of Diabetes in a PTSD Patient

Figure 35:
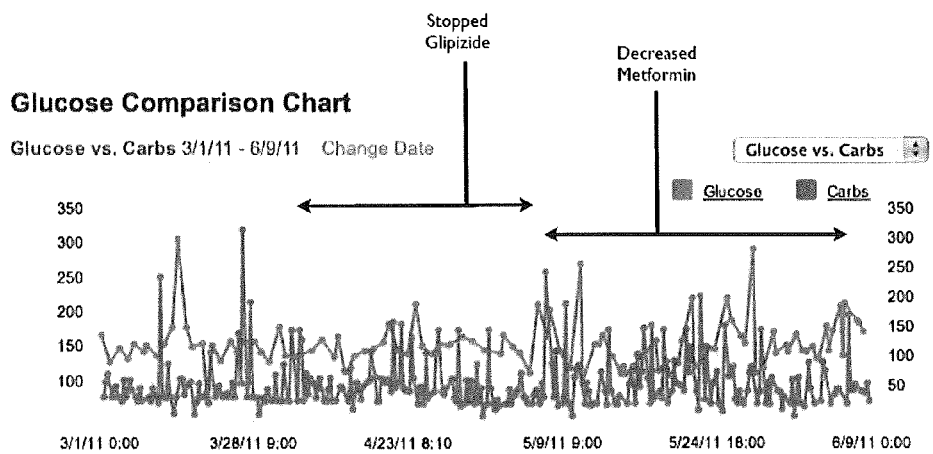
FIG. 35. Additional serum glucose readings for a diabetic patient treated with a sawtooth waveform.

The patient of example 19 has type II diabetes. After the commencement of CVS therapy he became much more responsive to oral hypoglycemics, has had to cut dose significantly as indicated in the chart in FIG. 35.

Example 21

Alternative Waveforms in Treatment of Diabetes and Cluster Headaches

Figure 36:
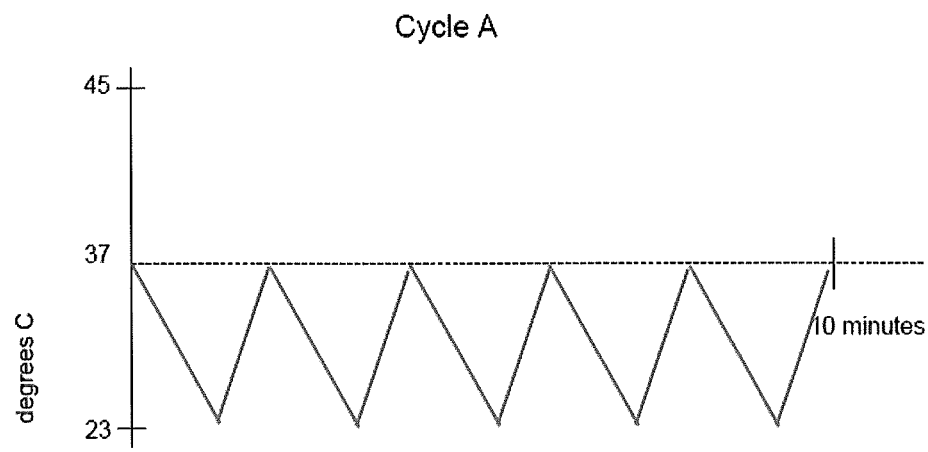
FIG. 36. Cooling sawtooth waveform for treatment of patient with diabetes and cluster headaches.

The patient described in example 18 above was administered three different waveform CVS stimuli, as follows:

A: Cooling, by approximately 22-23 degrees, with a spike waveform for 10 minutes as illustrated in FIG. 36, with a contiguous repeat for an additional 10 minutes.

Figure 37:
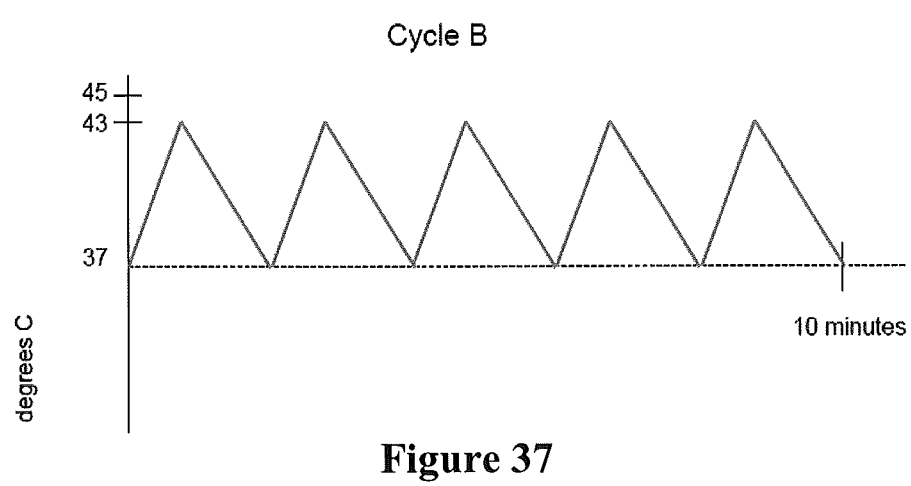
FIG. 37. Heating sawtooth waveform for treatment of patient with diabetes and cluster headaches.

B: Heating, to approximately 42-43 degrees, with a spike waveform for 10 minutes as illustrated in FIG. 37, with a contiguous repeat for an additional 10 minutes.

C: Cooling, to approximately 22-23 degrees, with a spike waveform for 10 minutes as illustrated in connection with A above, followed immediately by heating, to approximately 42-43 degrees, with a spike waveform for 10 minutes as illustrated in connection with "B" above.

The treatments seemed to have a bimodal pattern of efficacy based upon cooling or heat cycles. Both modes seem to induce a sense of motion and mild nausea associated with enhanced therapeutic efficacy for the treatment of cluster headaches and the stabilization of type II diabetes in this subject. Pattern A appeared to be the most efficacious. Increasing cycle times to thirty minutes does not appear to confer an additional benefit.

Example 22

Induction of Prolonged Nystagmus by Waveform CVS

Nystagmus is the name given to involuntary eye movements enabled by the so-called vestibulo-ocular reflex (VOR). CVS provides an artificial means to activate the VOR. By tilting the head (~20 degrees above the horizontal), the horizontal SCC is placed in a vertical orientation. Creating a differential temperature across this canal results in convection currents that act to displace the cupula. Warm CVS leads to cupular displacement such that the phasic firing rate increases whereas cold CVS leads to a decrease in the firing rate. Further, warm CVS results in nystagmus that is manifested by a rapid movement of the eyes towards the simulated ear. Cold CVS results in the rapid phase of nystamus away from the stimulated ear. Therefore, by noting the existence and the direction of nystagmus, one may determine that the VOR is being activated and whether the phasic firing rate is greater than or less than the tonic firing rate.

The use of continuous CVS irrigation or stimulation at a constant temperature will induce nystagmus, but after a time on the order of 2-3 minutes (e.g, Bock et al., *Vestibular adaptation to long-term stimuli*, Biol. Cybernetics 33, 77-79 (1979)), the cupula will adapt to its new, displaced position and the phasic firing rate will return to the tonic rate. Thus nystagmus will effectively cease and the vestibular nerve afferents will no longer be stimulated.

Figure 38:
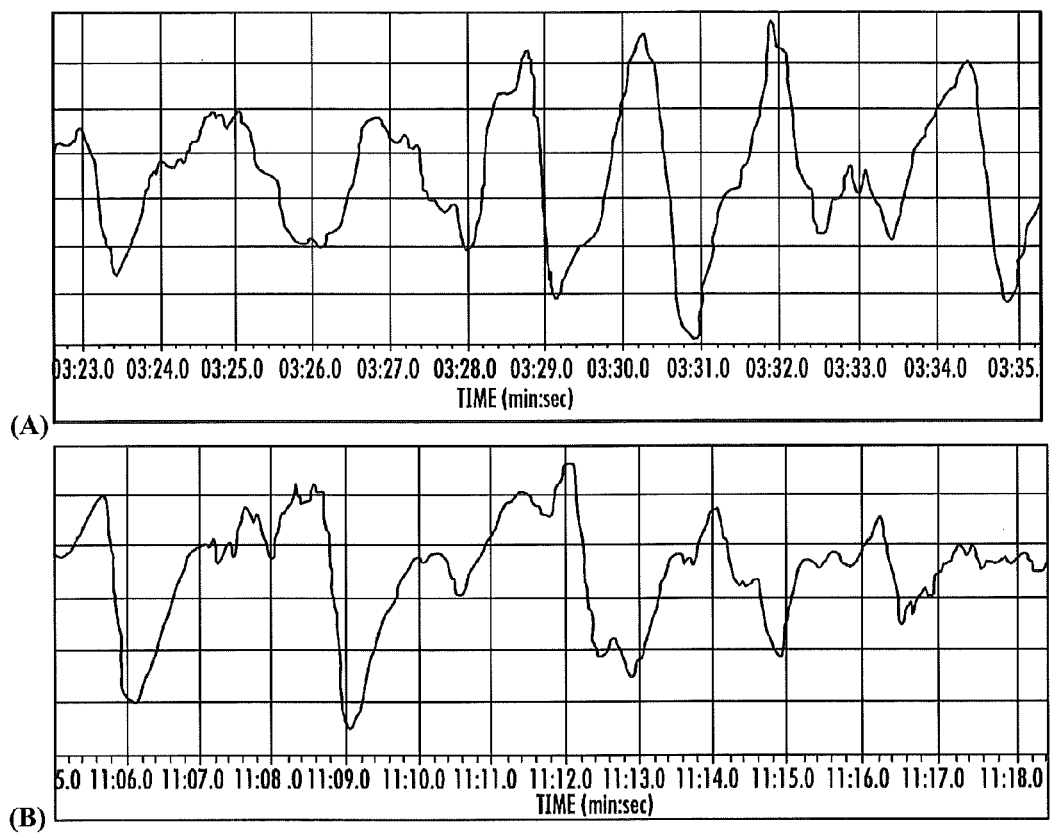
FIG. 38. Segments of the time series of nystagmus are shown by electronystagmography in FIG. 38A (early segment) and FIG. 38B (late segment), demonstrating the existence of nystagmus both early in a 12 minute period and near the end of the 12 minute period.

It is an aspect of the current invention that the use of time-varying thermal waveforms enables the persistent stimulation of the vestibular nerve afferents, beyond the time period at which adaptation to a constant thermal stimulus occurs. In this example, the present invention has been used to generate nystagmus over a 12 minute period as measured by videonystagmography and by electronystagmography. A sawtooth cooling waveform going between temperatures of 34 to 20° C. was applied to the right ear of a subject who was reclined such that his head was ~20 degrees above the horizontal. Electronystagmography was used to measure the movement of his eyes. Segments of the time series of the nystagmus are shown in FIG. 38A (early segment) and FIG. 38B (late segment), demonstrating the existence of nystagmus both early in a 12 minute period and near the end of the 12 minute period.

Example 23

Effect of CVS on Regional Cerebral Blood Flow (rCBF)

The purpose of this Example is to find a robust marker of successful CVS induction of relevance to neurological treatments. The study is being performed on rats using a modified version of a dual ear CVS unit. Specifically, ear bars that are connected to TEC's are placed in the ear canals of rats that have been anesthetized. The device has dual ear stimulation capability.

Methods and Results:

Single ear CVS: Rat #9 received a sawtooth waveform in the right ear that oscillated between 36 and 14° C. for 60 minutes (FIG. 39). The rat was anesthetized with isoflurane. It should be noted that anesthesia may lessen the effects of CVS to a degree. The rat was oriented horizontally, which places the horizontal semicircular canal in the vestibular bodies at a roughly 30 degree tilt upwards on the anterior side. After the end of the 60 minute right ear stimulation, the same caloric waveform was then applied to the left ear. The plot in FIGS. 40-41 shows the response of the regional cerebral blood flow as measured on the right parietal region of the skull via a laser Doppler probe affixed to the skull. Roughly 30 minutes after the start of right ear CVS, the oscillation in blood flow became pronounced. The period of the sawtooth temperature waveform is 1.9 minutes. As seen in the graph in FIG. 42 (using nearest neighbor averaging), the period of the modulation in blood flow is longer, by about 30 seconds on average. This suggests that the driving force (the CVS) leads to modulation of the blood flow via a mechanism that stays in a non-equilibrium state. That is, the rat's response does not simply match the period of the CVS waveform and is instead adapting to it dynamically. At the end of right ear CVS, the oscillations stop. Roughly 35-40 minutes after the start of left ear CVS, clear oscillations once again appear, though diminished in amplitude relative to right ear stimulation. This is presumably due to the fact that left ear stimulation has a weaker effect on blood flow in the right portion of the brain. Serrador et al. (*BMC Neuroscience* 10, 119 (2009)) note that "connections have been found between the vestibular nuclei and the fastigial nucleus . . . followed by vasodilatory connections to the cerebral vessels."

Figure 43:
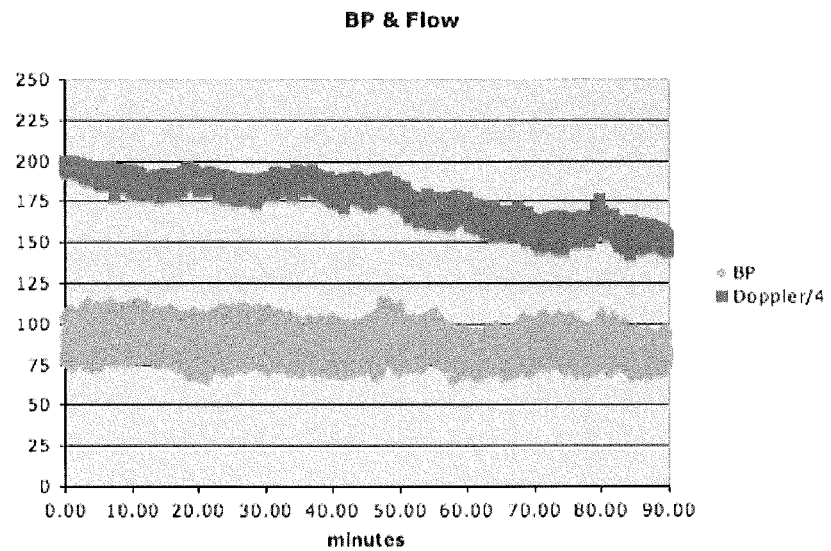
FIG. 43. Regional cerebral blood pressure and blood flow for a control run in which a caloric vestibular stimulation device was placed on a rat but not activated.

Control Run:

The data in FIG. 43 show the results from a control run wherein the CVS device was placed on the rat, but was not activated. No oscillations in rCBF were seen (the downward drift in the flow data is due to a slight shift in the baseline of the probe).

Figure 44:
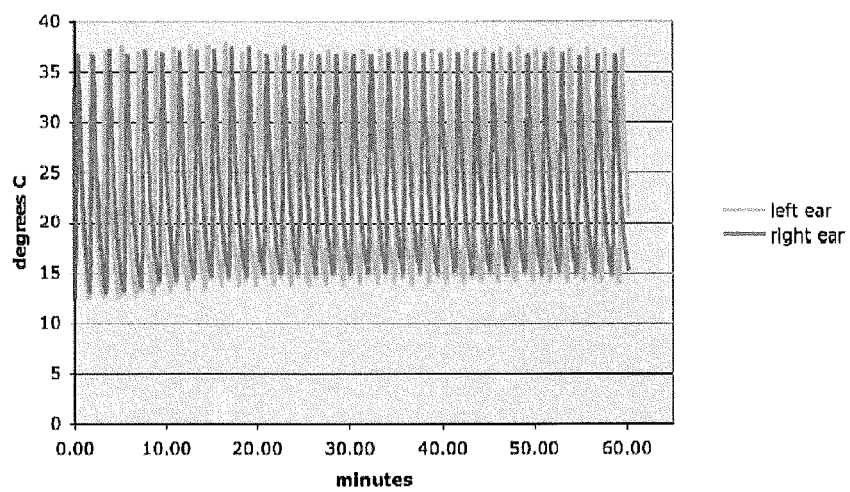
FIG. 44. Dual ear waveform stimulation of a rat, in which the same waveform was applied simultaneously to each ear.
Figure 45:
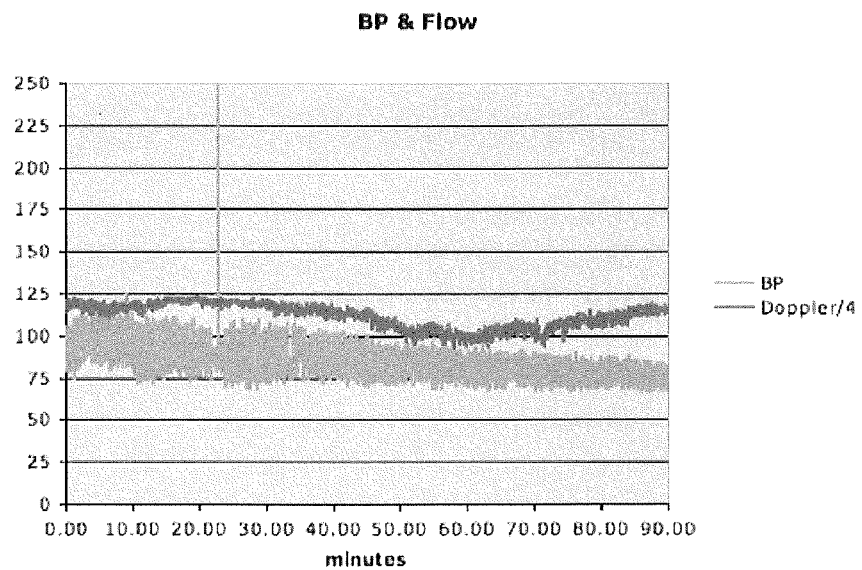
FIG. 45. Regional cerebral blood pressure and blood flow for a rat treated with the waveform of FIG. 44.

Dual Ear, Same Waveform:

Rat #12 had CVS delivered to both right and left ears simultaneously (FIG. 44). The waveforms were not tied in phase and tended to become out of phase during the bulk of the 60 minute treatment period. No modulations in rCBF were manifested (FIG. 45).

The dual ear stimulation data suggest that the application of the same waveform to both ears simultaneously acted to cancel out any net modulatory effect on rCBF. However, it is still the case that the same stimulation was given to the vestibular nuclei as when only single ear CVS was used. Nystagmus, would also not appear if the same CVS stimulation were applied to both ears since the phenomenon, mediated by the vestibulo-ocular reflex (VOR), requires a differential input to the two horizontal SCC's. Thus the absence of rCBF modulation does not mean that the fastigial nuclei (both nuclei for dual ear CVS) are not being stimulated. Rather, their combined activation yields no net effect on rCBF. Since modulation of rCBF is not a necessary aspect of CVS induced neuroprotection (it is a marker of CVS induction), CVS therapy may actually be as or more effective with dual ear stimulation.

Figure 46:
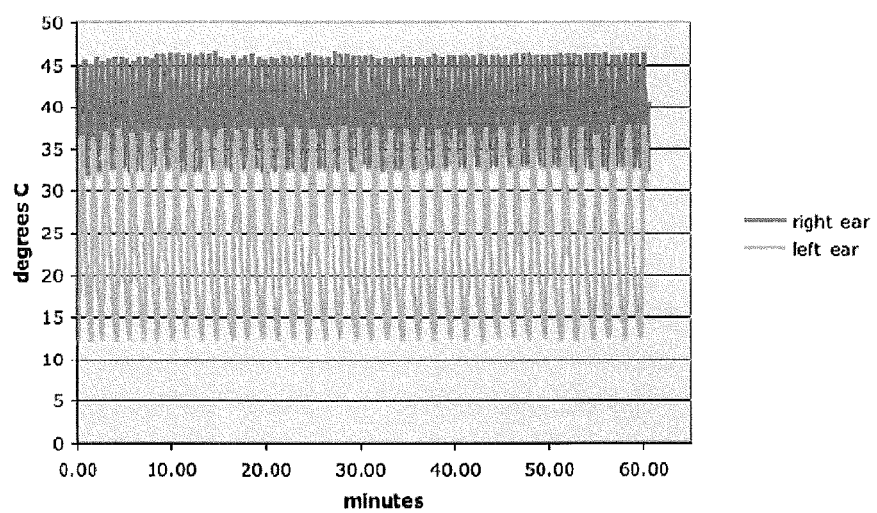
FIG. 46. Dual ear waveform stimulation of a rat, in which different waveforms were applied simultaneously to each ear.
Figure 47:
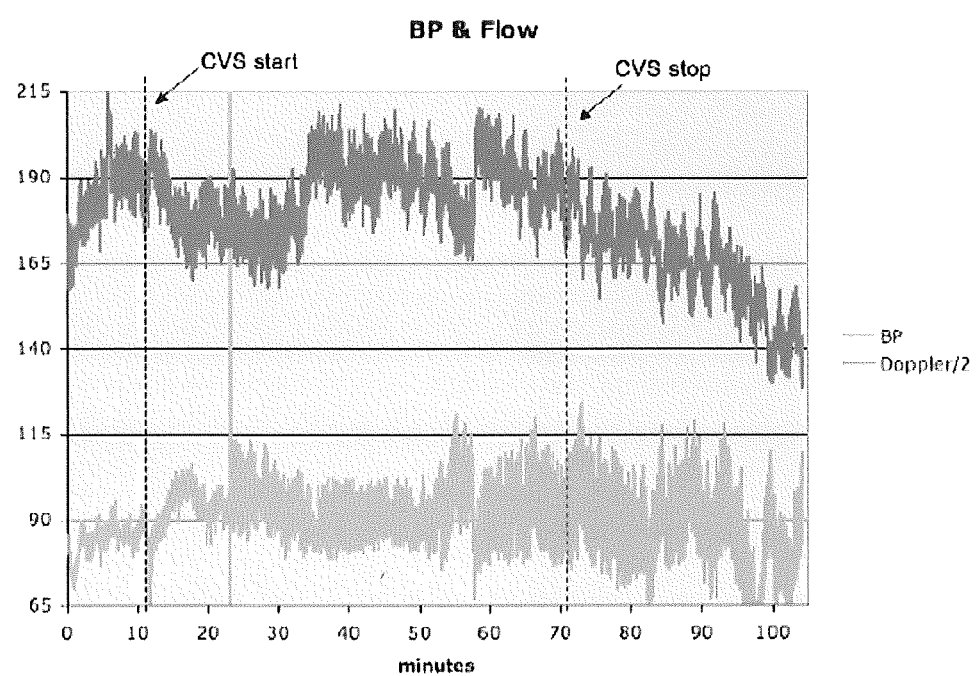
FIG. 47. Regional cerebral blood pressure and blood flow for a rat treated with the waveforms of FIG. 46.

Dual Ear, Different Waveforms:

Run 17 simultaneously applied a 34 to 44 C sawtooth waveform to the right ear (period of ~40 seconds) and a 34 to 13 C sawtooth (period ~1.7 min.) to the left ear (FIG. 46). In this case, flow modulations were seen and they persisted well past the end of the CVS treatment period (FIG. 47). In this case the flow effect, with different temperatures applied, not only was present but continued to oscillate after the end of the active CVS treatment.

Summary:

The vestibular systems of all mammals act in the same way. Therefore, the results of the rat study discussed above has implications for human CVS therapy as well. The conclusion from the study is that the most likely cause of the modulation seen in rCBF is that CVS does stimulate the fastigial nucleus in the cerebellum.

Example 24

EEG in Rats as a Metric of CVS Efficacy

EEG is useful in identifying cortical activation associated with CVS. Therefore, EEG is useful as a non-invasive means to titrate CVS therapy. This report summarizes EEG data acquired in a rat study.

Methods and Results:

The report on regional cerebral blood flow changes in a rat during various CVS treatments has been generated. In this summary, EEG electrodes were placed in the scalp of the rat, differential pairs being applied on either side of the midline of the skull. The plot in FIG. 48 shows the resultant change in activity when comparing the baseline (prior to CVS starting), "high" flow, and "low flow" conditions, where the oscillations in regional cerebral blood flow are the markers of change. The CVS stimulus was a 34 to 13° C. sawtooth applied to the right ear.

Discussion:

As can be seen in the 0-12 Hz plot above, the activity in the theta band was markedly different between the 3 states. For the low flow state, activity was depressed. The high flow peaks were shifted to lower frequencies as compared to the baseline (pre-CVS). In the 0-40 Hz plot, the high and low flow peaks in the low-30 Hz range overlap whereas the baseline peak is shifted (this is likely due to a difference in somatosensory perception during CVS versus pre-CVS). The sensitivity of EEG spectra to the details of CVS delivery suggest that EEG is an effective tool for evaluating the difference between CVS waveforms and for titrating them.

Example 25

Heart Rate Variability (HRV) as a Metric of CVS Efficacy

Heart rate variability seems to be a significant marker of health and systems for measuring it non-invasively are becoming common. This report describes the use of the ithlete, a commercial HRV measurement instrument that runs as an smartphone software program, or "app."

Methods and Results:

The subject is a 40-45 year old male diagnosed with seasonal cluster headaches. The device used to measure HRV is the ithlete (HRV Fit Ltd., Hants UK)) which uses an iPhone as the recording/readout device and a chest strap with sensors that monitor heart rate. The HRV parameter is calculated via a proprietary algorithm that takes the raw heart rate data as input. Note: of course there are many devices that will measure HRV and the ithlete was chosen only as a low cost and convenient system. Proper HRV is used as a metric of proper cardiac health (good health implies adequately high HRV; e.g. Malik, "Heart rate variability: standards of measurement, physiological interpretation, and clinical use," Eur. Heart Journal, vol. 17, pg. 354, 1996). For example, Gujjar et al. have linked HRV and outcomes after acute severe stroke ("Heart rate variability and outcome in acute severe stroke," Neurocritical Care, vol. 1, pg. 347, 2004).

Figure 49:
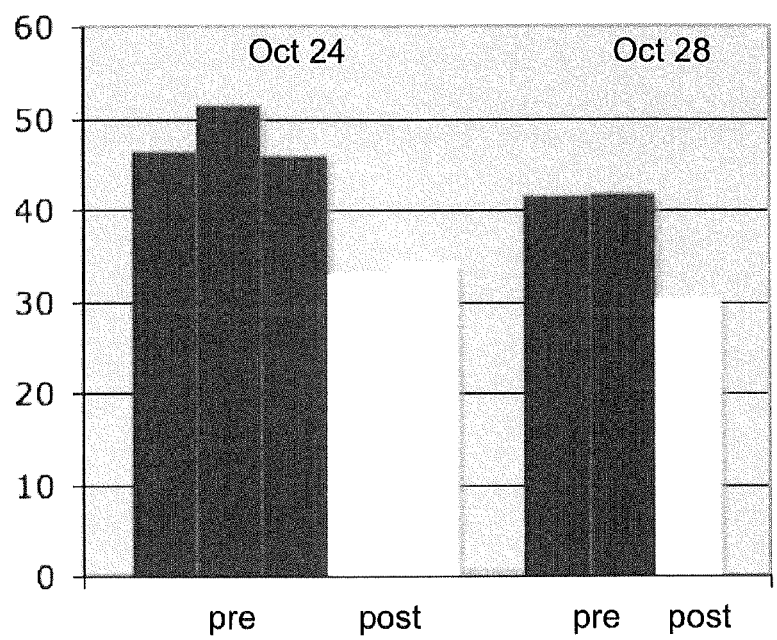
FIG. 49. Heart rate variability data for a male subject treated with dual ear sawtooth waveform caloric vestibular stimulation.

The CVS treatment was a 42° C. sawtooth wave applied to the left ear and a 17° C. sawtooth applied to the right ear. The treatment lasted for 10 minutes. HRV data were recorded immediately after the end of the treatment. HRV is a dimensionless measure. During the October $24^{th}$ test, average HRV dropped by 30% and on October $28^{th}$ by 27% (see FIG. 49).

Discussion:

HRV is proposed as a marker of effective CVS induction and could thus be used as a tool for titrating CVS dosing. Pathological conditions (such as cluster headaches discussed here) can lead to elevated HRV levels. Other pathological conditions, e.g. cardiac insufficiencies, are often associated with abnormally low HRV values (for that individual).

Example 26

Treatment of Fibromyalgia

A subject (also female, age 50-55) was diagnosed with fibromyalgia 3 years ago. Multiple allopathic and homeopathic interventions provided no substantive relief. The subject has co-morbid migraine headaches.

Figure 50:
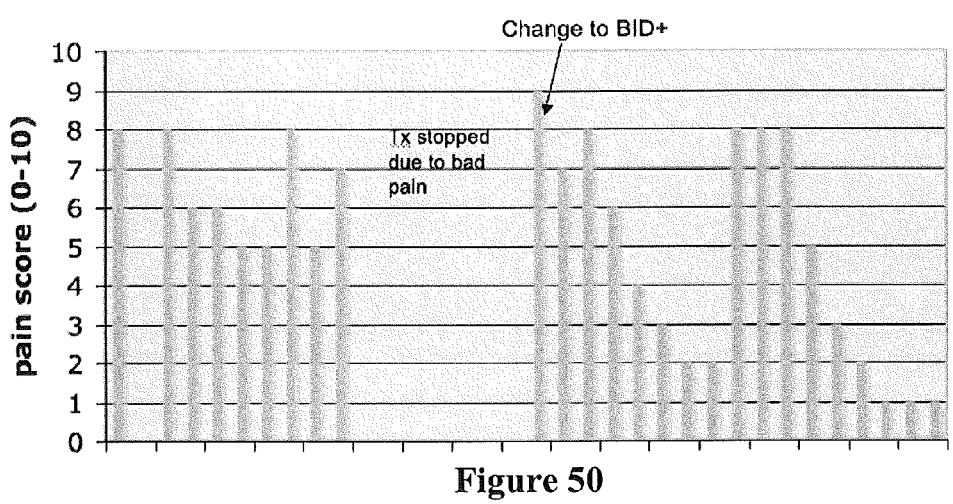
FIG. 50 Migraine pain scores (zero least severe; ten most severe) for a female subject treated with single ear sawtooth waveform caloric vestibular stimulation.

Methods and Results:

The subject underwent CVS treatment in the right ear, with a 17 deg C. sawtooth waveform. The subject's migraine pain scores versus time are listed in FIG. 50.

From September 13-19 the subject stopped CVS treatment due to significant pain and inability to function. On September 20 the subject began treatments twice per day, sometimes using a $3^{rd}$ daily treatment using the CVS parameters listed above. She realized an improvement in both migraine pain and pain from fibromyalgia. In the September 28-30 timeframe thunderstorms seemed to trigger additional migraine pain, but this abated over the following days until her pain level was barely noticeable.

The subject commented upon starting twice-a-day treatments: "I'm writing to report excellent results using 2 treatments. Last night I tried 2 consecutive treatments, and I felt great! Like I'd been to a spa and had a relaxing massage and soak in the hot tub."

The subject reported on September $26^{th}$: "This weekend I was able to work with [husband] getting 14 new bushes in the yard and picking out new paint at Lowe's to repaint the shutters on the house. I'm so very hopeful and happy. Gardening is a shared passion for us, and the first two years here, I wasn't able to even water the plants, so the ones left are real survivors! I feel like you are giving me my life back, and giving [husband] his wife back"

When the subject's spouse was asked if the CVS device was truly helpful he responded: "Nothing in the last 3 years had helped before this."

After October 6, the unit was retrieved. The subject has since returned to baseline.

Example 27

Treatment of Peripheral Neuropathy

A female subject underwent spinal surgery and sustained damage to the spinal cord. Thereafter she has had intractable peripheral neuropathy (foot pain) over a roughly 4 month period that had not responded to analgesics. The subject has obtained relief using CVS, with the extent and duration of relief depending on the device used and the waveform details.

Methods and Results:

The subject underwent CVS treatment with the following chronology:

1. Dual ear CVS unit: L-ear, sawtooth, 34 to 20° C.; R-ear, sawtooth, 34 to 42° C., 10 min. therapy. The treatment made her very sleepy (deep sleep for 20 min). Within 30 minutes, she was pain free and stayed so for 3 days, which was extraordinary for her.

2. Single (right) ear CVS unit, sawtooth, 34 to 17° C., 10 min therapy. She realized about a 50% reduction in pain level that lasted around 2 hours.

3. Single (right) ear CVS unit, long (single rise) square wave, 34 to 48° C., 10 min. She finds that the single ear, warm treatment is better than single ear, cold treatment. She must use the device several times a day to achieve pain relief.

4. Dual ear CVS unit, L-ear 17° C. square wave, R-ear 44° C. sawtooth, 10 min. Deep sleep for 45 min (at 5 PM). Foot pain ceased.

Discussion:

The subject received extended (multiple day) pain relief from one 10 min session using dual ear CVS. Single ear CVS, using a sawtooth waveform (slower slew rate) and an early device (basically a single cold/warm square wave), led to partial pain reduction for a time limited to hours. Therefore, the dual ear CVS treatment was superior to single ear for pain reduction. This subject and another have stated that the mixed waveform, dual ear (e.g., example 4) results in more significant subjective sensations (deep relaxation/sleep for this subject, increased nausea for the other). It is unclear with this single case if the mixed waveform treatment leads to increased pain reduction efficacy (both dual ear treatments were significant).

Example 28

Single Ear Treatment of Episodic Migraine

This Example evaluates the feasibility of using a portable CVS unit in a home setting over a month or more. The hypothesis was that daily CVS treatment would reduce the overall pain level and frequency of headaches.

Methods and Results:

The subject is a 50-55 year old female with a history of 6-8 migraine headache days per month (a month is taken as 28 days when reporting on migraine frequency). The subject used a right-ear CVS device and a sawtooth waveform that went from 34° C. to 17° C. with a period of roughly 1.7 minutes. The duration of the treatment was 10 minutes per session (daily sessions, moving to every other day after about 2 weeks of treatment). The average slew rate for heating was 40° C./minute and the average slew rate for cooling was 14° C./minute.

Figure 51:
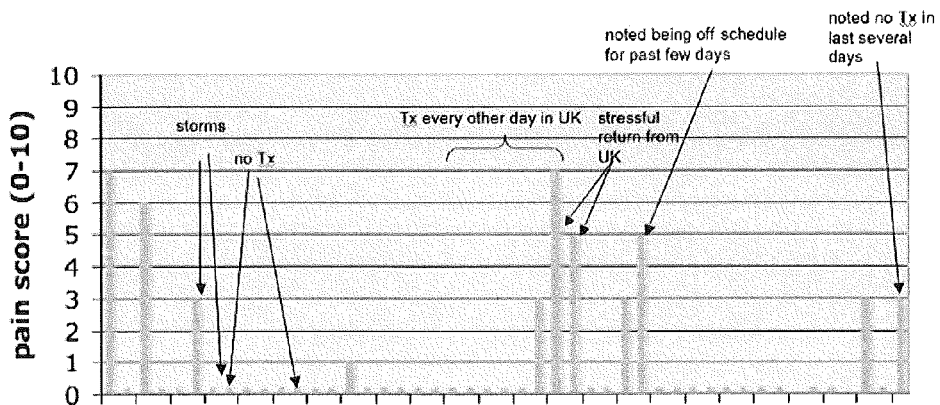
FIG. 51. Pain scores (zero least sever; ten most severe) for a female subject suffering from peripheral neuropathy treated with single ear and dual ear sawtooth waveform caloric vestibular stimulation.

The subject experienced a decrease in pain over the first week of therapy. (pain scores in FIG. 51). In the 40 days past the one week transitionary period, the subject had only one migraine headache (again, to qualify as a migraine it must be at a pain level of 6 or more on a scale of zero to ten and last for 4 hours or more). The one headache occurred during unusual stress associated with a transatlantic trip and disruption of work schedule upon her return. The subject also noted a subjective improvement in co-morbid depression over the treatment period.

Example 29

Titration of CVS Therapy for Type II Diabetes

The intent of this report is to show experimental evidence of the control of glucose levels by adjusting the frequency with which CVS is used in a subject with type II diabetes.

Figure 52:
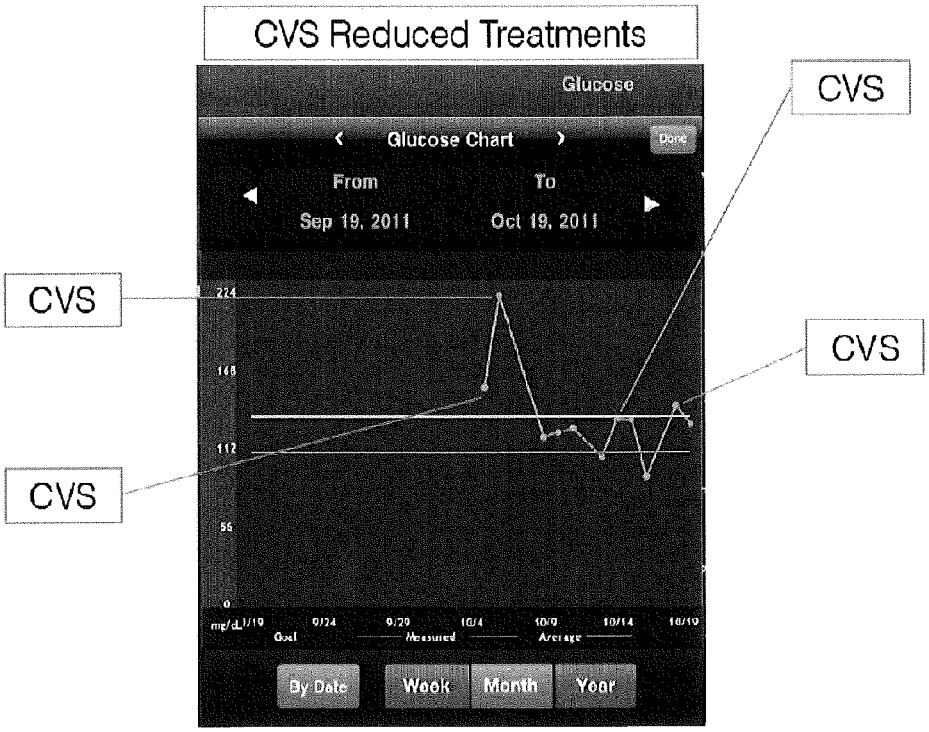
FIG. 52. Serum glucose levels for a male subject afflicted with type II diabetes and treated with dual ear caloric vestibular stimulation.

Methods and Results:

The subject is a 40-45 year old male diagnosed with type II diabetes within the last two years. As reported earlier, the subject has been able to forego the use of medications to control serum glucose levels, using CVS therapy instead. Recently, the subject has started using dual ear CVS, with a warm time-varying waveform applied to one ear and a cold time-varying waveform applied to the other. The dual ear therapy reduced the frequency with which the subject needed to use CVS in order to control serum glucose levels as shown in the graph in FIG. 52. Dual ear CVS was used with a 17° C. square wave for the right ear and a 42° C. sawtooth on the left ear. Each point in the graph represents a daily measurement (consistent time during each day). The red lines show when CVS was used. As the glucose levels were tracked, they would tend to move up in between CVS treatments, thus signaling when another treatment should be applied. This feedback method should be able to be extended to other patients, using their specific glucose levels to titrate frequency and intensity of CVS treatments. This subject remains off any other medications to control glucose levels.

Discussion:

This is an update report to supplement accounts from this subject already included in the Examples above, and further shows that serum glucose is a useful metric for CVS titration.

Example 30

CVS Intensity for Different Waveforms

As the CVS treatment device has evolved, we have moved from single to dual ear stimulation and have increased the slew rate to allow waveforms to be played out at a higher frequency. This report lists subjective metrics that can be used to assess the strength of CVS stimulation for a given subject.

Methods and Results:

The subject is a 40-45 year old male using CVS therapy chronically for type II diabetes and seasonal cluster headaches. He ranks the level of intensity of the CVS experience as follows:

single ear:
  daily treatments were required to control cluster headaches and serum glucose levels
  typical treatment is a cold sawtooth wave going between 34 and 17° C.
dual ear, same waveform shape, warm and cold:
  only 1-3 treatments per week are needed to control cluster headaches and serum glucose
  typical waveform is a sawtooth going from 34 to 42-44° C. in one ear and 34 to 17° C. in the other ear.
  Not much subjective difference compared with single ear during treatment
    More pronounced dizziness upon standing
    Nausea more persistent
    Faster, more complete responses for increased pain level
    Blurred vision for 3-5 minutes (possibly nystagmus)
dual ear, different waveform shape, warm and cold:
  only 1-3 treatments per week are needed to control cluster headaches and serum glucose
  typical waveform is a sawtooth going from 34 to 42-44° C. in one ear and a square wave in the other ear going from 34 to 17-20° C.
  most potent of all types tried in terms of pain mitigation and positive mood effects (side effects do not outweigh additional benefits)
    sleep inducing
    nausea while in horizontal position
    significant nausea and brief period of poor postural control upon standing
    persistent feeling of head fullness Discussion:

The most significant metrics for CVS therapy for pain patients is its effects on pain level and relative side effects.

This report recounts observations by one subject that can serve as a paradigm for how other patients can be assessed in the clinic. The right titration will involve an on-going assessment of effects on symptoms (e.g., pain) and minimization of unwanted, lasting side effects (for clarity, the side effects reported above are transient). There are tradeoffs that patients can make between efficacy with more intense side effects balanced against less frequent need to treat.

The following parameters can be varied in a dual ear system:
1. temperature (magnitude and sign with respect to body temperature)
2. waveform shape
3. frequency of waveform(s); if they are different frequencies, they could be commensurate and beat frequencies could be established.
4. relative phase of waveforms (e.g., in phase or some degree of being out of phase if they have the same frequency)
5. variable frequency during the course of a treatment (each side)

The CVS device can be programmed, in principal, to play out a different combination every day, thus frustrating any tendency of the VS of the patient to adapt to a given therapeutic waveform. This is a principal advantage of dual ear over single ear CVS.

Example 31

Treatment of Sleep Disorders/Insomnia with CVS

A common report from users of the CVS device is that they have beneficial effects in terms of sleeping soundly. It is known (e.g., Horii et al., *J. Neurophysiol*, 70, 1822, (1993)) that CVS does activate the hypothalamus. The hypothalamus in turn controls the sleep/wake cycle in mammals.

Methods and Results:

The reports of the soporific effects of CVS with subjects is variable and subjective. Listing the claims by subjects in order of frequency:
1. a relaxed feeling right after the completion of a CVS treatment
2. report of having an exceptionally complete sleep cycle on the night following a CVS treatment
3. A very powerful soporific effect that resulted in the subject falling asleep during a 10-20 minute CVS treatment and staying asleep for up to several hours.

Examples of each of the observations listed above:
1. A small pilot clinical trial was performed at a private headache clinic on patients who were being treated for migraine headache. The CVS waveform used was a sawtooth, right ear only, with the temperature oscillating between 34 and 17° C. None of the subjects fell asleep during the 10 minute CVS treatment, but commonly reported being relaxed in a way that was greater than what they would feel when lying down, in a similar position, for the same amount of time.
2. A male, age 50-55 acting as a normal test subject used single ear (right) CVS, sawtooth waveform oscillating between 34 and 17° C. He reported pleasant drowsiness after the 10 minute therapy session and then reported that he'd slept exceptionally soundly that night.
3. A subject using CVS for foot pain (see previous Example on this subject) used a dual ear CVS device: L-ear, sawtooth, 34 to 20° C.; R-ear, sawtooth, 34 to 42° C., 10 min. therapy. The treatment made her very sleepy (deep sleep for 20 min). Then again: dual ear, L-ear 17° C. square wave, R-ear 44° C. sawtooth, 10 min. Deep sleep for 45 min (at 5 PM) and had to be awakened.

In all cases, subjects reported restful sleep versus "forced" sleep and they reported no ill side effects.

Example 32

Single Ear CVS Treatment of Pediatric Epilepsy

The intent with this study was to evaluate using the Gen 2.0 CVS unit (left ear only, same earpiece but different (less powerful) TEC (thermoelectric cooler or Peltier cooler) than will be used in Gen 3 device) in a single session to observe any effects on spike activity in epileptic patients as monitored by EEG.

Figure 53:
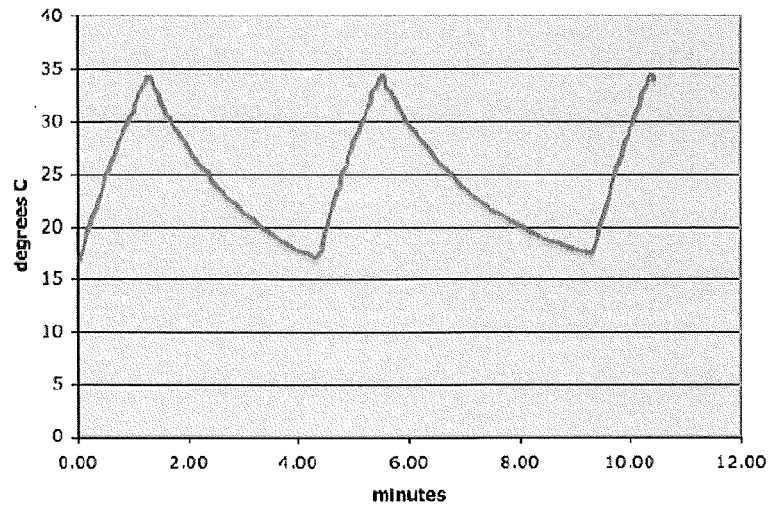
FIG. 53. Sawtooth CVS waveform administered to a representative pediatric epilepsy subject.

Methods and Results:

The subjects were treated with a sawtooth waveform that went from 34° C. to 17° C. (left ear only). Note that the actual temperature profile was not the same for all patients. For patient 3, the average slew rate on heating was around 14-15° C./min and the cooling rate dropped from about 5.8° C./min to 4.5° C./min (FIG. 53). It can be seen that more time was required to in the second "dip" to get to 17° C. This is due to insufficient power in the Gen 2.0 CVS device.

For patient 4, the inadequate power of the unit is even more apparent. The average heating slew rate was about the same as with patient 3, but the cooling rate started at 4.2° C./min and dropped to 3.6/min (not shown). The device failed to reach the 17° C. target temperature.

Figure 54:
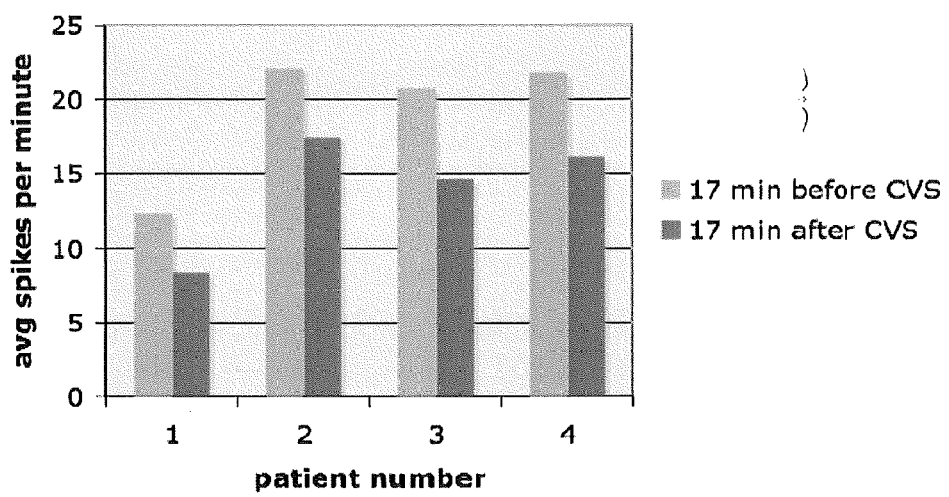
FIG. 54. Average number of spikes per minute for four pediatric epilepsy subjects treated with caloric vestibular stimulation as in FIG. 53, before and after stimulation.

The spike rate, as measured by continuous EEG, of the baseline (before CVS treatment) versus post CVS treatment is shown in FIG. 54. The decrease in spike rate lasted from 1-2 hours for each of the four patients. The reduction in spiking ranges from 21-32%.

Discussion:

Despite the underperformance of the Gen 2.0 model, primarily caused by an older, less powerful TEC and the lack of a cooling fan on the heat sink, demonstrable effects were seen in all 4 patients in terms of a reduction in spike activity that persisted past the end of the CVS treatment session. At this time, we don't have the ability to try a more advanced device (e.g., Gen 2.5) with these patients. A logical course would be to treat the patients longitudinally to see if the effects of CVS could be made more lasting. Despite the challenge of performing CVS on this population (age range from 6-10 years old), it was accomplished and there were no side effects of the treatment.

The foregoing is illustrative of the present invention, and is not to be construed as limiting thereof. The invention is defined by the following claims, with equivalents of the claims to be included therein.

That which is claimed is:

1. A device for delivering caloric vestibular stimulation to an individual, comprising:
    (a) an earpiece configured to be at least partially insertable into the ear canal of the individual for delivering said caloric vestibular stimulation;
    (b) a power supply operatively associated with said earpiece; and
    (c) a controller operatively associated with said power supply and said earpiece for configuring said caloric vestibular stimulation as at least a first and second time-varying waveform configured to induce nystagmus such that the nystagmus is substantially present over a period of at least four minutes.

2. The device of claim 1, further comprising
   (d) a thermoelectric device connected to said earpiece, wherein said earpiece is operatively associated with said controller through said thermoelectric device.

3. The device of claim 2, further comprising:
   (e) a temperature sensor thermally connected to said earpiece and operatively associated with said controller;
   and wherein said controller delivers said time-varying waveforms as actively controlled time varying waveforms responsive to said temperature sensor.

4. The device of claim 1, further comprising:
   (f) a heat sink operatively associated with said earpiece.

5. The device of claim 1, wherein said earpiece is comprised of metal.

6. The device of claim 1, wherein said at least a first and second time-varying waveform comprises from 3 to 10 sequential waveforms.

7. The device of claim 1, wherein each of said time varying waveforms comprises a ramped leading edge and/or a ramped trailing edge.

8. The device of claim 1, wherein each of said time varying waveforms, which may be the same or different, has a duration of from 1 minute to 20 minutes and an amplitude of from 5 to 24 degrees Centigrade.

9. The device of claim 1, wherein said time varying waveforms are delivered in a sequence in a treatment session, said treatment session having a total duration of five to 20 minutes.

10. The device of claim 1, further comprising:
    (d) a thermoelectric device connected to said earpiece, and wherein said earpiece is operatively associated with said controller through said thermoelectric device;
    (e) a temperature sensor thermally connected to said earpiece and operatively associated with said controller; and wherein said controller delivers said time-varying waveforms as actively controlled time varying waveforms responsive to said temperature sensor; and
    (f) a heat sink operatively associated with said earpiece, and wherein:
    said earpiece is comprised of metal; and
    said at least a first and second time-varying waveform consists of from 3 to 10 sequential waveforms having a ramped leading edge, a ramped trailing edge, and an amplitude of from 5 to 24 degrees Centigrade, which sequential waveforms are delivered in a treatment session having a duration of five to 20 minutes and are configured to induce nystagmus such that the nystagmus is substantially present over a period of at least four minutes.

11. The device of claim 1, wherein said time varying waveforms are administered so that saturation of vestibular nerve activation in said individual is reduced.

12. The device of claim 11, wherein said time varying waveforms are administered so that activation of a fastigial nucleus in said individual is enhanced.

13. A method of administering caloric vestibular stimulation to a subject in need thereof, comprising:
    administering caloric vestibular stimulation (CVS) to said subject in a treatment-effective amount,
    said caloric vestibular stimulation comprising at least a first and a second actively controlled time varying waveform stimulus configured to induce nystagmus such that the nystagmus is substantially present over a period of at least four minutes.

14. The method of claim 13, wherein:
    (a) said subject is afflicted with a condition associated with a mitochondrial disorder or myopathy;
    (b) said subject is afflicted with a condition selected from the group consisting of Parkinson's disease, migraine headache, depression, anxiety, type II diabetes, dementia, spatial neglect, seizures, and post-traumatic stress disorder; or
    (d) said CVS is administered in an amount effective to enhance cognition or cognitive reserve in said subject.

15. The method of claim 13, wherein said at least a first and second time-varying waveform comprises from 3 to 10 sequential waveforms.

16. The method of claim 13, wherein each of said time varying waveforms comprises a ramped leading edge and/or a ramped trailing edge.

17. The method of claim 13, wherein each of said time varying waveforms, which may be the same or different, has a duration of from 1 minute to 20 minutes and an amplitude of from 5 to 24 degrees Centigrade.

18. The method of claim 13, wherein said time varying waveforms are delivered in a sequence in a treatment session, said treatment session having a total duration of five to 20 minutes.

19. The method of claim 13, wherein said time varying waveforms are administered so that saturation of vestibular nerve activation in said individual is reduced.

20. The method of claim 13, wherein said at least a first and second time-varying waveform consists of from 3 to 10 sequential waveforms having a ramped leading edge, a ramped trailing edge, and an amplitude of from 5 to 24 degrees Centigrade, which sequential waveforms are delivered in a treatment session having a duration of five to 20 minutes.

* * * * *

UNITED STATES PATENT AND TRADEMARK OFFICE
CERTIFICATE OF CORRECTION

PATENT NO. : 9,849,026 B2  
APPLICATION NO. : 13/990274  
DATED : December 26, 2017  
INVENTOR(S) : Rogers et al.

Page 1 of 1

It is certified that error appears in the above-identified patent and that said Letters Patent is hereby corrected as shown below:

In the Specification

Column 23, Line 39: Please correct "A1e" to read -- A1c --

Column 32, Line 41: Please correct "$11e$" to read -- $11c$ --

Column 32, Line 63: Please correct "ilk" to read -- $11k$ --

Column 33, Line 1: Please correct "$11e$" to read -- $11c$ --

Column 40, Line 4: Please correct "lie" to read -- $11c$ --

Column 40, Line 28: Please correct "$11e$" to read -- $11c$ --

Column 41, Line 55: Please correct "$18$ as" to read -- $18as$ --

Signed and Sealed this  
Twenty-third Day of October, 2018

Andrei Iancu  
*Director of the United States Patent and Trademark Office*